United States Patent
Boucher et al.

(10) Patent No.: US 10,335,558 B2
(45) Date of Patent: **\*Jul. 2, 2019**

(54) METHODS OF TREATMENT

(71) Applicant: PARION SCIENCES, INC., Durham, NC (US)

(72) Inventors: Richard C. Boucher, Chapel Hill, NC (US); Michael Ross Johnson, Chapel Hill, NC (US); William R. Thelin, Chapel Hill, NC (US); Brian Button, Hillsborough, NC (US); Tomas Navratil, Carrboro, NC (US)

(73) Assignee: PARION SCIENCES, INC., Durham, NC (US)

( \* ) Notice: Subject to any disclaimer, the term of this patent is extended or adjusted under 35 U.S.C. 154(b) by 761 days.

This patent is subject to a terminal disclaimer.

(21) Appl. No.: 14/293,255

(22) Filed: Jun. 2, 2014

(65) Prior Publication Data

US 2015/0101597 A1    Apr. 16, 2015

Related U.S. Application Data

(63) Continuation of application No. 13/491,275, filed on Jun. 7, 2012, now Pat. No. 8,778,383.
(Continued)

(51) Int. Cl.
*A61M 16/00* (2006.01)
*A61M 11/00* (2006.01)
(Continued)

(52) U.S. Cl.
CPC ......... *A61M 11/003* (2014.02); *A61K 9/0078* (2013.01); *A61M 11/002* (2014.02);
(Continued)

(58) Field of Classification Search
CPC .............. A61M 15/0086; A61M 11/06; A61M 16/0666; A61M 16/14; A61M 11/003; A61M 16/0672; A61M 11/02; A61M 15/009; A61M 15/08; A61M 15/0085; A61M 2202/0275; A61M 2206/14; A61M 2206/16; A61K 9/12; A61K 9/0073
See application file for complete search history.

(56) References Cited

U.S. PATENT DOCUMENTS 2,534,636 A \* 12/1950 Stirn ..................... A61M 13/00
                                                                128/203.15
3,652,015 A    3/1972 Beall
(Continued)

FOREIGN PATENT DOCUMENTS

EP    1481702    12/2004
EP    1715909    11/2006
(Continued)

OTHER PUBLICATIONS

Office Action for Canadian Application No. 2,702,094, dated Dec. 10, 2014.
(Continued)

*Primary Examiner* — Steven O Douglas
(74) *Attorney, Agent, or Firm* — Cooley LLP

(57) ABSTRACT

Embodiments disclosed herein are directed to methods, compositions and apparatus for administering active agents to the lungs of a subject.

10 Claims, 38 Drawing Sheets

Related U.S. Application Data

(60) Provisional application No. 61/494,198, filed on Jun. 7, 2011, provisional application No. 61/496,317, filed on Jun. 13, 2011, provisional application No. 61/639,619, filed on Apr. 27, 2012.

(51) Int. Cl.

| | |
|---|---|
| *A61M 16/16* | (2006.01) |
| *A61M 16/06* | (2006.01) |
| *A61M 11/06* | (2006.01) |
| *A61M 15/00* | (2006.01) |
| *A61M 16/14* | (2006.01) |
| *A61K 9/00* | (2006.01) |
| *A61M 16/12* | (2006.01) |

(52) U.S. Cl.
CPC .......... *A61M 11/005* (2013.01); *A61M 11/06* (2013.01); *A61M 15/0086* (2013.01); *A61M 16/0666* (2013.01); *A61M 16/12* (2013.01); *A61M 16/14* (2013.01); *A61M 16/16* (2013.01); *A61K 9/0075* (2013.01); *A61M 15/0085* (2013.01); *A61M 2202/0275* (2013.01); *A61M 2206/14* (2013.01); *A61M 2206/16* (2013.01)

(56) References Cited

U.S. PATENT DOCUMENTS

| | | | |
|---|---|---|---|
| 4,159,803 A | 7/1979 | Cameto et al. |
| 4,268,460 A | 5/1981 | Boiarski et al. |
| 4,312,860 A | 1/1982 | Clements |
| 4,479,932 A | 10/1984 | Bodor |
| 4,501,729 A | 2/1985 | Boucher et al. |
| 4,540,564 A | 9/1985 | Bodor |
| 5,002,048 A | 3/1991 | Makiej, Jr. |
| 5,007,419 A | 4/1991 | Weinstein et al. |
| 5,049,389 A | 9/1991 | Radhakrishnan |
| 5,100,806 A | 3/1992 | Macri |
| 5,292,498 A | 3/1994 | Boucher, Jr. |
| 5,388,574 A | 2/1995 | Ingebrethsen |
| 5,437,267 A | 8/1995 | Weinstein et al. |
| 5,477,852 A | 12/1995 | Landis et al. |
| 5,483,953 A | 1/1996 | Cooper |
| 5,533,506 A | 7/1996 | Wood |
| 5,614,216 A | 3/1997 | Janoff |
| 5,656,256 A | 8/1997 | Boucher et al. |
| 5,687,715 A | 11/1997 | Landis et al. |
| 5,817,028 A | 10/1998 | Anderson |
| 5,823,179 A | 10/1998 | Grychowski et al. |
| 5,876,970 A | 3/1999 | Benson et al. |
| 6,015,828 A | 1/2000 | Cuppoletti |
| 6,159,969 A | 12/2000 | Yano et al. |
| 6,214,536 B1 | 4/2001 | Boucher, Jr. |
| 6,223,745 B1 | 5/2001 | Hammarlund et al. |
| 6,264,975 B1 | 7/2001 | Boucher, Jr. |
| 6,348,589 B1 | 2/2002 | Pendergast et al. |
| 6,387,886 B1 | 5/2002 | Montgomery et al. |
| 6,422,240 B1 | 7/2002 | Levitsky et al. |
| 6,457,472 B1 | 10/2002 | Schwartz et al. |
| 6,518,239 B1 | 2/2003 | Kuo et al. |
| 6,527,151 B1 | 3/2003 | Pavkov et al. |
| 6,530,370 B1 | 3/2003 | Heinonen |
| 6,550,476 B1 | 4/2003 | Ryder |
| 6,630,121 B1 | 10/2003 | Sievers et al. |
| 6,811,767 B1 | 11/2004 | Bosch et al. |
| 6,818,629 B2 | 11/2004 | Peterson et al. |
| 6,858,614 B2 | 2/2005 | Johnson |
| 6,858,615 B2 | 2/2005 | Johnson |
| 6,903,105 B2 | 6/2005 | Johnson |
| 6,926,911 B1 | 8/2005 | Boucher, Jr. |
| 6,977,246 B2 | 12/2005 | Pendergast et al. |
| 6,992,096 B2 | 1/2006 | Karp et al. |
| 6,995,160 B2 | 2/2006 | Johnson |
| 7,026,325 B2 | 4/2006 | Johnson |
| 7,030,117 B2 | 4/2006 | Johnson |
| 7,064,129 B2 | 6/2006 | Johnson et al. |
| 7,064,148 B2 | 6/2006 | Ueno et al. |
| 7,186,833 B2 | 3/2007 | Johnson |
| 7,189,719 B2 | 3/2007 | Johnson |
| 7,192,958 B2 | 3/2007 | Johnson |
| 7,192,959 B2 | 3/2007 | Johnson |
| 7,192,960 B2 | 3/2007 | Johnson |
| 7,201,167 B2 | 4/2007 | Fink et al. |
| 7,223,744 B2 | 5/2007 | Yerxa et al. |
| 7,241,766 B2 | 7/2007 | Johnson |
| 7,247,636 B2 | 7/2007 | Johnson |
| 7,253,295 B2 | 8/2007 | Ueno et al. |
| 7,267,121 B2 | 9/2007 | Ivri |
| 7,314,046 B2 | 1/2008 | Schroeder et al. |
| 7,317,013 B2 | 1/2008 | Johnson |
| 7,332,496 B2 | 2/2008 | Johnson |
| 7,345,044 B2 | 3/2008 | Johnson |
| 7,345,051 B2 | 3/2008 | Zhou et al. |
| 7,368,447 B2 | 5/2008 | Johnson et al. |
| 7,368,450 B2 | 5/2008 | Johnson |
| 7,368,451 B2 | 5/2008 | Johnson et al. |
| 7,375,107 B2 | 5/2008 | Johnson |
| 7,399,766 B2 | 7/2008 | Johnson |
| 7,405,233 B2 | 7/2008 | Wilde et al. |
| 7,410,968 B2 | 8/2008 | Johnson et al. |
| 7,482,024 B2 | 1/2009 | Kuo et al. |
| 7,499,570 B2 | 3/2009 | Zoghlami et al. |
| 7,517,865 B2 | 4/2009 | Meyers |
| 7,531,525 B2 | 5/2009 | Yerxa et al. |
| 7,537,009 B2 | 5/2009 | Hale et al. |
| 7,553,855 B2 | 6/2009 | Young et al. |
| 7,607,436 B2 | 10/2009 | Smaldone et al. |
| 7,645,789 B2 | 1/2010 | Hadida Ruah et al. |
| 7,745,442 B2 | 6/2010 | Johnson et al. |
| 7,772,259 B2 | 8/2010 | Karp et al. |
| 7,807,834 B2 | 10/2010 | Johnson |
| 7,820,678 B2 | 10/2010 | Johnson |
| 7,842,697 B2 | 11/2010 | Johnson |
| 7,868,010 B2 | 1/2011 | Johnson et al. |
| 7,875,619 B2 | 1/2011 | Johnson |
| 7,897,577 B2 | 3/2011 | Johansson et al. |
| 7,900,625 B2 | 3/2011 | Kleinstreuer et al. |
| 7,905,229 B2 | 3/2011 | Giroux et al. |
| 7,956,059 B2 | 6/2011 | Johnson |
| 7,981,898 B2 | 7/2011 | Johnson et al. |
| 7,984,713 B2 * | 7/2011 | Hochrainer ....... A61M 15/0028 128/200.14 |
| 8,001,963 B2 | 8/2011 | Giroux |
| 8,008,494 B2 | 8/2011 | Johnson |
| 8,022,210 B2 | 9/2011 | Johnson |
| 8,058,278 B2 | 11/2011 | Johnson et al. |
| 8,061,352 B2 | 11/2011 | Grychowski et al. |
| 8,105,572 B2 | 1/2012 | Condos et al. |
| 8,124,607 B2 | 2/2012 | Johnson |
| 8,143,256 B2 | 3/2012 | Johnson |
| 8,163,758 B2 | 4/2012 | Johnson et al. |
| 8,198,286 B2 | 6/2012 | Johnson |
| 8,245,708 B2 | 8/2012 | Smaldone et al. |
| 8,288,391 B2 | 10/2012 | Johnson |
| 8,324,218 B2 | 12/2012 | Johnson |
| 8,551,534 B2 | 10/2013 | Boucher et al. |
| 8,778,383 B2 | 7/2014 | Boucher et al. |
| 8,945,605 B2 * | 2/2015 | Boucher ................ A61M 11/06 424/434 |
| 9,408,988 B2 | 8/2016 | Boucher et al. |
| 9,987,443 B2 | 6/2018 | Boucher et al. |
| 2002/0129812 A1 | 9/2002 | Litherland et al. |
| 2003/0091512 A1 | 5/2003 | Adjei et al. |
| 2003/0171332 A1 | 9/2003 | Abraham et al. |
| 2003/0209246 A1 | 11/2003 | Schroeder et al. |
| 2004/0244804 A1 | 12/2004 | Olsen et al. |
| 2005/0090505 A1 | 4/2005 | Johnson et al. |
| 2005/0129621 A1 | 6/2005 | Davies et al. |
| 2005/0229926 A1 | 10/2005 | Fink et al. |
| 2005/0229928 A1 | 10/2005 | Ivri et al. |
| 2006/0078506 A1 | 4/2006 | Niven et al. |
| 2006/0144399 A1 | 7/2006 | Davidowski et al. |

(56) References Cited

U.S. PATENT DOCUMENTS

| | | |
|---|---|---|
| 2007/0137653 A1 | 6/2007 | Wood |
| 2007/0157931 A1 | 7/2007 | Parker et al. |
| 2007/0202051 A1 | 8/2007 | Schuschnig |
| 2007/0202055 A1 | 8/2007 | Berry et al. |
| 2007/0265280 A1 | 11/2007 | Johnson |
| 2007/0267010 A1 | 11/2007 | Fink et al. |
| 2008/0000473 A1 | 1/2008 | Stephenson et al. |
| 2008/0035141 A1 | 2/2008 | Warner et al. |
| 2008/0066741 A1 | 3/2008 | LeMahieu et al. |
| 2008/0072899 A1 | 3/2008 | Niland et al. |
| 2008/0078382 A1 | 4/2008 | LeMahieu et al. |
| 2008/0090841 A1 | 4/2008 | Johnson et al. |
| 2008/0167466 A1 | 7/2008 | Johnson et al. |
| 2008/0176863 A1 | 7/2008 | Johnson et al. |
| 2008/0199410 A1 | 8/2008 | Johnson et al. |
| 2008/0223375 A1 | 9/2008 | Cortez et al. |
| 2008/0264415 A1 | 10/2008 | Eason et al. |
| 2008/0293740 A1 | 11/2008 | Johnson et al. |
| 2009/0018144 A1 | 1/2009 | Johnson et al. |
| 2009/0025713 A1 | 1/2009 | Keller et al. |
| 2009/0062308 A1 | 3/2009 | Johnson |
| 2009/0104272 A1 | 4/2009 | Boucher et al. |
| 2009/0203752 A1 | 8/2009 | Campbell et al. |
| 2009/0221597 A1 | 9/2009 | Ruah et al. |
| 2009/0246137 A1 | 10/2009 | Hadida Ruah et al. |
| 2009/0246820 A1 | 10/2009 | Singh et al. |
| 2009/0247458 A1 | 10/2009 | Watson et al. |
| 2009/0253714 A1 | 10/2009 | Johnson et al. |
| 2009/0253736 A1 | 10/2009 | Hadida Ruah et al. |
| 2009/0263495 A1 | 10/2009 | Watson et al. |
| 2009/0288658 A1 | 11/2009 | Charan et al. |
| 2009/0304604 A1 | 12/2009 | Bauer et al. |
| 2009/0306009 A1 | 12/2009 | Rosenmeier |
| 2009/0324724 A1 | 12/2009 | Johnson |
| 2010/0074881 A1 | 3/2010 | Boucher et al. |
| 2010/0081957 A1 | 4/2010 | Hyde et al. |
| 2010/0089395 A1 | 4/2010 | Power et al. |
| 2010/0130547 A1 | 5/2010 | Zhang et al. |
| 2010/0132716 A1 | 6/2010 | Selvarajan et al. |
| 2010/0168094 A1 | 7/2010 | Binch et al. |
| 2010/0184739 A1 | 7/2010 | Sheth et al. |
| 2010/0192957 A1 | 8/2010 | Hobson et al. |
| 2010/0209357 A1 | 8/2010 | Levitt |
| 2010/0209540 A1 | 8/2010 | Warner et al. |
| 2010/0215588 A1 | 8/2010 | Skaliter |
| 2010/0227888 A1 | 9/2010 | Ruah et al. |
| 2010/0258114 A1 | 10/2010 | Cortez et al. |
| 2010/0316628 A1 | 12/2010 | Breton et al. |
| 2011/0008366 A1 | 1/2011 | Wight et al. |
| 2011/0053831 A1 | 3/2011 | Milech et al. |
| 2011/0056492 A1 | 3/2011 | Longest et al. |
| 2011/0067704 A1 | 3/2011 | Kooij et al. |
| 2011/0104255 A1 | 5/2011 | Niitsu et al. |
| 2011/0120457 A1 | 5/2011 | Dhuper et al. |
| 2011/0171141 A1 | 7/2011 | Kellerman et al. |
| 2011/0195973 A1 | 8/2011 | Johnson |
| 2011/0214673 A1 | 9/2011 | Masionis |
| 2012/0107414 A1 | 5/2012 | Lipp et al. |
| 2012/0125332 A1 | 5/2012 | Niland et al. |
| 2012/0192863 A1 | 8/2012 | Power et al. |
| 2012/0204872 A1 | 8/2012 | Cohen |
| 2012/0251594 A1 | 10/2012 | Longest et al. |
| 2012/0304992 A1 | 12/2012 | Ratto et al. |
| 2013/0098360 A1 | 4/2013 | Hurmez et al. |
| 2014/0096765 A1 | 4/2014 | Boucher et al. |
| 2014/0109899 A1 | 4/2014 | Boucher et al. |
| 2014/0158127 A1 | 6/2014 | Boucher et al. |
| 2015/0150803 A1 | 6/2015 | Boucher et al. |

FOREIGN PATENT DOCUMENTS

| | | |
|---|---|---|
| GB | 2152819 | 8/1985 |
| JP | 2007-195838 | 8/2007 |
| JP | 2008-534193 | 8/2008 |
| JP | 2008-295756 | 12/2008 |
| WO | WO 2003/035141 | 5/2003 |
| WO | WO 2003/068301 | 8/2003 |
| WO | WO 2006/108558 | 10/2006 |
| WO | WO 2008/019294 | 2/2008 |
| WO | WO 2009/049159 | 4/2009 |
| WO | WO 2009/134524 | 11/2009 |
| WO | WO 2010/088191 | 8/2010 |
| WO | WO 2011/062510 | 5/2011 |

OTHER PUBLICATIONS

Office Action for Canadian Application No. 2,702,094, dated Jul. 20, 2015.
Office Action for Canadian Application No. 2,702,094, dated Mar. 31, 2016.
Patent Examination Report No. 1 for Australian Application No. 2014221224, dated May 24, 2016, 2 pages.
Office Action for U.S. Appl. No. 14/047,281, dated Dec. 4, 2015, 8 pages.
Patent Examination Report No. 1 for Australian Application No. 2012267938, dated Jun. 10, 2016, 3 pages.
Supplementary European Search Report for European Application No. 12797275.0, dated Oct. 10, 2014, 7 pages.
Notice of Reasons for Rejection for Japanese Application No. 2014-514631, dated Apr. 20, 2016, 7 pages.
Supplementary European Search Report for European Application No. 13781347.3, dated Feb. 9, 2016, 9 pages.
Office Action for U.S. Appl. No. 13/831,268, dated Mar. 25, 2014, 8 pages.
International Search Report and Written Opinion for International Application No. PCT/US2013/038368, dated Sep. 16, 2013, 13 pages.
Extended Search Report for European Application No. 13860137.2, dated May 27, 2016, 6 pages.
Office Action for Australian Application No. 2008310734, dated Dec. 14, 2012, 3 pages.
Office Action for U.S. Appl. No. 12/249,175, dated Nov. 20, 2012, 9 pages.
Office Action for U.S. Appl. No. 12/249,175, dated Oct. 7, 2010, 11 pages.
International Search Report and Written Opinion for International Application No. PCT/US2008/079519, dated Dec. 16, 2008.
Office Action for U.S. Appl. No. 13/491,275, dated Sep. 12, 2013, 15 pages.
International Search Report and Written Opinion for International Application No. PCT/US2012/041333, dated Nov. 5, 2012.
International Search Report and Written Opinion for International Application No. PCT/US2013/073708, dated Mar. 28, 2014, 15 pages.
Office Action for U.S. Appl. No. 12/501,654, dated Mar. 28, 2012, 12 pages.
Aerogen Limited, AeronebPro Micropump Nebulizer, Instruction Manual, 56 pages (2011).
Al-Sa'Doni, H. H. et al., "Current status and future possibilities of nitric oxide-donor drugs: Focus on S-Nitrosothiols," Mini-Reviews in Medicinal Chemistry, 5(3):247-254 (2005).
Berlinski, A. et al., "Nebulized drug admixtures: Effect on aerosol characteristics and albuterol output," J. Aerosol. Med., 19(4):484-490 (2006).
Bernacki, S. H. et al., "Mucin gene expression during differentiation of human airway epithelia in vitro," Am. J. Respir. Cell Mol. Biol., 20(4):595-604 (1999).
Bhashyam, A. et aL, "Aerosol delivery through nasal cannulas: An in vitro study," Journal of Aerosol Medicine, 21(2):1-7 (2008).
Bodor, N. et al., "Controlled delivery of theophylline: Chemistry of 7-Acyl- and 7,7'-Acyldithoephylline derivatives," J. Pharm. Sci. 67(8):1045-1050 (1978).
Bodor, N. et al., "Improved delivery through biological membranes. 11. A redox chemical drug-delivery system and its use for brain-specific delivery of phenylethylamine," J. Med. Chem. 26:313-318 (1983).

(56) References Cited

OTHER PUBLICATIONS

Bodor, N. et al., "Improved delivery through biological membranes XX: Nicotinamide—Dihydronicotinamide based ester-linked redox carrier systems," J. Pharm. Sci., 75(1):29-35 (1986).
Bompadre, S. G. et al., "G551D and G1349D, two CF-associated mutations in the signature sequences of CFTR, exhibit distinct gating defects," J. Gen Physiol., 129(4):285-298 (2007).
Bonnefous, C. et al., "Discovery of inducible nitric oxide synthase (iNOS) inhibitor development candidate KD7332, Part 1: Identification of a novel, potent, and selective series of quinolinone iNOS dimerization inhibitors that are orally active in rodent pain models," J Med. Chem., 52(9):3047-3062 (2009).
Boucher, R. C., "New concepts of the pathogenesis of cystic fibrosis lung disease," European Respiratory Journal, 23(1):146-158 (2004).
Burg, M. B., "Molecular basis of osmotic regulation," Am. J. Physiol. Renal Physiol., 268:F983-F996 (1995).
Caputo, A. et al., "TMEM16A, a membrane protein associated with calcium-dependent chloride channel activity," Science, 322:590-594 (2008).
Chua, H. L. et al., "The influence of age on aerosol deposition in children with cystic fibrosis," Eur. Respir. J., 7:2185-2191 (1994).
Clunes, M. T. et al., "Front-runners for pharmacotherapeutic correction of the airway ion transport defect in cystic fibrosis," Current Opin. Pharmacol., 8(3):292-299 (2008).
Coakley, R. D. et al., "Abnormal surface liquid pH regulation by cultured cystic fibrosis bronchial epithelium," Proc. Natl. Acad. Sci. USA, 100(26):16083-16088 (2003).
Coates, A. L. et al., "A comparison of amount and speed of deposition between the PARI LC Star jet nebulizer and an investigational eFlow nebulizer," J. Aerosol. Med. Pulm. Drug. Deliv., 24(3):157-163 (2011).
Cragoe, E. J., "The synthesis of amiloride and its analogs," Chapter 3 in: Amiloride and Its Analogs, pp. 25-36 [no date].
Davidson, D. J. et al., "A primary culture model of differentiated murine tracheal epithelium," Am. J. Physiol. Lung Cell Mol. Physiol., 279(4):L766-L778 (2000).
De Boeck, K. et al., "Inhaled corticosteroids and lower lung function decline in young children with cystic fibrosis," Eur. Respir. J., 37(5):1091-1095 (2011).
Donaldson, S. et al., "Mucus clearance and lung function in cystic fibrosis with hypertonic saline," The New England Journal of Medicine, 354(3):241-250 (2006).
Duijvestijn, Y. C. M. et al., "Systematic review of N-acetylcysteine in cystic fibrosis," Acta Peadiatr., 88:38-41 (1999).
Duringer, C. et al., "Agonist-specific patterns of $\beta_2$-adrenoceptor responses in human airway cells during prolonged exposure," British Journal of Pharmacology, 158(1):169-179 (2009).
Elkins, M. et al., "A controlled trial of long-term inhaled hypertonic saline in patients with cystic fibrosis," The New England Journal of Medicine, 354(3):229-240 (2006).
Flume, P. A. et al., "Cystic fibrosis pulmonary guidelines. Chronic medications for maintenance of lung health," Am. J. Respir. Crit. Care Med., 176(10):957-969 (2007).
Frerichs, C. et al., "Treatment strategies for cystic fibrosis: what's in the pipeline?" Expert Opin. Pharmacother., 10(7):1191-1202 (2009).
Gennaro, A. R., Remington: The Science and Practice of Pharmacy, vol. II, 19th Edition, Mack Publishing Company (1995), p. 1457.
Goralski, J. L. et al., "Osmolytes and ion transport modulators: new strategies for airway surface rehydration," Curr. Opin. Pharmacol., 10(3):294-299 (2010).
Gregory, R. J. et al., "Maturation and function of cystic fibrosis transmembrane conductance regulator variants bearing mutations in putative nucleotide-binding domains 1 and 2," Molecular and Cellular Biology, 11(8):3886-3893 (1991).
Gruber, A. D. et al., "Genomic cloning, molecular characterization, and functional analysis of human CLCA1, the first human member of the family of $Ca^{2+}$-activated $Cl^-$channel proteins," Genomics, 54:200-214 (1998).
Handler, J. S. et al., "Kidney cell survival in high tonicity," Comp. Biochem. Physiol., 117A(3):301-306 (1997).
Hansel, T. T. et al., "A selective inhibitor of inducible nitric oxide synthase inhibits exhaled breath nitric oxide in healthy volunteers and asthmatics," The FASEB Journal, 17:1298-1300 (2003).
Heyder, J. et al., "Deposition of particles in the human respiratory tract in the size range of 0.005-15 µm," J Aerosol. Sci., 17(5):811-825 (1986).
Hirsh, A. J. et al., "Pharmacological properties of N-(3,5-Diamino-6-chloropyrazine-2-carbonyl)-N'-4-[4-(2,3-dihydroxypropoxy)phenyl]butyl-guanidine Methanesulfonate (552-02), a novel epithelial sodium channel blocker with potential clinical efficacy for cystic fibrosis lung disease," J. Pharmacol. Exp. Ther., 325(1):77-88 (2008).
Hirsch, S. R. et al., "Sputum liquefying agents: a comparative in vitro evaluation," J. Lab. Clin. Med., 74(2):346-353 (1969).
Huang P. et al., "Regulation of human CLC-3 channels by multi-functional Ca2+/calmodulin-dependent protein kinase," The Journal of Biological Chemistry, 276(23):20093-20100 (2001).
Hummler, E. et al., "A mouse model for the renal salt-wasting syndrome pseudohypoaldosteronism," Proc. Natl. Acad. Sci USA, 94(21):11710-11715 (1997).
Jayaraman, S. et al., "Noninvasive in vivo fluorescence measurement of airway-surface liquid depth, salt concentration, and pH," The Journal of Clinical Investigation, 107(3):317-324 (2001).
Katsumi, H. et al., "Development of nitric oxide donors for the treatment of cardiovascular diseases," Cardiovascular & Hematological Agents in Medicinal Chemistry, 5(3):204-20 (2007).
Kerem, E. et al., "Pulmonary epithelial sodium-channel dysfunction and excess airway liquid in pseudohypoaldosteronism," N. Engl. J. Med., 341(3):156-162 (1999).
Lazarowski, E. R. et al., "Nucleotide release provides a mechanism for airway surface liquid homeostasis," J. Biol. Chem., 279(35):36855-36864 (2004).
LeBrun, P. P. H. et al., "A review of the technical aspects of drug nebulization," Pharm. World Sci., 22(3):75-81 (2000).
Longest, P. W. et al., "High-efficiency generation and delivery of aerosols through nasal cannula during noninvasive ventilation," Journal of Aerosol Medicine and Pulmonary Drug Delivery, 26(5):266-279 (2013).
Matsui, H. et al., "Evidence for periciliary liquid layer depletion, not abnormal ion composition in the pathogenesis of cystic fibrosis airways disease," Cell, 95:1005-1015 (1998).
Matsui, H. et al., "A physical linkage between cystic fibrosis airway surface dehydration and Pseudomonas aeruginosa biofilms," Proc Natl Acad Sci USA, 103(48):18131-18136 (2006).
Megson, I. L. et al., "Nitric oxide donor drugs: current status and future trends," Expert Opin. Investig. Drugs, 11(5):587-601 (2002).
Miller, M. R. et al., "Recent developments in nitric oxide donor drugs," British Journal of Pharmacology, 151(3):305-321 (2007).
Murray, M. J. et al. (eds.), Critical Care Medicine: Perioperative Management, American Society of Critical Care Anesthesiologists, Lippincott—Raven Publishers, pp. 431 and 439-445 (1997).
Muscara, M. N. et al., "V. Therapeutic potential of nitric oxide donors and inhibitors," Am. J. Physiol. Gastrointest. Liver Physiol., 276(6):G1313-G1316 (1999).
Nash, E. F. et al., "Nebulized and oral thiol derivatives for pulmonary disease in cystic fibrosis (review)," Cochrane Database Syst Rev., 21(1):CD007168 (2009).
O'Callahan, C. et al., "The science of nebulised drug delivery," Thorax, 52(2):S31-S44 (1997).
Palmer, D. et al., "Synergistic inhibition of vascular smooth muscle cell migration by phosphodiesterase 3 and phosphodiesterase 4 inhibitors," Circulation Research, 82(8):852-861 (1998).
PARI Pharma GmbH eFlow rapid Type 178G1005, Instructions for Use, Mar. 2012.
PARI Reusable Nebulizer Configurations, PARI Respiratory Equipment, Inc., Brochure—LC Nebulizers, pp. 1-2 (2010).
Quinton, P. M., "Cystic fibrosis: Lessons from the sweat gland," Physiology, 22(3);212-225 (2007).

(56) References Cited

OTHER PUBLICATIONS

Ramsey, B. W. et al., "Intermittent administration of inhaled tobramycin in patients with cystic fibrosis," N. Engl. J. Med., 340(1):23-30 (1999).
Randell, S. H. et al., "Effective mucos clearance is essential for respiratory health," Am. J. Respir. Cell. Mol. Biol., 35(1):20-28 (2006).
Ren, C. L. et al., "Relationship between inhaled corticosteroid therapy and rate of lung function decline in children with cystic fibrosis," J. Pediatr., 153(6):746-751 (2008).
Reusable Nebulizers [online] Jun. 2010, [retrieved on Jan. 6, 2011], retrieved from http://www.pari.com/downloads/product-brochures/PARI_LC_Nebs_Brochure_Rev-C_EN.pdf.
Ricciardolo, F. L.M. et al., "Nitric oxide synthase (NOS) as therapeutic target for asthma and chronic obstructive pulmonary disease," Current Drug Targets, 7(6):721-35 (2006).
Robinson, M. et al., "Effect of increasing doses of hypertonic saline on mucociliary clearance in patients with cystic fibrosis," Thorax, 52(10):900-903 (1997).
Rowe, S. M. et al., "ΔF508 CFTR processing correction and activity in polarized airway and non-airway cell monolayers," Pulm. Pharmacol. Ther., 23(4):268-278 (2010).
Sanabria, P. et al., "$P2Y_2$ receptor desensitization on single endothelial cells," Endothelium, 15(1):43-51 (2008).
Sawicki, G. S. et al., "High treatment burden in adults with cystic fibrosis: Challenges to disease self-management," J. Cyst. Fibros., 8(2):91-96 (2009).
Schroeder, B. C. et al., "Expression cloning of TMEM16A as a calciumactivated chloride channel subunit," Cell, 134:1019-1029 (2008).
Shek, E. et al., "Improved delivery through biological membranes. 3. Delivery of N-methylpyridinium-2-carbaldoxime chloride through the blood-brain barrier in its dihydropyridine pro-drug form," J. Med. Chem., 19(1):113-117 (1976).
Sood, N. et al., "Increasing concentration of inhaled saline with or without amiloride," Am. J. Respir. Crit. Care Med., 167(2):158-163 (2003).
Sun, H. et al., "The vitelliform macular dystrophy protein defines a new family of chloride channels," Proc Natl Acad Sci USA, 99(6):4008-4013 (2002).
Taube, C. et al., "Airway response to inhaled hypertonic saline in patients with moderate to severe chronic obstructive pulmonary disease," Am. J. Respir. Crit. Care Med., 164(10, Pt. 1):1810-1815 (2001).
Tsunenari, T. et al., "Structure-function analysis of the Bestrophin family of anion channels," J. Biol. Chem., 278(42):41114-41125 (2003).
Vallance, P. et al., "Nitric oxide: therapeutic opportunities," Fundamental & Clinical Pharmacology, 17(1):1-10 (2003).
Vecellio, L. et al., "Deposition of aerosols delivered by nasal route with jet and mesh nebulizers," International Journal of Pharmaceutics, 407:87-94 (2011).
Westerman et al., "Aerosolization of Tobramycin (TOBI®) with the PARI LC PLUS® Reusable Nebulizer: Which Compressor to Use? Comparison of the CR60® to the PortaNeb® Compressor," Journal of Aerosol Medicine and Pulmonary Drug Delivery, 21(3):269-280 (2008).
Yang, Y. D. et al., "TMEM16A confers receptor-activated calcium-dependent chloride conductance," Nature, 455:1210-1215 (2008).
Yerxa, B. R. et al., "Pharmacology of INS37217 [$P^1$-(Uridine 5')-$P^4$-(2'-deoxycytidine 5')tetraphosphate, Tetrasodium Salt], a next-generation $P2Y_2$ receptor agonist for the treatment of cystic fibrosis," J. Pharmacol. Exp. Ther., 302(3):871-880 (2002).
Yoon, S. S. et al., "Anaerobic killing of mucoid Pseudomonas aeruginosa by acidified nitrite derivatives under cystic fibrosis airway conditions," J. Clin. Invest., 116(2):436-446 (2006).
Zhou, Z. et al., "The βENaC-overexpressing mouse as a model of cystic fibrosis lung disease," Journal of Cystic Fibrosis, 10(2):S172-S182 (2011).
Examination Report for European Application No. 08837710.6, dated Jan. 3, 2017, 4 pages.
Notification of the First Office Action and Search Report for Chinese Application No. 201280035731.9, dated Feb. 16, 2015, 15 pages.
Office Action for European Application No. 12797275.0, dated Dec. 16, 2016, 5 pages.
Notice of Reasons for Rejection for Japanese Application No. 2014-514631, dated Dec. 26, 2016, 5 pages.
Patent Examination Report No. 1 for Australian Application No. 2013251480, dated Nov. 16, 2016, 3 pages.
Office Action for U.S. Appl. No. 14/593,757, dated Jan. 11, 2017, 20 pages.
Office Action for U.S. Appl. No. 14/099,657, dated Oct. 6, 2016, 12 pages.
Finlay, W. H., "Particle Size Distributions," Chapter 2 In: The Mechanics of Inhaled Pharmaceutical Aerosols: An Introduction, Academic Press, New York (2001), p. 3-15.
Negi, A. S. et al., "Colloidal State," Chapter 19 In: A textbook of Physical Chemistry, New Age International Limited Publishers (1985), p. 744, Table 19.1.
Mobley, C. et al., "Pharmacokinetic consideration in the design of pulmonary drug delivery system for glucocortocoids," Chap. 3 In: Drug Targeting Technology, Schreier, H. (ed.), Marcel Dekker Inc., New York (2001), p. 51 and 55-56.
Examination Report No. 1 for Australian Application No. 2017210594, dated Aug. 8, 2018, 3 pages.
Examination Report No. 1 for Australian Application No. 2017261520, dated Jun. 20, 2018, 3 pages.
Office Action for European Application No. 13860137.2, dated Aug. 7, 2018, 4 pages.
Notice of Reasons for Rejection for Japanese Application No. 2017-186369, dated Oct. 17, 2018, 16 pages.
Enderby, B. et al., "Hypertonic saline inhalation in cystic fibrosis—salt in the wound, or sweet success?," Arch Dis Child, 2007, vol. 92, No. 3, pp. 195-196.
Office Action for U.S. Appl. No. 14/099,657, dated Jan. 3, 2019, 18 pages.

\* cited by examiner

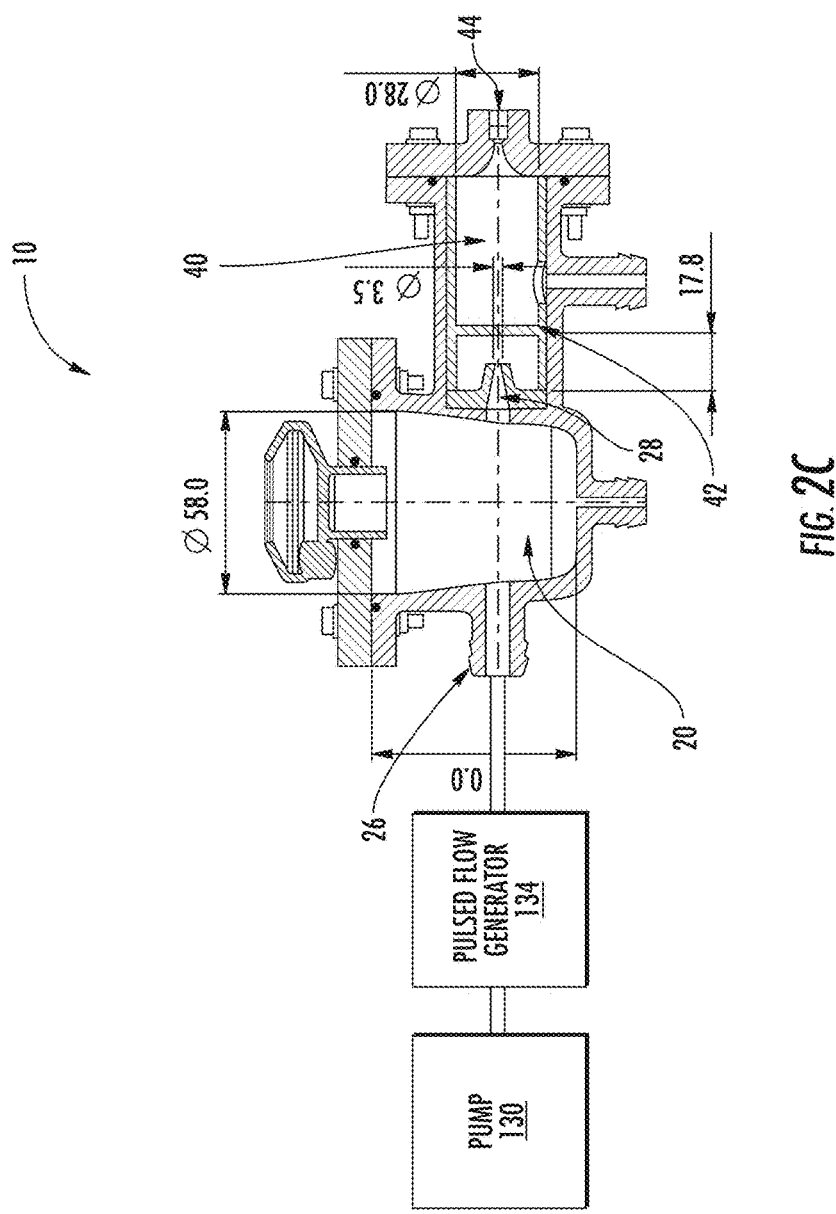

A)

[Graph showing Aerosol Deposition Rate (nl/min/cm²) vs Lung Generation, comparing Commercial Vibrating Mesh Nebulizer (dashed) and Commercial Jet Nebulizer (solid)]

B)

[Graph showing NaCl Deposition Rate (μg/min/cm²) vs Lung Generation, comparing Commercial Vibrating Mesh Nebulizer (dashed) and Commercial Jet Nebulizer (solid)]

FIG. 40

| NEBULIZER SIMULATED | NEBULIZER VOLUME OUTPUT (nl/min/cm2) | NEBULIZER NaCl MASS OUTPUT (ug/min/cm2) | TIME OF OPERATION (min) | TOTAL MASS OF NaCl DELIVERED (ug) |
|---|---|---|---|---|
| VIBRATING MESH (PARI eFLOW) | 200 | 14 | 7.5 | 105 |
| JET NEBULIZER (PARI LC STAR) | 100 | 7 | 15 | 105 |
| SLOW DELIVERY | 25 | 1.75 | 60 | 105 |

METHODS OF TREATMENT

This application is a continuation of U.S. Utility Application No.: 13/491,275, filed Jun. 7, 2012, which claims the benefit of and priority from U.S. Provisional Patent Application Ser. No. 61/494,198, filed Jun. 7, 2011, U.S. Provisional Patent Application Ser. No. 61/496,317, filed Jun. 13, 2011, and U.S. Provisional Patent Application Ser. No. 61/639,619, filed Apr. 27, 2012, the contents of each of which are incorporated herein by reference in their entirety.

FIELD OF THE INVENTION

The present invention concerns methods, compositions and apparatus for administering active agents to the lungs of a subject.

BACKGROUND

Aerosolized medicines are frequently used to treat individuals suffering from respiratory disease. The inhalation of aerosols is an effective approach to deliver therapeutic concentrations of medicines directly to the site of disease (e.g. the airways). Nebulizer devices, such as jet nebulizers, are commonly used to generate respirable aerosol particles (e.g. particles that are <10 mm in diameter) from liquid medication. Examples of Jet Nebulizers include the Pari LC Star and Pari LC Plus which often require 10-20 minutes to deliver a single dose of medication. For subjects with chronic pulmonary disease whom may require multiple daily aerosol treatments, the time burden associated with drug delivery via Jet nebulizers can become substantial (e.g. more than 2 or more hours per day dedicated to aerosol therapy). As an example of such therapy, Elkins et al., *N Engl J. Med*, 354(3):229-40(2006) showed that delivering 4 ml of 7% hypertonic saline twice a day via Pari LC Plus jet nebulizer to CF patients during their waking hours leads to a decreased rate of pulmonary exacerbations and modest improvement in lung function. At the same time, this treatment adds 30+ minutes spent on treatment per day. Similarly, Ramsey et al., *N Engl J Med*, 340(1):23-30 (1999) demonstrated that administering 5 ml of sterile tobramycin antibiotic solution via Pari LC PLUS jet nebulizer to CF patients during their waking hours leads to a decreased rate of pulmonary exacerbations and an improvement in lung function. At the same time, this treatment adds 40+ minutes spent on treatment per day.

One strategy to improve the time burden associated with aerosol therapy is via the delivery of medicines by newer, more efficient nebulizer devices. The current state-of-the-art in pulmonary medicine is the delivery of aerosolized medicines more rapidly and efficiently to the airways. The primary goal of these high-efficiency nebulizer systems is to reduce the drug delivery time and minimize the time burden on the patient. Examples of these devices include vibrating mesh nebulizers such as the PARI EFLOW™ nebulizer and the AEROGEN PRONEB™ nebulizer (operating parameters shown in Table 1). Vibrating mesh nebulizers are capable of delivering a dose of an inhaled agent comparable to a jet nebulizer in approximately half the time. The time saving stemming from the more efficient vibrating nebulizers is important for respiratory diseases where patients are exposed to a large treatment burden. Another example of such devices are metered dose inhalers and dry powder inhalers. While these devices have some limitations related to maximum deliverable dose and tolerability compared to nebulizers, they offer additional convenience to the patients via further reduced drug delivery times.

However, time saving due to the use of high-efficiency nebulizers may not be sufficient for respiratory diseases such as cystic fibrosis where patients are often required to take combination of several inhaled treatments, oral treatments, physiotherapy and exercise. It is not uncommon for CF patients to spend 2-3 hours per day on treatments that are recommended by treatment guidelines (Flume et al., Am J Respir Crit Care Med. 2007 Nov. 15; 176(10):957-69; Sawicki et al., *J Cyst Fibros*. 2009 March; 8(2):91-6). The treatment burden due to this extensive treatment regimen is so large that adding another inhaled treatment during patient's waking hours often leads to displacement of the other treatments or decreased compliance. For this reason, administration of inhaled treatments during patients sleeping hours may be beneficial as it does not contribute to the treatment burden experienced by these patients during the waking hours. Similarly, such overnight aerosol delivery may result in improved compliance associated with improved efficacy of both the overnight treatment and the daily treatments, compared to adding another inhaled treatment to existing treatment regimen.

The most commonly used nebulizer devices (including jet and vibrating mesh nebulizers) deliver aerosolized medicines to patients as concentrated "boluses" over a short time period (e.g. 5 to 20 minutes per treatment). These boluses lead to a rapid increase of the active therapeutic agent in lumen of the lung and the surrounding tissues, often above the necessary therapeutic concentration for a short period of time. Similarly, these boluses lead to systemic exposure to such agents. These peak local and systemic concentrations following bolus administrations of inhaled aerosols can lead to undesirable safety and tolerability profiles which may prevent adoption of the therapy into the standard of care. For example, chronic inhaled corticosteroids have been shown to have disease-modifying impact on the rate of lung function decline in CF (Ren et al., *J Pediatr.*, 153(6):746-5I (2008), de Boeck et al., *Eur Respir J.*, 37(5):1091-5 (2011)) but are accompanied by patients' decreased linear growth, and increased insulin/oral hypoglycemic use due to the systemic exposure. As such, inhaled corticosteroids are not recommended for general treatment of CF lung disease (Flume et al., Am J Respir Crit Care Med. 2007 Nov. 15; 176(10):957-69).

The most commonly used nebulizer devices (including jet and vibrating mesh nebulizers) deliver aerosolized medicines to patients as concentrated "boluses" over a short time period (e.g. 5 to 20 minutes per treatment). However, for many medications "bolus" aerosol delivery is not optimal.

The present invention can address previous shortcomings in the art by providing methods, compositions and apparatus for administering active agents to the lungs of a subject.

SUMMARY OF THE INVENTION

A first aspect of the invention is a method of treating at least one lung/the lungs of a subject in need thereof, comprising: administering an active agent to the at least one lung/the lungs of a subject (for example, by sustained administering or infusion administering).

In some embodiments, the administering is carried out by aerosol administration.

In some embodiments, the administering is carried out by inhalation administration.

In some embodiments, the administering step is carried out by a nasal cannula, face mask, or positive airway pressure mask (e.g., a continuous positive airway pressure (CPAP) mask or a bilevel positive airway pressure (biPAP) mask).

In some embodiments, the administering is carried out by administration of the active agent to airway surfaces.

In some embodiments, the administering is effective to enhance mucus clearance from at least one lung of the subject.

One non-limiting example of the invention is a method of enhancing mucus clearance from the lungs of a subject in need thereof, comprising: administering an osmolyte to airway surfaces of the lungs of said subject in an amount (i) sufficient to hydrate said lung airway mucus secretions and (ii) insufficient to substantially dehydrate lung airway epithelia] cells therebeneath, said administering step being carried out and for a time sufficient to enhance mucus clearance from the lungs of said subject. In some embodiments, the administering step is carried out by administering said subject an aerosol comprising said osmolyte such as saline or hypertonic saline.

A further aspect of the invention is an active agent as described herein in a pharmaceutically acceptable carrier (e.g., a liquid carrier, a dry powder carrier) for use in carrying out a method as described herein.

A further aspect of the invention is an aerosol generator or nebulizer (e.g., as described herein) for use in carrying out a method as described herein.

The foregoing is illustrative of the present invention, and is not to be construed as limiting thereof.

The present invention is explained in greater detail in the drawings set forth herein and the specification set forth below. The disclosures of all US Patent references cited herein are incorporated by reference herein in their entirety as if fully set forth.

BRIEF DESCRIPTION OF THE DRAWINGS

The accompanying drawings, which are incorporated in and constitute a part of the specification, illustrate embodiments of the invention and, together with the description, serve to explain principles of the invention.

DETAILED DESCRIPTION OF THE PREFERRED EMBODIMENTS

Figure 1:
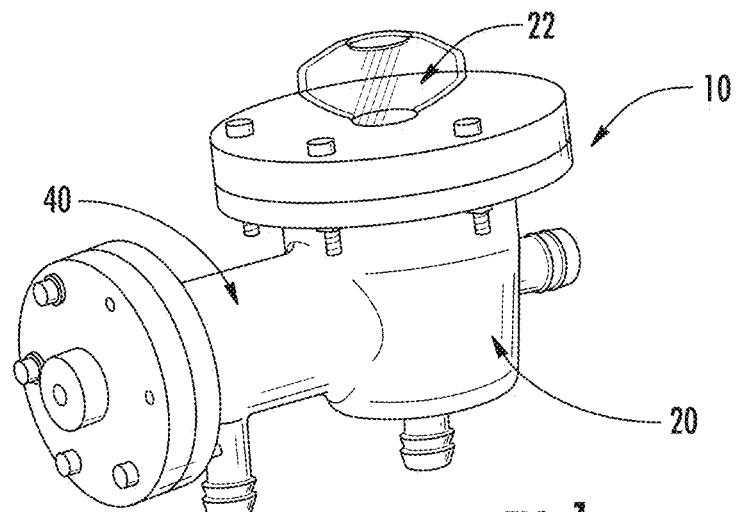
FIG. 1 is a perspective view of an aerosol delivery system or Incorporated Nebulization Chamber (INC)-based device according to some embodiments of the invention.

Counter to the current trend to maximize the rate of aerosol drug delivery and reduce the time for aerosolizing medications, the present method relates to delivering aerosolized therapeutic agents as a slow aerosol "infusion", or at a lower rate over an extended period of time, rather than as a short aerosol "bolus" delivery. The inventive method can provide a greater benefit than short bolus delivery. The deposition of aerosolized therapeutic agents at low rates over an extended period of time can be performed with a nebulizer system designed for delivery of the lower flow rates over a relatively long time period (e.g., 3 hours to 8 hours or overnight).

The present invention relates to a method of delivering an aerosolized active compound at a rate that is significantly slower than currently used and for a duration that is longer than currently used. This approach is counter to the current "faster is better" approach. However, the examples described herein will show that a slower aerosol delivery rate of active compound provides a three-fold benefit. First, the examples show that delivery of aerosolized mediations over an extended period of time are more therapeutically beneficial than a fast delivery rate of active compound for a shorter period of time (e.g., delivery by a conventional jet or vibrating mesh nebulizer). Second, the examples provided herein will show that the method of delivering therapeutic agents as aerosol "infusions" rather than "boluses" will minimize or eliminate undesired off-target effects. Importantly, these off-target effects (e.g. ciliastasis, broncho-constriction, pro-inflammatory agent secretion, high systemic drug exposure) can be eliminated by slow delivery/infusion apparatus. Third, the examples provided herein will demonstrate that the methods of this invention allow therapeutic use agents in formulations and strengths that were previously not usable with existing routes of aerosol delivery. Finally, delivery of aerosols at low flow rates over an extended period is compatible with sleep. As such, the delivery of aerosol "infusions" will reduce the amount of wake time (e.g. treatment or time burden) needed for aerosol therapies if administered overnight.

According to some embodiments, a method of the present invention comprises treating at least one lung/the lungs of a subject in need thereof, comprising: administering an active agent to the at least one lung/the lungs of a subject (for example, by sustained administering or infusion administering).

A further method of the present invention comprises a method of enhancing mucus clearance from a lung of a subject in need thereof, comprising: administering an osmolyte to airway surfaces of said lung of said subject in an amount and at a rate (i) sufficient to hydrate said lung airway mucus secretions and (ii) insufficient to substantially dehydrate lung airway epithelial cells therebeneath, said administering step being carried out and for a time sufficient to enhance mucus clearance from the lungs of said subject.

In some embodiments, a method of enhancing hydration of a surface of a lung of a subject in need thereof is provided, the method comprising: administering an osmolyte to airway surfaces of said lung of said subject in an amount and at a rate (i) sufficient to hydrate said surface and (ii) insufficient to substantially dehydrate lung airway epithelial cells therebeneath, said administering step being carried out and for a time sufficient to enhance hydration of said surface of said lung of said subject.

1. Definitions

Subjects to be treated by the methods of the present invention include both human subjects and animal subjects (e.g., dog, cat, monkey, chimpanzee) for veterinary purposes. The subjects may be male or female and may be any suitable age, e.g., neonatal, infant, juvenile, adolescent, adult, or geriatric. In some embodiments, the subjects are preferably mammalian.

"Osmolyte" active compounds as used herein refers to molecules or compounds that are osmotically active (i.e., are "osmolytes"). "Osmotically active" compounds are known (see, e.g., R. Boucher et al., *Multiple Nebulizer System*, US Patent Application 20100074881 (published Mar. 25, 2010) and may be membrane-impermeable (i.e., essentially non-absorbable) on the airway or pulmonary epithelial surface.

"Airway surface" and "pulmonary surface," as used herein, include pulmonary airway surfaces such as the bronchi and bronchioles, alveolar surfaces, and nasal and sinus surfaces.

"Saline" as used herein refers to a solution comprised of, consisting of, or consisting essentially of sodium chloride in water. Saline can be hypertonic, isotonic, or hypotonic. In some embodiments, saline can comprise sodium chloride in an amount of from about 0.1% to about 40% by weight, or any range therein, such as, but not limited to, about 0.1% to about 10%, about 0.5% to about 15%, about 1% to about 20%, about 5% to about 25%, about 10% to about 40%, or about 15% to about 35% by weight. In certain embodiments, sodium chloride is included in a solution in an amount of about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40% by weight, or any range therein.

"Hypertonic saline" as used herein refers to a solution comprised of consisting of, or consisting essentially of greater than 0.9 wt % sodium chloride in water. In general, the sodium chloride is included in the solution in an amount of from about 0.9% to about 40% by weight, or any range therein, such as, but not limited to, about 1% to about 15%, about 5% to about 20%, about 5% to about 25%, about 10% to about 40%, or about 15% to about 35% by weight. In certain embodiments, sodium chloride is included in the solution in an amount of about 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40% by weight, or any range therein.

"Hypotonic saline" as used herein refers to a solution comprised of, consisting of, or consisting essentially of less than 0.9 wt % sodium chloride in water. In some embodiments, sodium chloride is included in the solution in an amount of about 0.9%, 0.8%, 0.7%, 0.6%, 0.5%, 0.4%, 0.3%, 0.2%, 0.1% by weight, or any range therein.

"Isotonic saline" as used herein refers to a solution comprised of, consisting of, or consisting essentially of 0.9 wt % sodium chloride in water.

According to some embodiments, saline (e.g., hypertonic saline) can comprise an excipient. An excipient can be a pharmaceutically acceptable excipient. "Pharmaceutically acceptable" as used herein means that the compound or composition is suitable for administration to a subject to achieve the treatments described herein, without unduly deleterious side effects in light of the severity of the disease and necessity of the treatment. Exemplary excipients include, but are not limited to, a buffer and/or a buffering agent (e.g., an anion, a cation, an organic compound, a salt, etc.). Exemplary buffers include, but not limited to, carbonic acid/carbonate/bicarbonate-based buffers, disodium hydrogen phthalate/sodium dihydrogen orthophosphate-based buffers, tris (hydroxylmethyl) aminomethane/hydrochloric acid-based buffers, barbitone sodium/hydrochloric acid-based buffers, and any combination thereof. Exemplary buffering agents include, but are not limited to, carbonic acid, carbonate, bicarbonate, disodium hydrogen phthalate, sodium dihydrogen orthophosphate, tris (hydroxylmethyl) aminomethane, hydrochloric acid, barbitone sodium, dissolved $CO_2$ (e.g., $CO_2$ formulated at a pH of greater than 6.6), and any combination thereof. In certain embodiments, saline comprises a bicarbonate buffer excipient, such as a bicarbonate anion ($HCO_3^-$). In some embodiments, hypertonic saline comprises sodium bicarbonate, sodium carbonate, carbonic acid, and/or dissolved $CO_2$ formulated at a pH of greater than 6.5. Additional ingredients can be included as desired depending upon the particular condition being treated, as discussed further below.

"Substantially dehydrate" as used herein with respect to airway epithelial cells refers to cellular dehydration sufficient to result in: (a) a loss of at least 5, 10, 15 or 20 percent of cell volume; (b) inhibition of the beat of cilia projecting from those cells by at least 20 or 40 percent; (c) a decrease in the ability of the dehydrated cells to donate water to, and thereby hydrate, their overlying airway surface liquid/mucus layer; and/or (d) produce pro-inflammatory states such as increased 1 L-8 secretion.

"Hydrate," "hydration," and grammatical variants thereof, as used herein, refers to bringing, placing, drawing and/or the like water onto an airway surface of a lung. In certain embodiments, hydration is enhanced by a method of the present invention. Hydration can be enhanced by (a) an increase in the cell volume of airway epithelial cells of at least about 1%, 5%, 10%, 15%, 20%, or more, (b) an increase in the beat of cilia projecting from airway epithelial cells by at least about 1%, 5%, 10%, 15%, 20%, or more, and/or (c) increasing the ability of the airway epithelial cells to donate water to, and thereby hydrate, their overlying airway surface liquid/mucus layer.

2. Active Agents

Embodiments of the invention contemplate a variety of medicaments that can be delivered as aerosols to the lungs including agents that (i) enhance or facilitate mucus clearance; (ii) have antimicrobial activity; (iii) have anti-inflammatory activity; (iv) or have bronchodilator activity. For agents with undesirable safety or tolerability properties due to high local or systemic concentration following bolus administration via nebulizer, administration by inhalation over the course of 8 to 24 hours or overnight to a patient via nasal cannula may improve the therapeutic index for such agents.

Exemplary Agents that Facilitate Mucus Clearance

Adequate mucus clearance (MC) is a crucial factor in the maintenance of normal airway health, is dependent on mucus rheology, airway hydration, and ciliary beat frequency (CBF). Abnormal mucus clearance is an important contributor to the phenotype of patients with chronic bronchitis due to environmental or genetic causes. Normal mucus clearance requires 1) adequate hydration of the airway surface and 2) an absence of strong adhesive interaction between the mucus and cell surface. Hydration is formally defined by the concentrations of mucins in the periciliary and mucus layers. Ion transport properties regulate the amount of salt and water (i.e. the solvent) and goblet cells and glands control the concentration of mucins on the airway surface. Both cystic fibrosis (CF) patients and subjects with chronic bronchitis associated with cigarette smoke exposure, i.e., COPD, exhibit increases in mucus concentration as quantified by % solids, as a result of reduced airway hydration and mucin hypersecretion, consequent to goblet cell and glandular hyperplasia. Both as a function of disease severity, and in acute exacerbations, raised mucin/mucus concentrations produce adherent mucus that sticks to epithelial cells, initiates inflammatory responses and airway wall injury, and serves as a growth medium for pathogenic microorganisms (Boucher, R. C. New concepts of the pathogenesis of cystic fibrosis lung disease. European Respiratory Journal, 2004, 23(1):146-158 and Matsui, H., Grubb, B. R., Tarran, A., Randell, S. H., Gatzy, J. T., Davis, C. W., and Boucher, R. C. 1998. Evidence for periciliary liquid layer depletion, not abnormal ion composition, in the pathogenesis of cystic fibrosis airways disease. Cell 95:1005-1015 and Matsui, H., Wagner, V. E., Hill, D. B., Schwab, U. E., Rogers, T. D., Button, B., Taylor, R. M., 2nd, Superfine, R., Rubinstein, M., Iglewski, B. H., et al. 2006. A physical linkage between cystic fibrosis airway surface dehydration and *Pseudomonas aeruginosa* biofilms. Proc Natl Acad Sci USA 103:18131-18136).

A. Osmolytes.

A simple means to restore hydration to CF airway surfaces is to inhale hypertonic osmolyte solutions (most frequently 7% hypertonic saline (HS)), which draws water onto the airway surface. Rehydration of the lubricant periciliary layer (PCL) of the airway surface facilitates mucus clearance (MC) and, therefore, the removal of inhaled infectious agents.

Inhaled HS is a unique therapeutic agent as it is used by ~60% of CF patients nationwide, but is not FDA approved for daily use for pulmonary disease. As such, HS has not undergone the rigorous clinical testing to identify the dose and dosing frequency that are most efficacious and well tolerated. Instead, the HS regime has been optimized in practice by patients and physicians. Most commonly, HS is administered as two 15 minute inhalation treatments of 4 mL of 7% hypertonic saline per treatment. The tonicity of HS used by patients (7% NaCl) has been identified as a maximum concentration that is generally tolerated (i.e. minimal irritation or broncho constriction). Treatments are generally administered by a jet nebulizer (i.e. PARI LC-STAR™ or PLUS™ nebulizers), which are used by patients for other nebulized medicines and are thus available and familiar. Twice daily treatments with HS are common as the time burden for two HS treatments (15 minutes per treatment, plus nebulizer cleaning/sterilization), superimposed on the existing 2-3 hours per day spent on other therapies, is substantial.

TABLE 1

Comparison of Studies Administering Hypertonic Saline

|  | Donaldson et al.[a] | Elkins et al.[b] |
|---|---|---|
| Saline concentration | 7% | 7% |
| Device used | Pari LC Star | Pari LC Plus |
| Volume loaded into Nebulizer | 5 ml | 4 ml |
| Deposition Fraction | 18%[c] | 19.75%[d] |
| Aerosol Particle Size (MMAD) | 1.2-3.8 µm[e] | 2-4.1 µm[e] |
| Administrations per day | 4 | 2 |
| Maximum volume deposited in lung per day[f] | 3.6 ml | 1.58 ml |
| Maximum mass of NaCl deposited in lung per day[g] | 252 mg | 110.6 mg |
| FEV$_1$ Improvement at 14 or 28 days | 147 ml | ~68 ml[h] |

[a]Donaldson et al., N Engl J Med. 2006 Jan. 19; 354(3): 241-50.
[b]Elkins et al., N Engl J Med, 354(3): 229-40(2006).
[c]The deposition fraction was taken from the published work of Kellerman et al., Pulm Pharmacol Ther. 2008 August; 21(4): 600-7.
[d]The deposition fraction was taken from the published work of Byrne et al., Arch Dis Child, 2003 August; 88(8): 715-8.
[e]The aerosol particle size produced by the Pari LC Star and Plus have been reported variable in the literature and are cited as the range reported.
[f]The estimated volume delivered is an over-estimation as the nebulizer will have fluid remaining at the end of nebulization.
[g]The estimated mass of NaCl delivered is also an over-estimation as some fluid will remain in the nebulizer.
[h]The value presented is the FEV$_1$ after 48 weeks of delivery. It is the only value provided but from the FEV1 graph and as stated in the text, the values did not change appreciably from 2 weeks to the end of the study.

Recently, two studies have described (1) the short term (two weeks) beneficial effects of inhaled hypertonic saline (HS) four times daily on pulmonary function, MCC, and quality of life (Donaldson et al., N Engl J Med. 2006 Jan. 19; 354(3):241-50) and (2) the long term (one year) benefits of inhaled HS twice daily on lung function and reduction in pulmonary exacerbations (Elkins et al., *N Engl J Med*, 354(3):229-40(2006)). A comparison of the Donaldson versus Elkins suggests that the "more salt" delivered, the greater the benefit in lung function. As shown in Table 1, subjects in the Donaldson study exhibited a mean improvement in lung function (147 ml improvement in FEV1) with four times daily administration (3.6 ml of 7% HS predicted pulmonary deposition) that was ~2-fold greater than achieved in the Elkins study (~68 ml improvement in FEV1) with B.I.D. dosing (1.58 ml of 7% HS predicted pulmonary deposition). However, four times daily dosing in the Donaldson regimen is not feasible in the current treatment burden environment. Thus, there is reason to believe that the therapeutic benefit of HS has not been maximized. For example, while the Elkins study observed a significant decrease in pulmonary exacerbations for subjects on HS versus placebo, 59% of patients on HS still experienced an exacerbation, suggesting that improvements in adverse event prevention are also needed.

Administration of up to 12% HS has been evaluated previously (Robinson et al., *Thorax*, 1997 October; 52(10): 900-3). However, concentrations higher than 7% HS are not well tolerated with established methods of aerosol delivery. The currently used oral delivery of 7% HS aerosol by traditional jet nebulizers such as Pari LC Star is not tolerated by all CF patients with varying degrees of airway obstruction and reactive airway disease. Lack of tolerability of HS therapy can be related to high rates of emission of NaCl mass from the nebulizer mouthpiece which leads to high exposure of oropharyngeal surfaces to HS. Similarly, the high rates of NaCl mass deposition in the lung lead to adverse events such as chest tightness, cough and acute drops in lung function (Elkins et al.). In COPD, high rates of NaCl delivery initiate histamine release, which contributes to airway spasm (Taube et al., Am J Respir Crit Care Med. 2001 Nov. 15; 164(10 Pt 1):1810-5). On a cellular level, administration of high rate of NaCl mass to the airway epithelium substantially dehydrates the airway epithelial cells which leads to cell shrinkage, inhibition of ciliary beat frequency and release of inflammatory stimuli leading to pulmonary inflammation (Zhou et al., Journal of Cystic Fibrosis Vol. 10 Supplement 1, Page S18). Based on the measured nebulizer efficiency for Pari LC Star by Kellerman et al., the rate of emission of NaCl mass from the nebulizer and the rate of deposition of NaCl mass in the lung was determined for 7% HS administration administered by this jet nebulizer (Table 2).

With the increasing availability of high efficiency vibrating mesh nebulizers such as Pari eFlow, inhaled treatments for CF lung disease originally administered via jet nebulizers are now administered by these faster nebulizers. Based on the published efficiencies for Pari eFlow (Coates et al., J Aerosol Med Pulm Drug Deliv. 2011 June; 24(3):157-63), the rates of emission and pulmonary deposition of NaCl mass per unit of time are even higher for these high efficiency vibrating mesh nebulizers than for the jet nebulizers (Table 2).

TABLE 2

Comparison of Elkins et al., Donaldson et al. and the Method of This Invention: Rates of Mass Pulmonary Deposition of NaCl for Traditional Jet Nebulizers, Vibrating Mesh Nebulizers and Parion Device Used

| Reference | Elkins et al.; Kellerman et al. | Elkins et al., Coates et al. | Methods of This Invention | Methods of This Invention |
|---|---|---|---|---|
| Saline Concentration | 7% | 7% | 7% | 30% |
| Device Used | Pari LC Plus | Pari eFlow | Parion CSD-1 device | Parion CSD-1 device |
| Fill Volume | 4 ml | 2.5 ml | 29 ml[a] | 6.7 ml[a] |
| Time of Nebulization | 15 minutes | 4.8 minutes | 8 hours | 8 hours |
| Rate of Emission of NaCl Mass from Nebulizer | 11 mg/min[b] | 36 mg/min | 4.2 mg/min | 4.2 mg/min |
| Fractional Efficiency of Pulmonary Deposition | 0.18 | 0.38 | For example, 0.05 | For example, 0.05 |

TABLE 2-continued

Comparison of Elkins et al., Donaldson et al. and the Method of This Invention: Rates of Mass Pulmonary Deposition of NaCl for Traditional Jet Nebulizers, Vibrating Mesh Nebulizers and Parion Device Used

| Reference | Elkins et al.; Kellerman et al. | Elkins et al., Coates et al. | Methods of This Invention | Methods of This Invention |
|---|---|---|---|---|
| Deposited Pulmonary Dose | ~50 mg | ~67 mg | ~100 mg | ~100 mg |
| Rate of Deposition of NaCl Mass in the Lung | 3.4 mg/min | 14 mg/min | 0.21 mg/min | 0.21 mg/min |
| Dosing Frequency | BID | BID | QD | QD |
| Pulmonary dose per Day | ~100 mg | ~130 mg | ~100 mg | ~100 mg |

[a] Volume emitted from the nasal cannula
[b] Rate based on residual volume of 1.7 ml Additionally, using the methods of this invention enables administration of substantially larger mass of NaCl at lower rates into the lung of the patients, if desirable, over 6 to 8 hours while keeping the rates of deposition of NaCl mass in the lung below those for traditional jet or vibrating mesh nebulizers. This is beneficial based on the observation that ~250 mg of NaCl mass/day deposited in the lung of CF patients (Donaldson et al.) resulted in better efficacy than ~100 mg of NaCl mass/day deposited in the lung of CF patients (Elkins et al.) (Table 3).

Lastly, while administering aerosols through a nasal cannula to a subject, a certain amount of the aerosol deposits in the nasal passages. Administration of high concentrations of HS at low rates made possible by the methods of this invention are beneficial as they reduce the volume of aerosol deposited in the nasal passages of a patient.

The low rates for deposition of NaCl mass per unit of time in the lung achieved by the methods of this invention, combined with the higher mass of NaCl that can be deposited in the lung over 6 to 8 hours, lead to improved safety, tolerability and efficacy of HS. Furthermore, due to the low

TABLE 3

Comparison of Elkins et al. and the Method of This Invention: Increased Mass of NaCl Deposited in the Lung while Maintaining Low Rates of Deposition of NaCl Mass

| Reference | Elkins et al.; Kellerman et al. | Donaldson et al. | Methods of This Invention | Methods of This Invention |
|---|---|---|---|---|
| Saline Concentration | 7% | 7% | 7% | 30% |
| Device Used | Pari LC Plus | Pari LC Star | Parion device | Parion CSD-1 device |
| Fill Volume | 4 ml | 5 ml | 72 ml[a] | 17 ml[a] |
| Time of Nebulization | 15 minutes | ~18 minutes | 8 hours | 8 hours |
| Rate of Emission of NaCl Mass from Nebulizer | 11 mg/min[b] | ~11 mg/min | 11 mg/min | 11 mg/min |
| Fractional Efficiency of Pulmonary Deposition | 0.20 | 0.18 | For example, 0.05 | For example, 0.05 |
| Deposited Pulmonary Dose | ~50 mg | ~70 mg | ~250 mg | ~250 mg |
| Rate of Deposition of NaCl Mass in the Lung | 3.4 mg/min | ~3.4 mg/min | 0.53 mg/min | 0.53 mg/min |
| Dosing Frequency | BID | QID | QD | QD |
| Pulmonary dose per Day | ~100 mg | ~250 mg | ~250 mg | ~250 mg |

[a] Volume emitted from the nasal cannula
[b] Rate based on residual volume of 1.7 ml rates of NaCl mass emission from the nebulizer and the low rates of NaCl mass deposition in the lung, HS>7% can be administered by the methods of this invention with favorable safety, tolerability and efficacy profiles previously not achievable by traditional nebulizers.

The rate of the deposition of NaCl onto an airway surface reflects the product of the concentration of NaCl in the aerosol droplet and the droplet density. Both variables can be manipulated to achieve the desired "low" rates of NaCl deposition. For example, one way to achieve slower rates of HS deposition over extended periods of time is by using higher than 7% HS, such as 14% HS or 21% HS, emitted from the device at proportionally slower rates and consequently deposited in the airways at equal designated rates. Delivery of concentrations of HS formulation higher than 7 to 10% HS formulation is not possible via traditional methods of inhaled HS delivery, e.g. via Pari LC Star or eFlow, due to large number of adverse events experienced by the patients.

In practical terms, depending on the measured aerosol output from the CSD-1 device and the measured efficiency of the pulmonary deposition, the concentration of the HS drug product can be adjusted to produce desirable rates of NaCl mass deposition on the surface of the airways. Given the aerosol output characteristics of Parion CSD-1 device and likely in vivo deposition fractions, it may be desirable to nebulize 7, 14 and 21% HS to achieve a deposition rate of 0.1 to 4 mg/min. Note, given the low rates of aerosol presentation to the subject, the 0.5 mg/min deposition rate is still far less than achieved during nebulization of 7% HS in a Pari LC nebulizer—i.e. ~3.3 mg/min—and mimics that of normal saline delivered by Pari LC Star (~0.4 mg/min).

One skilled in the art will understand that the final rate of deposition of active pharmaceutical ingredient on the airway surface is the product of 1) the measured deposition efficiency for a given device in a given patient population (deposited dose/emitted dose from device); 2) the concentration of the active pharmaceutical ingredient the drug product (for example, 70 mg/ml of NaCl in 7% HS) and 3) the rate of emission of aerosol from the device (ml/min emitted from the device). The device deposition efficiencies can be measured via imaging of radiolabeled aerosols deposited in the lung of human subjects (Hyder et al., J Aersol Med 1985; 17:811-825). The output of an aerosol from an aerosol delivery device can be measured via direct capture of the aerosol on a filter. A variety of pharmaceutical formulation sciences and analytical methods can be used to formulate drug product and verify the concentration of the API.

One skilled in the art will understand that the osmotic driving force provided by the deposition of an osmolyte on the airway surface is dependent upon the molecular weight (MW) and number of osmoses per molecule (O/M) for any given osmolyte. Thus the low rates for deposition of mass per unit of time in the lung, provided herein for NaCl, can be easily transposed for other osmotic agents. For example, 6.25 mg of mannitol deposited per minute on the airways surface will create approximately the same osmotic driving force as 1 mg of NaCl deposited per minute as calculated below:

$$\frac{MW_{Mannitol} * O/M_{Mannitol}}{MW_{NaCl} * O/M_{NaCl}}$$

Active compounds of the present invention may be ionic osmolytes (i.e., salts), or may be non-ionic osmolytes (i.e., sugars, sugar alcohols, and organic osmolytes). It is specifically intended that both racemic forms of the active compounds that are racemic in nature are included in the group of active compounds that are useful in the present invention. It is to be noted that all racemates, enantiomers, diastereomers, tautomers, polymorphs and pseudopolymorphs and racemic mixtures of the osmotically active compounds are embraced by the present invention.

Active osmolytes useful in the present invention that are ionic osmolytes include any salt of a pharmaceutically acceptable anion and a pharmaceutically acceptable cation. Preferably, either (or both) of the anion and cation are non-absorbable (i.e., osmotically active and not subject to rapid active transport) in relation to the airway surfaces to which they are administered. Such compounds include but are not limited to anions and cations that are contained in FDA approved commercially marketed salts, see, e.g., Remington: The Science and Practice of Pharmacy, Vol. II, pg. 1457 (19.sup.th Ed. 1995), incorporated herein by reference, and can be used in any combination including their conventional combinations.

Pharmaceutically acceptable osmotically active anions that can be used to carry out the present invention include, but are not limited to, acetate, benzenesulfonate, benzoate, bicarbonate, bitartrate, bromide, calcium edetate, camsylate (camphorsulfonate), carbonate, chloride, citrate, dihydrochloride, edetate, edisylate (1,2-ethanedisulfonate), estolate (lauryl sulfate), esylate (1,2-ethanedisulfonate), fumarate, gluceptate, gluconate, glutamate, glycollylarsanilate (p-glycollamidophenylarsonate), hexylresorcinate, hydrabarnine (N,N'-Di(dehydroabietyl)ethylenediamine), hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, nitrte, pamoate (embonate), pantothenate, phosphate or diphosphate, polygalacturonate, salicylate, stearate, subacetate, succinate, sulfate, tannate, tartrate, teoclate (8-chlorotheophyllinate), triethiodide, bicarbonate, etc. Particularly preferred anions include chloride sulfate, nitrate, gluconate, iodide, bicarbonate, bromide, and phosphate.

Pharmaceutically acceptable cations that can be used to carry out the present invention include, but are not limited to, organic cations such as benzathine (N,N'-dibenzylethylenediamine), chloroprocaine, choline, diethanolamine, ethylenediamine, meglumine (N-methyl D-glucarnine), procaine, D-lysine, L-lysine, D-arginine, L-arginine, triethylammonium, N-methyl D-glycerol, and the like. Particularly preferred organic cations are 3-carbon, 4-carbon, 5-carbon and 6-carbon organic cations. Metallic cations useful in the practice of the present invention include but are not limited to aluminum, calcium, lithium, magnesium, potassium, sodium, zinc, iron, ammonium, and the like. Particularly preferred cations include sodium, potassium, choline, lithium, meglumine, D-lysine, ammonium, magnesium, and calcium.

Specific examples of osmotically active salts that may be used with the sodium channel blockers described herein to carry out the present invention include, but are not limited to, sodium chloride, potassium chloride, choline chloride, choline iodide, lithium chloride, meglumine chloride, L-lysine chloride, D-lysine chloride, ammonium chloride, potassium sulfate, potassium nitrate, potassium gluconate, potassium iodide, ferric chloride, ferrous chloride, potassium bromide, etc. Either a single salt or a combination of different osmotically active salts may be used to carry out the present invention. Combinations of different salts are preferred. When different salts are used, one of the anion or cation may be the same among the differing salts.

Osmotically active compounds of the present invention also include non-ionic osmolytes such as sugars, sugar-alcohols, and organic osmolytes. Sugars and sugar-alcohols useful in the practice of the present invention include but are not limited to 3-carbon sugars (e.g., glycerol, dihydroxyacetone); 4-carbon sugars (e.g., both the D and L forms of erythrose, threose, and erythrulose); 5-carbon sugars (e.g., both the D and L forms of ribose, arabinose, xylose, lyxose, psicose, fructose, sorbose, and tagatose); and 6-carbon sugars (e.g., both the D and L forms of altose, allose, glucose, mannose, gulose, idose, galactose, and talose, and the D and L forms of allo-heptulose, allo-hepulose, gluco-heptulose, manno-heptulose, gulo-heptulose, ido-heptulose, galacto-heptulose, talo-heptulose). Additional sugars useful in the practice of the present invention include raffinose, raffinose series oligosaccharides, and stachyose. Both the D and L forms of the reduced form of each sugar/sugar alcohol useful in the present invention are also active compounds within the scope of the invention. For example, glucose, when reduced, becomes sorbitol; within the scope of the invention, sorbitol and other reduced forms of sugar/sugar alcohols (e.g., mannitol, dulcitol, arabitol) are accordingly active compounds of the present invention.

Osmotically active compounds of the present invention additionally include the family of non-ionic osmolytes termed "organic osmolytes." The term "organic osmolytes" is generally used to refer to molecules used to control intracellular osmolality in the kidney. See e.g., J. S. Handler et al., Comp. Biochem. Physiol, 117, 301-306 (1997); M. Burg, Am. J. Physiol. 268, F983-F996 (1995), each incorporated herein by reference. Although the inventor does not wish to be bound to any particular theory of the invention, it appears that these organic osmolytes are useful in controlling extracellular volume on the airway/pulmonary surface. Organic osmolytes useful as active compounds in the present invention include but are not limited to three major classes of compounds: polyols (polyhydric alcohols), methylamines, and amino acids. The polyol organic osmolytes considered useful in the practice of this invention include, but are not limited to, inositol, myo-inositol, and sorbitol. The methylamine organic osmolytes useful in the practice of the invention include, but are not limited to, choline, betaine, carnitine (L-, D- and DL forms), phosphorylcholine, lyso-phosphorylcholine, glycerophosphorylcholine, creatine, and creatine phosphate. The amino acid organic osmolytes of the invention include, but are not limited to, the D- and L-forms of glycine, alanine, glutamine, glutamate, aspartate, proline and taurine. Additional osmolytes useful in the practice of the invention include tihulose and sarcosine. Mammalian organic osmolytes are preferred, with human organic osmolytes being most preferred. However, certain organic osmolytes are of bacterial, yeast, and marine animal origin, and these compounds are also useful active compounds within the scope of the present invention.

Under certain circumstances, an osmolyte precursor may be administered to the subject; accordingly, these compounds are also useful in the practice of the invention. The term "osmolyte precursor" as used herein refers to a compound which is converted into an osmolyte by a metabolic step, either catabolic or anabolic. The osmolyte precursors of this invention include, but are not limited to, glucose, glucose polymers, glycerol, choline, phosphatidylcholine, lyso-phosphatidylcholine and inorganic phosphates, which are precursors of polyols and methylamines. Precursors of amino acid osmolytes within the scope of this invention include proteins, peptides, and polyamino acids, which are hydrolyzed to yield osmolyte amino acids, and metabolic precursors which can be converted into osmolyte amino acids by a metabolic step such as transamination. For example, a precursor of the amino acid glutamine is poly-L-glutamine, and a precursor of glutamate is poly-L-glutamic acid.

Buffering Systems Used as Excipients to Prevent Decrease in Airway Surface pH for Diseases Associated with CFTR Dysfunction For the formulation of 7% and >7% hypertonic saline, formulations containing bicarbonate anions may be particularly useful, especially for respiratory disorders with CFTR dysfunction such as CF or COPD. There are two reasons for $HCO_3^-$ inclusion. First, recent findings indicate that, although the relative ratio of $HCO_3^-$ conductance/$Cl^-$ conductance is between 0.1 and 0.2 for single CFTR channels activated with cAMP and ATP, the ratio in the sweat duct can range from virtually 0 to almost 1.0, depending on conditions of stimulation. That is, combining cAMP+cGMP+α-ketoglutarate can yield CFTR $HCO_3^-$ conductance almost equal to that of $Cl^-$ conductance (Quiton et al, Physiology, Vol. 22, No. 3, 212-225, June 2007). Therefore, CF airways may be $HCO_3^-$ depleted, or acidic, and in need of replacement therapy. Absent CFTR-dependent bicarbonate secretion can also lead to impaired capacity of CF airways to respond to airway conditions associated with acidification of airway surface liquid layer, (Coakley et al., *Proc Natl Acad Sci USA*, 100(26):16083-8 (2003)).

Figure 49:
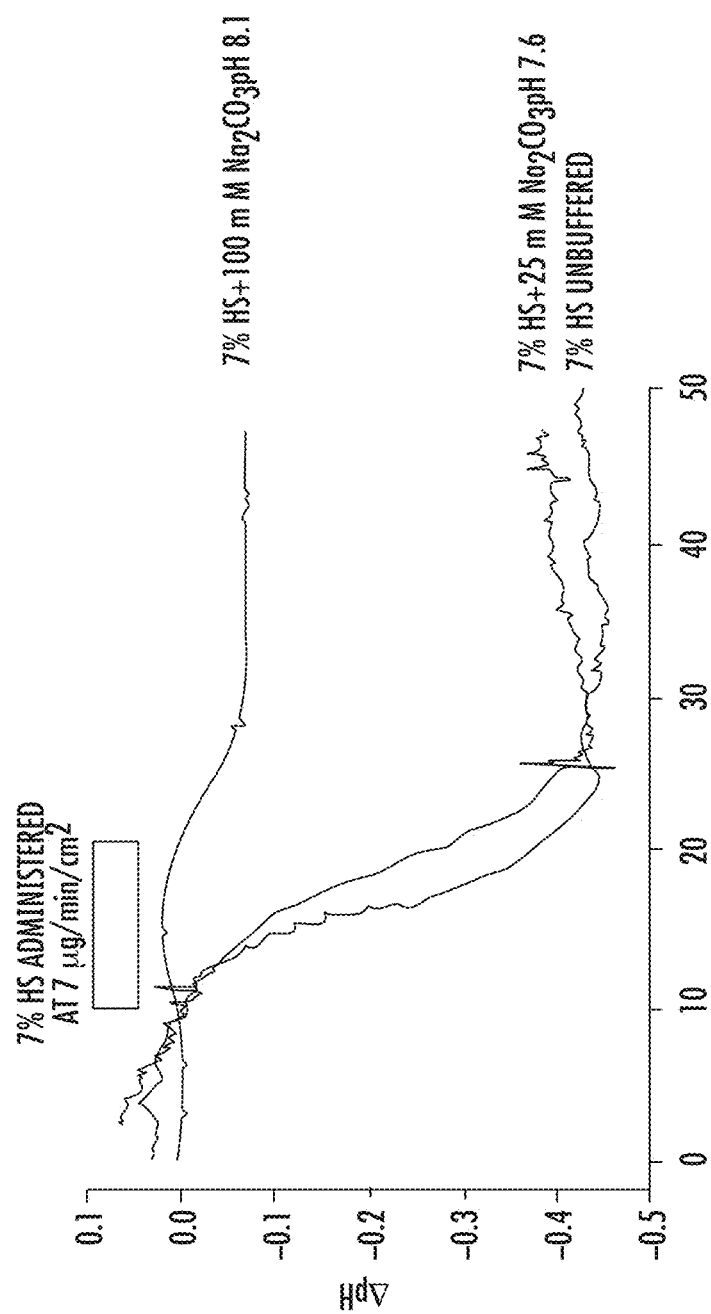
FIG. 49 shows a graph of the pH decrease following 7% HS administration onto the surface of the primary human bronchial epithelial cells from CF patients and the attenuation of such decrease via the use of buffering agents.

Buffering Systems Used as Excipients to Prevent Decrease in Airway Surface pH Following Hyperosmolar Agent Deposition in the Airways Administration of hyperosmolar agents, such as 7% HS, on the airway surface can cause a transient decrease in the pH of the airway surface liquid layer (ASL, FIG. 49). This transient decrease in pH may cause additional irritation to the airways. Therefore, it may be beneficial to co-formulate hyperosmolar agents with buffering excipients.

The hyperosmolar agents deposited as aerosols on the airway surface can cause an efflux of water from the airway epithelium. Effluxed water can rapidly equilibrate with atmospheric $CO_2$ gas [$CO_2(g) \rightarrow CO_2(l)$] which can rapidly form carbonic acid [$CO_2(l)+H_2O(l) \rightarrow H_2CO_3(l)$]. Subsequently, the carbonic acid can lower the pH of the ASL [$H_2CO_3(l) \rightarrow HCO_3^- + H_3O^+$]. To maintain the pH of the ASL, bicarbonate anions can be secreted from the airway epithelial cells via CFTR.

When a hyperosmolar agent is deposited on the airway surfaces at sufficiently high rates, which can cause rapid efflux of water onto the airway surface, the rapid equilibration of $CO_2$ in the ASL and the subsequent ASL acidification can exceed the rate of buffering ion secretion from the airway epithelia. Hence, a transient drop in pH can occur. This phenomenon may be exacerbated in human subjects with decreased CFTR function, such as in CF or COPD patients.

Formulations of hyperosmolar agents with buffering excipients of sufficient buffering capacities can be identified, so that the acidification of the ASL is attenuated or completely prevented. Exemplary buffer systems can comprise, but not limited to, carbonic acid/carbonate/bicarbonate-based buffers; disodium hydrogen phthalate/sodium dihydrogen orthophosphate-based buffers; tris (hydroxylmethyl) aminomethane/hydrochloric acid-based buffers; barbitone sodium/hydrochloric acid-based buffers; and any combination thereof.

Due to this evidence, inclusion of bicarbonate anion in the formulation of 7% or >7% hypertonic saline administered by the method of this invention would be particularly useful. Formulations containing up to 1 to 200 mM concentrations of bicarbonate anions are of particular interest for 7% or >7% HS solutions.

Also intended within the scope of this invention are chemically modified osmolytes or osmolyte precursors. Such chemical modifications involve linking to the osmolyte (or precursor) an additional chemical group which alters or enhances the effect of the osmolyte or osmolyte precursor (e.g., inhibits degradation of the osmolyte molecule). Such chemical modifications have been utilized with drugs or prodrugs and are known in the art. (See, for example, U.S. Pat. Nos. 4,479,932 and 4,540,564; Shek, E. et al., J. Med. Chem. 19:113-117 (1976); Bodor, N. et al., J. Phami, Sci. 67:1045-1050 (1978); Bodor, N. et al., J. Med. Chem. 26:313-318 (1983); Bodor, N. et al., J. Pharm. Sci. 75:29-35 (1986), each incorporated herein by reference.

Buffering Systems Used as Excipients to Prevent Decrease in Airway Surface pH Following Administrations of Acidic Aerosols Administration of large volumes of unbuffered aerosols on the airway surface can cause a transient decrease in the pH of the airway surface liquid layer (ASL). This transient decrease in pH may cause additional irritation to the airways. Therefore, it may be beneficial to co-formulate any aerosolized drug product with buffering excipients, providing sufficient maintenance of the pH of the aerosol in the neutral range and preventing decreases in the pH of the ASL upon aerosol deposition.

B. Sodium Channel Blockers

Coordinated ion transport by the airway epithelia directly regulates the hydration level of the mucosal surface. Importantly, sodium absorption through the epithelial sodium channel (ENaC) provides the rate-limiting step in hydration. In human subjects with loss of function mutation in ENaC have 'wet' airway surfaces and extraordinarily fast mucous clearance (see above) (Kerem et al., N Engl J Med. 1999 Jul. 15; 341(3):156-62). Conversely, increased sodium absorption through ENaC has been shown to be the underlying cause of mucous dehydration and the formation of mucous plugs in the lungs CF patients. Furthermore, transgenic mice that overexpress ENaC in the lungs have dehydrated airway surfaces and reduced/absent mucous clearance that results in death (Hummler et al., Proc Natl Acad Sci USA. 1997 Oct. 14; 94(21):11710-5). As predicted from clinical and experimental data, pharmacological blockade of ENaC conserves liquid on airway surfaces and increases mucus clearance (Hirsh et al., J Pharmacol Exp Ther. 2008; 325(1):77-88). Particular examples include, but are not limited to:

a. Small Molecule Channel Blockers:

Small molecule ENaC blockers are capable of directly preventing sodium transport through the ENaC channel pore. ENaC blocker that can be administered by the methods of this invention include, but are not limited to, amiloride, benzamil, phenamil, and amiloride analogues as exemplified by U.S. Pat. Nos. 6,858,614, 6,858,615, 6,903,105, 6,995,160, 7,026,325, 7,030,117,7,064,129, 7,186,833, 7,189,719, 7,192,958, 7,192,959, 7,241,766, 7,247,636, 7,247,637, 7,317,013 7,332,496, 7,345,044, 7,368,447, 7,368,450 7,368,451,7,375,107, 7,399,766, 7,410,968, 7,820,678, 7,842,697 , 7,868,010, and 7,875,619.

b. Protease Inhibitors:

ENaC proteolysis is well described to increase sodium transport through ENaC. Protease inhibitor block the activity of endogenous airway proteases, thereby preventing ENaC cleavage and activation. Protease that cleave ENaC include furin, meprin, matriptase, trypsin, channel associated proteases (CAPS), and neutrophil elastases. Protease inhibitors that can inhibit the proteolytic activity of these proteases that can be administered by the methods of this invention include, but are not limited to, camostat, prostasin, furin, aprotinin, leupeptin, and trypsin inhibitors.

c. Nucleic Acids and Small Interfering RNAs (siRNA):

Any suitable nucleic acid (or polynucleic acid) can be used to carry out the present invention, including but not limited to antisense oligonucleotide, siRNA, miRNA, miRNA mimic, antagomir, ribozyme, aptamer, and decoy oligonucleotide nucleic acids. See, e.g., US Patent Application Publication No. 20100316628. In general, such nucleic acids may be from 17 or 19 nucleotides in length, up to 23, 25 or 27 nucleotides in length, or more.

Any suitable siRNA active agent can be used to carry out the present invention. Examples include, but are not limited to, those described in U.S. Pat. No. 7,517,865 and US Patent Applications Nos. 20100215588; 20100316628; 20110008366; and 20110104255. In general, the siRNAs are from 17 or 19 nucleotides in length, up to 23, 25 or 27 nucleotides in length, or more.

C. Secretogogues

Mutations in the cystic fibrosis (CF) gene result in abnormal ion transport across the respiratory epithelium (Matsui et al., Cell 1998; 95:1005-15). Excessive absorption of sodium and the inability to secrete chloride by the airway epithelium in patients with CF drives water absorption down an osmotic gradient generated by inappropriate salt absorption, dehydrating airway mucous secretions and reducing the volume of liquid in the PCL. In COPD, cigarette smoke impairs CFTR function, thus creating an acquired phenotype similar to CF.

a. $P2Y_2$ Receptor Agonists:

Agents that that may be administered by the methods of the current invention include a group of $P2Y_2$ agonists. Purinergic ($P2Y_2$) receptors are abundant on luminal surface of human bronchial epithelium (HBE) and are known to stimulate $Cl^-$ secretion and inhibit $Na^+$ absorption (Goralski et al., Curr Opin Pharmacol. 2010 June; 10(3):294-9). UTP is an example of an endogenous $P2Y_2$ receptor agonist that provides a robust stimulation of chloride secretion, inhibition of sodium absorption and increase in airway surface liquid layer in airway epithelium, thus increasing the mucus clearance which is the primary defense mechanism of the lung. Early studies using uridine-5-triphosphate (UTP) delivered via aerosol to airway surfaces of CF and primary cilia dyskinesia (PCD) patients suggested the usefulness of UTP in enhancing MC and improving mean cough clearance rates.

However, UTP is rapidly degraded ($t_{1/2}$=~45 seconds) by extracellular enzymes lining the lumen of the lung or present as soluble forms in the airway surface liquid layer. Similarly, agents with low potency suffer from submaximal efficacy as they cannot be delivered in sufficient amount to the surface of the lung. Inhalation of such agents may require very frequent dosing regimen that may not be practical. For agents suffering from short half-lives or low potency, administration by inhalation over the course of 8 to 24 hours or overnight to a patient via nasal cannula improves the efficacy for such agents.

Native agonists of $P2Y_2$ receptor are susceptible to enzymatic hydrolysis in vivo by class of extracellular enzymes called ecto-nucleotidases (Lazarowski et al., J Biol Chem. 279(35):36855-64 (2004)) that are present on human epithelial surfaces. Consequently, these agonists have very short half-lives. Similarly, engineered nucleotide-based P2Y$_2$ agonists currently in clinical development are hydrolyzed on the surface of airway epithelium (Yerxa et al., J Pharmacol Exp Ther. 2002 September; 302(3):871-80) and are likely to have intermediate ($t_{1/2}$=~30 minutes) half-lives in vivo. Given the enzymatic degradation of native agonists as well as engineered nucleotide-based P2Y$_2$ agonists, ectonucleotidase inhibitors such as ebselen can be administered by the method of this invention in order to prolong half-lives of endogenous (eg ATP) or exogenously delivered P2Y$_2$ agonists.

Receptor desensitization, or decreased responsiveness of a receptor to agonist stimulation, represents a regulatory process with the potential to have a significant impact on cell behavior. P2Y(2), a G-protein-coupled receptor activated by extracellular nucleotides, undergoes desensitization at many tissues (Sanabria at al., Endothelium., 15(1):43-51 2008). Receptor desensitization has been linked to decreased clinical efficacy or duration of action of receptor agonists administered via inhalation. The extent of P2Y$_2$ receptor desensitization is dependent on agonist concentration and increases with the increasing concentrations of agonist. Administering high concentrations of P2Y$_2$ receptor agonist to produce effective concentrations of agonist for prolonged (hours) periods of time is likely to result in receptor desensitization and potentially decreased efficacy when such agonist is used as a therapeutic agent.

P2Y$_2$ agonists that can be administered by the methods of this invention include P2Y$_2$ receptor agonists such as ATP, UTP, UTP-γ-S and dinucleotide P2Y$_2$ receptor agonists (e.g. denufosol or diquafosol) or a pharmaceutically acceptable salt thereof. The P2Y$_2$ receptor agonist is typically included in an amount effective to stimulate chloride and water secretion by airway surfaces, particularly nasal airway surfaces.

A P2Y$_2$ receptor agonist denufosol failed to demonstrate clinical efficacy in a 48-week placebo-controlled study in CF patients when administered via rapid nebulization of 4 ml of 15 mg/ml solution of denufosol by Pari LC Star jet nebulizer three times a day. Such dosing regimen lead to a pulmonary deposition of ~36 mg of denufosol per day at rate of ~0.8 mg/min (~20% deposition efficiency of Pari LC jet nebulizer; three times a day ~15 minute nebulizations of 60 mg of denufosol in 4 ml of 15 mg/ml solution for inhalation). Deposition of denufosol on the surface of the lung according to the methods of the current invention at rates of 0.004 mg/min to 0.4 mg/min over extended 8 hour aerosol administration can allow for improved efficacy of denufosol. P2Y$_2$ agonists ATP, UTP, diquafosol and other P2Y$_2$ agonists with similar half-lives and potencies can be administered with improved efficacy at similar rates.

Suitable P2Y$_2$ receptor agonists are described in, but are not limited to, U.S. Pat. Nos. 6,264,975, 5,656,256, 5,292,498, 6,348,589, 6,818,629, 6,977,246, 7,223,744, 7,531,525 and U.S. Pat.AP.2009/0306009 each of which is incorporated herein by reference.

b. Activators of Alternative Chloride Channels Such as CaCCs and ClC-2 Class Channels:

CaCCs are broadly expressed in mammalian cells where they are involved in a wide range of physiological functions, including transepithelial fluid secretion, oocyte fertilization, olfactory and sensory signal transduction, smooth muscle contraction, and neuronal and cardiac excitation. Whole cell current analysis indicates several common features between CaCC subfamilies, including slow activation following membrane depolarization, outwardly rectifying steady state currents and greater iodide than chloride permeability. Single channel analysis has suggested four or more distinct CaCC subclasses, with a wide range of reported single channel conductances from less than 2 pS in cardiac myocytes to 50 pS in airway epithelial cells.

The consequences of CaCC activation are cell type specific, for example, chloride secretion in epithelial cells, action potential generation in olfactory receptor neurons, smooth muscle contraction, and prevention of polyspermia in oocytes. In some cell types, such as smooth muscle cells, membrane depolarization activates voltagegated calcium channels, increasing intracellular calcium concentration. Although CaCCs were functionally characterized nearly three decades ago, their molecular identity has remained unclear until recently, with potential candidates including bestrophins (BEST1-BEST4) (Sun et al., *Proc Natl Acad Sci USA* 99, 4008-4013 (2002) and Tsunenari et al., *J Biol Chem* 278, 41114-41125 (2003)), the calcium activated chloride channel ClCA family proteins (Gruber et al., *Genomics* 1998; 54:200-214) and ClC3 (Huang P et al, (2001) Regulation of human CLC-3 channels by multifunctional Ca2+/calmodulin-dependent protein kinase. JBC 276: 20093-100). Three independent laboratories have identified TMEM16A, also called anoctamin1, as a strong candidate for a CaCC (Yang Y D et al. (2008) TMEM16A confers receptor-activated calcium-dependent chloride conductance. *Nature*. 455: 1210-15; Caputo A et al. (2008) TMEM16A, a membrane protein associated with calcium-dependent chloride channel activity. *Science*. 322: 590-4; Schroeder B C et al. (2008) Expression cloning of TMEM16A as a calcium-activated chloride channel subunit. *Cell*. 134: 1019-29). Three different strategies were used: database searching for membrane proteins with multiple transmembrane segments and unknown function (Yang Y D et al. (2008) TMEM16A confers receptor-activated calcium-dependent chloride conductance. *Nature*. 455: 1210-15), functional genomics following the observation that interleukin 4 (Il4) treated bronchial epithelial cells show increased CaCC activity (Caputo A et al. (2008) TMEM16A, a membrane protein associated with calcium-dependent chloride channel activity. *Science*. 322: 590-4), and expression cloning using axolotl oocytes that do not have endogenous CaCC activity (Schroeder B C et al. (2008) Expression cloning of TMEM16A as a calcium-activated chloride channel subunit. *Cell*. 134: 1019-29). There is strong evidence to suggest TMEM16A is a key component of CaCC, including similarity to native CaCCs in its electrophysiological properties, appearance of CaCC currents in various transfected cell systems, reduction in CaCC currents following RNAi knockdown, and its tissue distribution. TMEM16A has eight putative transmembrane segments without domains evidently involved in calcium regulation.

ClC2 is a ubiquitously expressed, inwardly rectifying chloride channel that is activated by cell swelling. ClC2 was thought to be involved in cell volume regulation, but it has different biophysical characteristics from the volume sensitive chloride channels that have been characterized in many tissues. Suitable alternative chloride channel activators are described in U.S. Pat. Nos. 6,015,828, 6,159,969 and 7253295.

c. Modulators of CFTR Activity

The hereditary lethal disease cystic fibrosis is caused mutations in the gene encoding CFTR protein, a cAMP activated chloride channel expressed in the airway epithelia. Various mutations in CFTR cause ion transport dysfunction by limiting the chloride ion secretion to the surface of the airway epithelium via CFTR and by dys-regulation of sodium ion absorption, leading to excessive absorption of sodium cations. These defects in ion transport result in impaired hydration of airway surface liquid layer, decrease in mucus clearance and lead to progressive loss of lung function. Recently, it has been shown that CFTR functional defects are present in cigarette smoke exposed tissue, thus implying the role of CFTR dysfunction in COPD.

Over 1500 putative mutations have been described in CFTR, which can be divided into classes according to the molecular mechanism of the genetic defect (Rowe et al., Pulm Pharmacol Ther., 23(4):268-78 (2010)). An understanding of the biology of each of these mutations has led to therapeutic strategies based on the particular mutation type. Class I mutations include premature termination codons (PTCs, e.g. nonsense mutations) within the coding region of CFTR, which cause premature truncation of normal protein translation. These mutations are found in 10% of CF patients, but are particularly common in Ashkenazi Jews (75% of mutant CFTR alleles). Class II CFTR mutations include F508del CFTR, the most common mutation in humans (accounting for 75% of alleles and found in approximately 90% of CF patients). The deletion of phenylalanine at the 508 position causes CFTR to exhibit abnormal folding characterized by deficient stabilization by domain-domain interactions between the nucleotide binding domain 1 (NBD1) and the transmembrane domains. The misfolded protein is recognized by cellular chaperones within the endoplasmic reticulum (ER), directed to the proteasome, and rapidly degraded prior to reaching its active site at the cell surface. Because the cellular machinery responsible for the recognition and degradation of the misfolded protein is not 100% efficient, particular individuals exhibit low levels of surface expression of F508del CFTR, which may account for partial CFTR activity (and a more mild CF phenotype) observed in individuals homozygous for F508del CFTR, and could represent a population more amenable to protein repair. Even when at the cell surface, F508del CFTR exhibits reduced gating, suggesting that misfolded CFTR also exhibits reduced CFTR ion channel activity. Class III and IV CFTR mutations are characterized by full-length CFTR that reaches the cell surface but exhibit reduced ion transport activity owing to abnormal channel gating (Class III, e.g. G551D) or reduced conductivity of the ion channel pore (Class IV, e.g. R117H). Similarly, splicing mutants (Class V) and mutations within the C-terminus (Class VI) are also full length, but exhibit reduced activity owing to reduced numbers of active channels within the plasma membrane. Although the molecular basis of CFTR mutants is complex and as yet incomplete, the classification of CFTR mutants can be simplified into the therapeutically relevant groups based on the activity of agents in development. Both traditional and high-throughput drug discovery programs have resulted in discovery of novel compounds that address specific mutant CFTR alleles. These 'CFTR modulators' are pharmacological agents intended to repair the CFTR protein and are described in each section that follows.

Potentiators of cell-surface cystic fibrosis transmembrane conductance regulator CFTR mutation classes that result in dysfunctional CFTR that resides at the plasma membrane include Class III, IV, V, and VI mutations and represent potential targets for CFTR activators. G551D CFTR represents an archetype CFTR allele for this category of agents, as it exhibits normal surface expression and half-life, but confers a severe defect in channel gating owing to an amino acid substitution in the adenosine triphosphate (ATP) binding pocket within the nucleotide binding domains (Gregory, R. J. et al. (1991) Maturation and function of cystic fibrosis transmembrane conductance regulator variants bearing mutations in putative nucleotide-binding domains 1 and 2. *MCB* 11: 3886-93; Bompadre, S. G. et al. (2007) G551D and G1349D, two CF-associated mutations in the signature sequences of CFTR, exhibit distinct gating defects. *Gen Physiol*. 129: 285-298). Flavonoids are well known activators of mutant CFTR and were among the first to be studied for beneficial effects in human individuals (including topical administration). Although agents such as genistein were affected by lack of efficacy in the nasal airway, more recent efforts have demonstrated activity of the flavonoid quercetin in the nose. However, flavonoid agents are challenged by poor solubility and systemic absorption, and are poor development candidates for inhaled therapeutics. More recent discovery strategies have focused on identification of compounds that 'potentiate' CFTR activity, restoring endogenous regulation (e.g. cyclic adenosine monophosphate (cAMP)-dependent regulation) and ion transport without excessive, constitutive activation that may potentially be detrimental (such as excessive CFTR activation seen with certain diarrheal illnesses). Identification of agents of this type is amenable to high-throughput screening-based strategies to discover agents that activate mutant CFTR by measuring the effects on anion conductance in cell-based screening assays. A number of specific strategies have been used for screens of this sort, including chloride sensitive dyes, fluorescence resonance energy transfer-based analysis of membrane potential, and cell conductance of airway monolayers. Identification and characterization of small molecule potentiators of mutant CFTR have led to the development of agents with pronounced activity in vitro and in the clinic.

Significant effort has been directed toward the goal of correcting the folding of F508del CFTR, thus restoring ion channel activity to the misfolded protein. A diverse array of cellular targets have been explored, commensurate with the large number of proteins now known to interact with CFTR biogenesis. Agents such as 4-phenyl butyrate downregulate Hsc70 (or other cell chaperones) central to the folding process, and represent an early example of compounds tested in the clinic. Other more recent efforts have resulted from high-throughput library screens for chloride channel function following incubation of test compounds with F508del expressing cells. A number of these strategies have identified F508del correctors that may address cell biogenesis through chaperone pathways. Pharmacologic activity of such agents has also been reported to augment F508del CFTR half-life in the plasma membrane through altered surface recycling attributed to features of the cellular processing machinery or reduced endocytic trafficking. This class of agents may be potential drug development candidates if their safety in vivo is confirmed. Other compounds have been shown to directly interact with CFTR and may offer greater specificity than agents that alter general aspects of cell folding or cellular quality control. The global cellular response to misfolded protein may also represent a target. Histone deacetylases (HDAC) have far-ranging effects on gene expression, and specific members of the HDAC family are involved in the ER associated degradation pathway promoting degradation of F508del CFTR. Treatment of CF cells with HDAC inhibitors can modulate ER stress, and HDACs such as suberoylanilidehydroxamic acid, as well as siRNA-silencing of HDACs, increase levels of F508del CFTR in the cell membrane. The combination of approaches such as these reveal a number of potential pharmacologic agents for F508del correction. Additive or synergistic rescue of F508del CFTR using more than one such strategy may offer hope of achieving ion transport activity sufficient to confer a normal phenotype in CF respiratory epithelia.

Read-through of premature termination colons (PTCs) represents another exciting approach to address the underlying cause of CF, and many other genetic diseases caused by PTCs. Certain aminoglycosides and other agents have the capacity to interact with the eukaryotic rRNA within the ribosomal subunits. Although this interaction is much weaker than that seen in prokaryotes and is distinct from the primary cause of aminoglycoside toxicity in human individuals, it can modestly reduce the fidelity of eukaryotic translation by interrupting the normal proofreading function of the ribosome. Insertion of a near cognate amino acid at a premature stop codon allows protein translation to continue until one of several stop codons normally present at the end of the mRNA transcript is reached and properly utilized. The specificity of the strategy has been attributed to greater stop codon fidelity at the authentic end of mRNA and has been established in vitro by demonstrating no detectable elongation beyond native stop codons.

CFTR activity modulating compounds that can be administered by the methods of this invention include, but are not limited to, compounds described in US 2009/0246137 A1, US 2009/0253736 A1, US 2010/0227888 A1, U.S. Pat. No. 7,645,789, US 2009/0246820 A1, US 2009/0221597 A1, US 2010/0184739 A1, US 2010/0130547 A1, US 2010/0168094 A1, U.S. Pat. Nos. 7,553,855, U.S. Pat. No. 7,772,259 B2, U.S. Pat. No. 7,405,233 B2, US 2009/0203752, and U.S. Pat. No. 7,499,570.

D. Mucus/Mucin Modifying Agents a. Reducing Agents:

Mucin proteins are organized into high molecular weight polymers via the formation of covalent (disulfide) and non-covalent bonds. Disruption of the covalent bonds with reducing agents is a well-established method to reduce the viscoelastic properties of mucus in vitro and is predicted to minimize mucus adhesiveness and improve clearance in vivo. Reducing agents are well known to decrease mucus viscosity in vitro and commonly used as an aid to processing sputum samples (Hirsch, S. R., Zastrow, J. E., and Kory, R. C. Sputum liquefying agents: a comparative in vitro evaluation. *J. Lab. Clin. Med.* 1969. 74:346-353). Examples of reducing agents include sulfide containing molecules or phosphines capable of reducing protein di-sulfide bonds including, but not limited to, N-acetyl cysteine, N-acystelyn, carbocysteine, glutathione, dithiothreitol, thioredoxin containing proteins, and tris (2-carboxyethyl) phosphine.

N-acetyl cysteine (NAC) is approved for use in conjunction with chest physiotherapy to loosen viscid or thickened airway mucus. Clinical studies evaluating the effects of oral or inhaled NAC in CF and COPD have reported improvements in the rheologic properties of mucus and trends toward improvements in lung function and decreases in pulmonary exacerbations (Duijvestijn Y C M and Brand P L P. Systematic review of N-acetyleysteine in cystic fibrosis. Acta Peadiatr 88: 38-41. 1999). However, the preponderance of clinical data suggests that NAC is at best a marginally effective therapeutic agent for treating airway mucus obstruction when administered orally or by inhalation. A recent Cochrane review of the existing clinical literature on the use of NAC found no evidence to support the efficacy of NAC for CF (Nash E F, Stephenson A, Ratjen F, Tullis E. Nebulized and oral thiol derivatives for pulmonary disease in cystic fibrosis. Cochrane Database Syst Rev. 2009; 21(1): CD007168.). The marginal clinical benefit of NAC reflects:

The lack of a clear therapeutic benefit with NAC in clinical studies reflects the ineffectiveness of this molecule on the lung surface. Specifically, NAC does not possess the basic properties of an effective pulmonary drug as NAC (1) is a relatively inefficient reducing agent the airway surface environment (e.g. CF pH 6.5-7.2); and (2) is rapidly metabolized and cleared from the airway surface (Jayaraman S, Song Y, Vetrivel L, Shankar L, Verkman A S. Noninvasive in vivo fluorescence measurement of airway-surface liquid depth, salt concentration, and pH. J Clin Invest. 2001; 107(3):317-24). In more detail, due to its short half-life in the airway, very high concentrations of NAC (200 mM or 3.26%) are required to fully reduce Muc5B, a major gel-forming airway mucin, in vitro over short times representative of the NAC resident time on the surface of the airways following rapid administration via current jet neb or vibrating mesh technologies. In non-clinical studies, $^{14}$C-labled NAC, administered by inhalation, exhibits rapid elimination from the lungs with a half-life ranging from 6 to 36 minutes (unpublished observation). Furthermore, in the pH environment of the airway surface (measured in the range of pH 6.0 to 7.2 in CF and COPD airways), NAC exists only partially in its reactive state as a negatively charge thiolate (Jayaraman S, Song Y, Vetrivel L, Shankar L, Verkman A S. Noninvasive in vivo fluorescence measurement of airway-surface liquid depth, salt concentration, and pH. J Clin Invest. 2001; 107(3):317-24).

To overcome its modest activity, NAC is most commonly administered as a concentrated, hypertonic solution (Mucomyst® is a 20% or 1.27 M solution) via aerosol "bolus" (commonly a jet nebulizer with an ~20% pulmonary deposition fraction). Thus, a conventional 4 mL dose of 20% NAC leads to the pulmonary deposition of ~160 mg/dose at a rate of ~10.7 mg/min (~20% deposition efficiency of Pari LC jet nebulizer; once daily at ~15 minute nebulizations of 800 mg of NAC in 4 ml of 200 mg/ml solution for inhalation).

However, rapid aerosol delivery of concentrated NAC solutions impact the tolerability of NAC as it (1) possesses an unpleasant sulfur taste/odor; and (2) is associated with side effects including pulmonary irritation and bronchoconstriction which can require co-administration of rescue medications such as bronchodilators.

Administration of the NAC according to the methods of this invention allows an increase in the daily pulmonary dose (to increase efficacy), while decreasing the rate of presentation (to improve tolerability). Deposition of NAC on the surface of the lung according to the methods of the current invention can achieve this effect at rates of 0.005 mg/min to 5.4 mg/min over extended 8 hour aerosol administration can allow for improved efficacy of NAC. Furthermore, co-formulation of NAC with an excipient with buffering capacity to prevent pH decreases on the surface of the lung, as described by the methods of this invention, allows for further improvements in combined safety, tolerability or safety indices.

b. Surfactants:

Surfactants and detergents are spreading agents shown to decrease mucus viscoelasticity, improving mucus clearability. Examples of surfactants include DPPC, PF, palmitic acid, palmitoyl-oleoylphosphatidylglycerol, surfactant proteins (e.g. SP-A, B, or C), or may be animal derived (e.g. from cow or calf lung lavage or extracted from minced pig lung) or combinations thereof. See, e.g., U.S. Pat. Nos. 7,897,577; 5,876,970; 5,614,216; 5,100,806; and 4,312,860. Examples of surfactant products include Exosurf, Pumactant, KL-4, Venticute, Alveofact, Curosurf, Infasurf, and Survanta. Examples of detergents include, but are not limited to, Tween-80 and triton-X 100.

c. Expectorants:

Any suitable expectorant can be used, including but not limited to guaifenesin (see, e.g., U.S. Pat. No. 7,345,051).

d. DNase:

Any suitable deoxyribonuclease can be used, including but not limited to Dornase Alpha. (see, e.g., U.S. Pat. No. 7,482,024).

Exemplary Anti-Infective Agents

Chronic obstructive pulmonary diseases are accompanied by both acute and chronic bacterial infections. Both acute and chronic infections lead to chronic inflammation that has acute flare-ups in the form of pulmonary exacerbations. The underlying inflammation is treated with variety of inhaled anti-inflammatory agents. For example, in cystic fibrosis the most common bacteria causing chronic infection is *Pseudomonas aeruginosa* (*P. aeruginosa*) and antibiotics that are effective against this bacteria are a major component of treatment (Flume, Am J Respir Crit Care Med. 176(10): 957-69 (2007)). Also bacteria such as *Staphylococcus aureus* (*S. aureus*), *Burkholderia cepacia* (*B. cepacia*) and other gram negative organisms as well as anaerobes are isolated from respiratory secretions and people with CF may benefit from treatment of these pathogens to maintain their lung health. Anaerobic bacteria are also recognized as a feature of CF airways, sinuses in subjects with chronic sinusitis, and likely airways of subjects with COPD. Similarly, aspirations or microaspirations, especially in elderly population and during sleep, are associated with a chemical pneumonitis, anaerobic infections and subsequent bronchiectasis. An ideal treatment of aspiration-related pneumonitis and anaerobic infection would be an immediate treatment. As such, antibiotics are used to eradicate early infections, during pulmonary exacerbations and as chronic suppressive therapy.

The primary measure of antibiotic activity is the minimum inhibitory concentration (MIC). The MIC is the lowest concentration of an antibiotic that completely inhibits the growth of a microorganism in vitro. While the MIC is a good indicator of the potency of an antibiotic, it indicates nothing about the time course of antimicrobial activity. PK parameters quantify the lung tissue level time course of an antibiotic. The three pharmacokinetic parameters that are most important for evaluating antibiotic efficacy are the peak tissue level (Cmax), the trough level (Cmin), and the Area Under the tissue concentration time Curve (AUC), While these parameters quantify the tissue level time course, they do not describe the killing activity of an antibiotic.

Integrating the PK parameters with the MIC gives us three PK/PD parameters which quantify the activity of an antibiotic: the Peak/MIC ratio, the T>MIC, and the 24 h-AUC/MIC ratio. The Peak/MIC ratio is simply the Cpmax divided by the MIC. The T>MIC (time above MIC) is the percentage of a dosage interval in which the serum level exceeds the MIC. The 24 h-AUC/MIC ratio is determined by dividing the 24-hour-AUC by the MIC. The three pharmacodynamic properties of antibiotics that best describe killing activity are time-dependence, concentration-dependence, and persistent effects. The rate of killing is determined by either the length of time necessary to kill (time-dependent), or the effect of increasing concentrations (concentration-dependent). Persistent effects include the Post-Antibiotic Effect (PAE). PAE is the persistent suppression of bacterial growth following antibiotic exposure.

Using these parameters, antibiotics can be divided into 3 categories:

| Pattern of Activity | Antibiotics | Goal of Therapy | PK/PD Parameter |
|---|---|---|---|
| Type I Concentration-dependent killing and Prolonged persistent effects | Aminoglycosides Daptomycin Fluoroquinolones Ketolides | Maximize concentrations | 24 h-AUC/MIC Peak/MIC |
| Type II Time-dependent killing and Minimal persistent effects | Carbapenems Cephalosporins Erythromycin Linezolid Penicillins | Maximize duration of exposure | T > MIC |
| Type III Time-dependent killing and Moderate to prolonged persistent effects. | Azithromycin Clindamycin Oxazolidinones Tetracyclines Vancomycin | Maximize amount of drug | 24 h-AUC/MIC |

For Type I antibiotics (AG's, fluoroquinolones, daptomycin and the ketolides), the ideal dosing regimen would maximize concentration, because the higher the concentration, the more extensive and the faster is the degree of killing. Therefore, the 24 h-AUC/MIC ratio, and the Peak/MIC ratio are important predictors of antibiotic efficacy. For aminoglycosides, it is best to have a Peak/MIC ratio of at least 8-10 to prevent resistence. For fluoroquinolonesys gram negative bacteria, the optimal 24 h-AUCIMIC ratio is approximately 125. Versus gram positives, 40 appears to be optimal. However, the ideal 24 h-AUC/MIC ratio for FQ's varies widely in the literature.

Type II antibiotics (beta-lactams, clindamycin, erythromcyin, carbapenems and linezolid) demonstrate the complete opposite properties. The ideal dosing regimen for these antibiotics maximizes the duration of exposure. The T>MIC is the parameter that best correlates with efficacy. For beta-lactams and erythromycin, maximum killing is seen when the time above MIC is at least 70% of the dosing interval.

Type III antibiotics (vancomycin, tetracyclines, azithromycin, and the dalfopristin-quinupristin combination) have mixed properties, they have time-dependent killing and moderate persistent effects. The ideal dosing regimen for these antibiotics maximizes the amount of drug received. Therefore, the 24 h-AUC/MIC ratio is the parameter that correlates with efficacy. For vancomycin, a 24 h-AUC/MIC ratio of at least 125 is necessary.

Given the pharmacokinetic and pharmacodynamic properties for Type II and Type III antibiotics, administration by aerosol "infusion" will improve the efficacy for such agents. For example, carbapenam antibiotics are susceptible to enzymatic hydrolysis in vivo by the enzyme dehydropeptidase-I, thus leading to a short elimination half-life (less than 2 hr). The best measure of efficacy of this class of antibiotics is based on the minimum percentage of time the drug concentration is above the minimum inhibitory concentration (MIC) in the target tissue. Most dose regimens target a time above the MIC (TaM) of at least 50%, thus the need for a continuous infusion. High systemic concentrations of carbapenems can have proconvulsive effects and renal and liver toxicity.

Delivering carbapenems via continuous aerosol to the lungs of patients in need can allow for a safe and convenient way to maintain a high TaM in the lungs while reducing potential for systemic side effects. 500 mg to 2,000 mg of inhaled meropenem administered BID in 4 ml of normal saline via Pari LC jet nebulizers may be used for treatment of CF bacterial infections. Such administrations occur at a rate of 6.7 mg/min to 26.7 mg/min of meropenem deposited in the airway surface during two 15 minute nebulization periods per day. 20 mg to 1,200 mg dose of meropenem, deposited in the lung of CF patients per day and administered at a rate between 0.04 mg/min to 2.5 mg/min of meropenem deposited in the airway surface during 8 hour or longer extended aerosol administration according to method of this invention, can allow for better combined safety, tolerability and efficacy outcomes. Patients including, but not limited to, CF, COPD, non-CF bronchiectasis, aspiration pneumonia, asthma and VAP patients suffering from respiratory infection caused by bacteria susceptible to meropenem may benefit from such treatment. Examples of carbapenam antibiotics are: imipenam, panipenam, meropenam, doripenem, biapenam, MK-826, DA-1131, ER-35786, lenapenam, S-4661, CS-834 (prodrug of R-95867), KR-21056 (prodrug of KR-21012), L-084 (prodrug of LJC 11036) and CXA-101.

Delivering class III antibiotics via continuous aerosol to the lungs of patients in need can allow for a safe and convenient way to maintain a high 24 h-AUC/MIC in the lungs while reducing potential for systemic side effects. For example, 20 to 1,200 mg of vancomycin deposited in the lung of patients per day and administered at a rate between 0.04 mg/min to 2.5 mg/min of vancomycin deposited on the airway surface during 8 hour or longer extended aerosol administration according to method of this invention, can allow for better combined safety, tolerability and efficacy outcomes compared to rapid inhaled delivery or IV infusion. Patients including, but not limited to, CF, COPD, asthma, VAP, HAP, CAP patients and other patients suffering from respiratory infection caused by bacteria susceptible to vancomycin may benefit from such treatment.

The doses and rates for additional antibiotic agents benefiting from administration via aerosol inhalation over extended periods of time according to the methods of this invention are listed in Table 4 below. The rates of deposition of these antibiotic agents were optimized to maintain concentrations above MIC values for relevant bacterial strains and other relevant parameters such at time above MIC or 24-hour AUC/MIC where applicable.

Exemplary Anti-Inflammatory Agents

Inhaled corticosteroids are the standard of chronic care for asthma, COPD and other respiratory diseases characterized by acute and chronic inflammation leading to airflow limitation. Examples of corticosteroids suitable for administration by the method of this invention include beclomethasone, budesonide, and fluticasone. NSAIDs are a group of anti-inflammatory medications that do not contain steroids. NSAIDs do not carry the same risk of side effects as steroidal anti-inflammatory medications, but with long-term use, they may cause internal bleeding or kidney problems.

Products of arachidonic acid metabolism, specifically the leukotrienes (LTs), contribute to pulmonary inflammation. Cysteinylleukotrienes (LTC4, LTD4, and LTE4) are produced predominantly by eosinophils, mast cells, and macrophages. Examples of leukotriene modifiers suitable for administration by the method of this invention include monteleukastzileuton and zafirlukast.

Mast cell stabilizers are cromone medications such as cromolyn (sodium cromoglycate) used to prevent or control certain allergic disorders. They block a calcium channel essential for mast cell degranulation, stabilizing the cell and thereby preventing the release of histamine and related mediators. As inhalers they are used to treat asthma, as nasal sprays to treat hay fever (allergic rhinitis) and as eye drops for allergic conjunctivitis. Finally, in oral form they are used to treat the rare condition of mastocytosis.

PDE4 inhibitors have been shown to modulate pulmonary inflammation and used for treatment of chronic obstructive pulmonary diseases. Examples of PDE4 inhibitors suitable for administration by the method of this invention include theophylline and roflumilast.

Exemplary Bronchodilators a. NO, NO Donors, NO and Peroxynitrite Scavengers and Inducible NO Synthase Activity Modulators Nitric oxide (NO) is a potent endogenous vasodilator and bronchodilator that can be exogenously administered via inhalation. It is synthesized by the conversion of the terminal guanidine nitrogen atom of L-arginine via endothelial cell calcium dependent enzyme nitric oxide synthetase and then diffuses across the cell membrane to activate the enzyme guanylatecyclase. This enzyme enhances the synthesis of cyclic guanosine monophosphate (cGMP), causing relaxation of vascular and bronchial smooth muscle and vasodilatation of blood vessels (Palmer, Circ Res., 82(8):852-61 (1998)).

TABLE 4

Minimum and Maximum Doses Deposited in the Lung and Minimum and Maximum Rates of Antibiotic Deposition on the Airway Surface via CSD-1 Device

| Antibiotic | Deposited dose in the lung (mg/day) | CSD-1 rate of deposition (8 hours per day, mg/min) | CSD-1 rate of deposition normalized per constant 10 ml ASL volume (8 hours per day normalized per ASL volume: g/L ASL/hour) | CSD-1 rate of deposition normalized per constant 10 ml ASL volume (8 hours per day normalized per ASL volume: Mol/L ASL/Hour) |
|---|---|---|---|---|
| Vancomycin | 1200 | 2.50 | 15.00 | 1.01E−02 |
|  | 20 | 0.04 | 0.25 | 1.68E−04 |
| Meropenem | 1200 | 2.50 | 15.00 | 3.43E−02 |
|  | 20 | 0.04 | 0.25 | 5.71E−04 |
| Ertapenem | 200 | 0.42 | 2.50 | 5.26E−03 |
|  | 5 | 0.01 | 0.06 | 1.32E−04 |
| Doripenem | 300 | 0.63 | 3.75 | 8.93E−03 |
|  | 20 | 0.04 | 0.25 | 5.95E−04 |
| Imipenem | 800 | 1.67 | 10.00 | 3.15E−02 |
|  | 20 | 0.04 | 0.25 | 7.89E−04 |
| Linezolid | 360 | 0.75 | 4.50 | 1.34E−02 |
|  | 5 | 0.01 | 0.06 | 1.85E−04 |

Nitric oxide synthesised in endothelial cells that line blood vessels has a wide range of functions that are vital for maintaining a healthy respiratory and cardiovascular systems (Megson I L et al *Expert Opin Investig Drugs.* 2002 May; 11(5):587-601.). Reduced nitric oxide availability is implicated in the initiation and progression of many diseases and delivery of supplementary nitric oxide to help prevent disease progression is an attractive therapeutic option. Nitric oxide donor drugs represent a useful means of systemic nitric oxide delivery and organic nitrates have been used for many years as effective therapies for symptomatic relief from angina. However, nitrates have limitations and a number of alternative nitric oxide donor classes have emerged since the discovery that nitric oxide is a crucial biological mediator.

In the respiratory tract, NO is produced by residential and inflammatory cells (Ricciardolo F L et al. Curr Drug Targets 2006 June; 7(6):721-35). NO is generated via oxidation of L-arginine that is catalysed by the enzyme NO synthase (NOS). NOS exists in three distinct isoforms: neuronal NOS (nNOS), inducible NOS (iNOS), and endothelial NOS (eNOS). NO derived from the constitutive isoforms of NOS (nNOS and eNOS) and other NO-adduct molecules (nitrosothiols) are able to modulate bronchomotor tone. NO derived from the inducible isoform of NO synthase, up-regulated by different cytokines via NF-kappaB-dependent pathway, seems to be a pro-inflammatory mediator with immunomodulatory effects. In aging CF patients, expression of iNOS is significantly reduced (Yoon et al., J Clin Invest. 2006 February; 116(2):436-46). This reduced expression of iNOS in chronic CF is associated with emergence of mucoid muc mutant subpopulation of *P. aeruginosa*. It has been suggested that 15 mM $NO_2$ kills mucA P. *Aeruginosa* in CF airways at pH 6.5. NO itself or as a precursor to iron-nitrosyl species has been implicated in this antimicrobial effect. Therefore inhaled $NO_2^-$, including but not limited inhaled $NaNO_2$, has an appeal as a CF therapy. The production of NO under oxidative stress conditions secondarily generates strong oxidizing agents (reactive nitrogen species) that may amplify the inflammatory response in asthma and COPD. Moreover, NO can be exhaled and levels are abnormal in stable atopic asthma and during exacerbations in both asthma and COPD. Exhaled NO might therefore be a non-invasive tool to monitor the underlying inflammatory process. It is suggested that NOS regulation provides a novel target in the prevention and treatment of chronic inflammatory diseases of the airways such as asthma and COPD.

Examples of NO, NO donors and NO synthase activity modulators suitable for administration by the method of this invention include inhaled NO, agents disclosed in Vallance et al. *Fundam Clin Pharmacol.* 2003 February; 17(1):1-10, Al-Sa'doni H H et al. *Mini Rev Med Chem.* 2005 March; 5(3):247-54, Miller M R et al. *Br J Pharmacol.* 2007 June; 151(3):305-21. Epub 2007 Apr. 2 and Katsumi H et al. *Cardiovasc Hematol Agents Med Chem.* 2007 July; 5(3): 204-8.

Under certain conditions, inducible NO synthase activity leads to overproduction of NO which in turn increases inflammation and tissue injury. Under these conditions, the following inducible NO synthase inhibitors, NO scavengers and peroxynitrite scavengers administered by the methods of this invention are suitable: Bonnefous et al. *J. Med. Chem.*, 2009, 52 (9), pp 3047-3062, Muscara et al *AJP-GI* June 1999 vol. 276 no. 6 G1313-G1316 or Hansel et al. *FASEB Journal.* 2003; 17:1298-1300.

a. Beta 2-Adrenergic Receptor Agonists:

It has been established that administration of super-therapeutic concentrations of receptor agonists leads to receptor desensitization and loss of efficacy. For example, this phenomenon has been described for beta 2-adrenoceptor based bronchodilator agents (Duringer et al., Br J Pharmacol., 158(1):169-79 (2009)). High concentration of these receptor agonist agents leads to the receptor phosphorylation, internalization and potential degradation. Administration of receptor agonists, which cause tachyphylaxis following bolus administration via fast nebulizer, by inhalation over the course of 8 to 24 hours or overnight to a patient via nasal cannula improves the efficacy of such agents due to decreased extent of tachyphylaxis. Beta 2-adrenergic receptor agonsists include albuterol, levalbuterol, salbutamol, procaterol, terbutaline, pirbuterol, and metaproterenol Other Exemplary Therapeutic Agents Examples of other classes of therapeutic agents suitable for administration by the method of this invention include antivirals such as ribavirin, anti-fungal agents such as amphotericin, intraconazol and voriconazol, anti-rejection drugs such as cyclosporine, tacrolimus and sirolimus, bronchodilators including but not limited to anticholinergic agents such as atrovent, siRNAs, gene therapy vectors, aptamers, endothelin-receptor antagonists, alpha-1-antitrypsin and prostacyclins.

3. METHODS AND APPARATUS

Subjects or patients to be treated by the methods of the present invention include, but are not limited to, those afflicted or at risk of affliction with cystic fibrosis, chronic obstructive pulmonary disease (including chronic bronchitis and emphysema), non-cystic fibrosis bronchiectasis, primary ciliary dyskinesia, sinusitis, rhinosinusitis, nasal dehydration (e.g. due to inhalation administration of oxygen), asthma, emphysema, pneumonia (including ventilator-induced pneumonia and aspiration pneumonia), viral bronchiolitis, infectious agents (e.g., influenza, respiratory syncytial virus, *Pseudomonas aeruginosa, Burkholderiacepacia*, anthrax, etc. respiratory tract injury due to inhalation of dust, radioactive particles, infections agent, smoke, toxic or corrosive chemicals and/or irritants, etc.

A. Aerosol Administration.

To avoid undesired dehydration of airway epithelial cells, and/or achieve one or more other objects as described herein, nebulizers for administering aerosols for use in carrying out the present invention are preferably low output nebulizers (in contrast to the high output nebulizers such as the Westmed Heart High Output Nebulizer described in Boucher and Johnson, U.S. Patent Application Pub. No. 2009/0104272; and in contrast to the LC STAR™ pressure-driven aerosol nebulizer and the PART EFLOW™ ultrasonic nebulizer described in Boucher et al., Multiple Nebulizer System, U.S. Patent Application 20100074881 (published Mar. 25, 2010). A suitable low output nebulizer includes an aerosol delivery system as described in further detail below.

Exemplary Aerosol Delivery System

In some embodiments, an aerosol delivery system may be capable of maintaining steady aerosol output performance for extended periods of time (0.5 hours to 8 hours per day and up to 24 hours/day). Rainout and sputtering may be reduced over extended periods of treatment times, such as when a subject or patient is sleeping. As used herein, the term "rainout" refers to liquid from an aerosol that collects on a surface. Rainout may occur due to inertial impaction, gravitational sedimentation or condensation on a surface. "Sputtering" refers to rainout that exits from the device, e.g., from the nasal prongs of a nasal cannula. Rainout may reduce the aerosol output of the system, and sputtering may cause patient discomfort.

The aerosol delivery system may deliver an aerosol to the subject's nose via a nasal cannula for pulmonary delivery. In some embodiments, rainout may be reduced without substantially decreasing the aerosol output (volume output) of the system. A desired output may be achieved while limiting or reducing the rainout and sputtering. Accordingly, it may be desirable to employ extended aerosol administration overnight via a nasal cannula while the patient is asleep. Such extended aerosol administration would eliminate the daytime treatment burden presented with conventional bolus aerosol delivery treatments. Furthermore, such extended aerosol administration would enable improvement in efficacy, effectiveness, safety and tolerability for therapeutic agents benefiting from prolonged delivery at slower rates compared to bolus aerosol delivery.

As illustrated in FIGS. 1-4, an aerosol delivery system 10 includes a source of pulsatile or non-pulsatile gas flow, an entrainment chamber 20 and a particle selection chamber 40. The entrainment chamber 20 includes an aerosol generator 22, an aerosol inlet 24, an entrainment fluid inlet 26, an entrainment fluid outlet 28, and a rainout collection outlet or drain 30. The entrainment fluid outlet 28 includes a first end 28A and a second end 28B. The particle selection chamber 40 includes an impaction baffle 42, a particle selection chamber outlet 44 and a rainout collection outlet or drain 50. A fluid pathway 60 is generally defined by a fluid flowing from a source of pulsatile or non-pulsatile gas flow, through the inlet 26, through the entrainment chamber 20, out of the fluid outlet 28, into the particle selection chamber 40, around the baffle 42 and out of the outlet 44. The outlet 44 may be connected to a cannula (not shown), such as a nasal cannula for delivering aerosol to a subject. As shown in FIG. 2B, the delivery system 10 may be connected to a pump 130 and an optional compliance chamber 133. As shown in FIG. 2C, the delivery system 10 may be connected to a pump and an optional pulsed flow generator 134.

Figure 3:
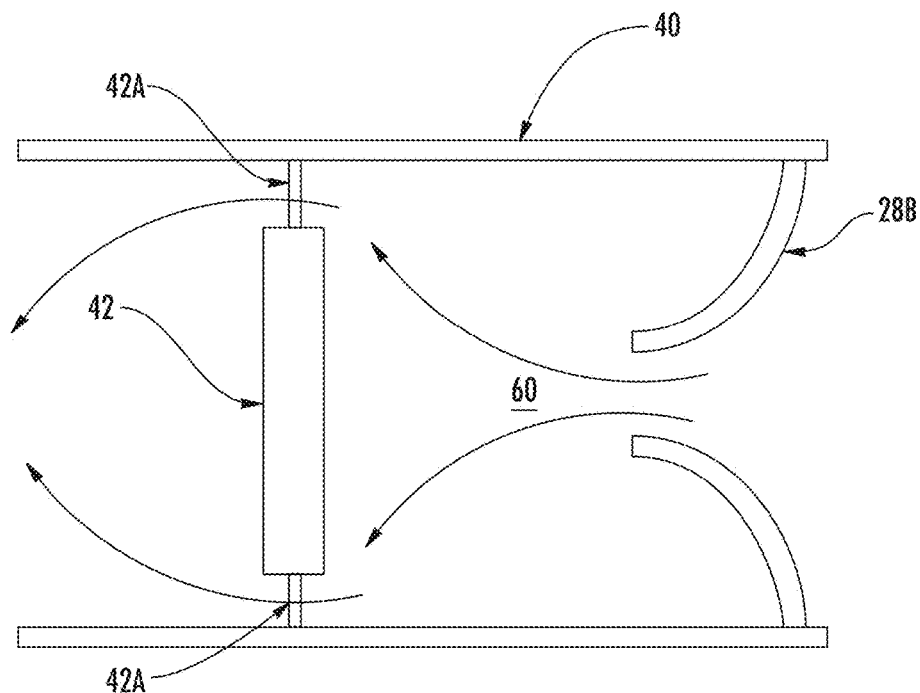
FIG. 3 is a cross-sectional side view of an impaction baffle in a particle selection chamber of the aerosol delivery system of FIG. 1.
Figure 4:
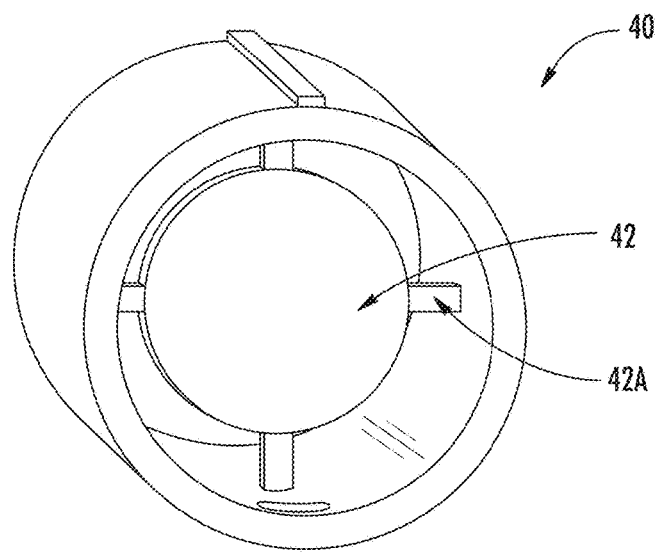
FIG. 4 is a perspective partially cut-away view of the impaction baffle of FIG. 3.

The aerosol generator 22 may be a nebulizer unit, such as a current jet nebulizer, ultrasonic nebulizer or vibrating mesh nebulizer that is configured to provide an aerosol to the entrainment chamber 20. Commercially available nebulizers include vibrating mesh nebulizers from Aerogen Aeroneb Lab, Pro and Solo, Pari eFlow vibrating mesh technologies, Omron's vibrating horn technologies, vibrating mesh or ultrasonic technologies from Phillips and other manufacturers. The fluid inlet 26 may be connected to a fluid source, such as an air or other gas source for providing an entrainment gas that flows into the entrainment chamber 20 and through the particle selection chamber 40 generally along the fluid pathway 60. The entrainment gas moves generally along the fluid pathway 60 and carries the aerosol from the aerosol generator 22 through the outlet 28, around the baffle 42 and out of the entrainment chamber outlet 44. As shown in FIGS. 3 and 4, the baffle 42 is held in position by supports 42A.

In this configuration, the aerosol generated by the generator 22 may include particles of a wide range of particle sizes. When the entrainment gas carries the aerosol though the outlet 28, the velocity of the gas increases because the first end 28A of the outlet 28 has a cross-sectional area that is larger than the cross-sectional area of the second end 28B. Such narrowing creates a nozzle or a jet which accelerates the movement of the aerosol particles towards the baffle. The diameter of the jet opening 28B can be tuned to achieve different velocities of aerosol particles and consequently increase or decrease the impaction of the aerosol particles on the baffle. The entrainment gas and aerosol is therefore directed toward the baffle 42 with an increased velocity. The baffle 42 is sized and configured such that larger aerosol particles will generally not be able to pass around the baffle 42 when the entrainment gas and aerosol is at a predetermined velocity. Accordingly, smaller aerosol particles may pass around the baffle 42 such that the resulting aerosol particles that pass out of the outlet 44 and into a nasal cannula are generally smaller than the aerosol particles in the entrainment chamber 20.

In some embodiments, the volumetric mean diameter (VMD) of the aerosol particles exiting the particle selection chamber is between 1 and 4 µm, and the percentage of the particles above 4 µm is less than 5%, less than 2% or less than 1% of the total particle volume emitted from the particle selection chamber 40 into the cannula. As used herein, the term "volumetric median diameter" or "VMD" is the particle size diameter such that half the mass of the aerosol particles is contained in particles with larger diameter and half is contained in a particles with smaller diameter. The flow rate entering the inlet 26 may be between 0.5 L/min to 5 L/min and more preferably between 1 and 3 L/min. The baffle 42 may be circular, although baffles may be provided that are spherical, triangular, rectangular, pentagonal, hexagonal, 6+n-gonal where n≥1 with the baffle mounted in cruciform or other suitable fashion. For flow rates between 1-5 L/min, the nozzle diameter is preferably between 0.5 to 5 mm in diameter. Nozzle diameters that are too small may prevent efficient cleaning of the device, and nozzle diameters that are too large may require too high an airflow for effective particle selection. High airflows may not be well tolerated by patients.

Figure 2A:
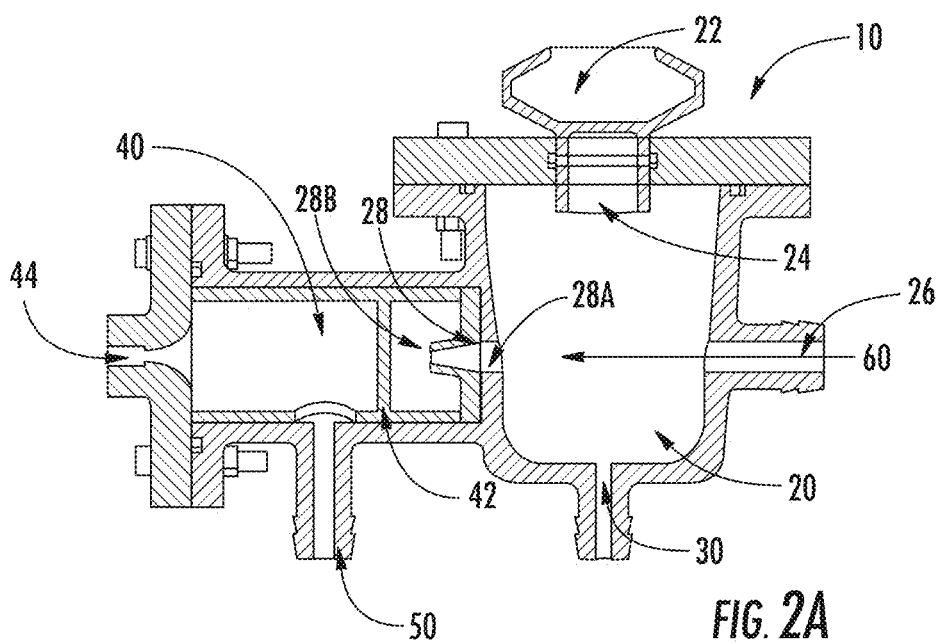
FIG. 2A is a cross-sectional side view of the aerosol delivery system of FIG. 1.
Figure 2B:
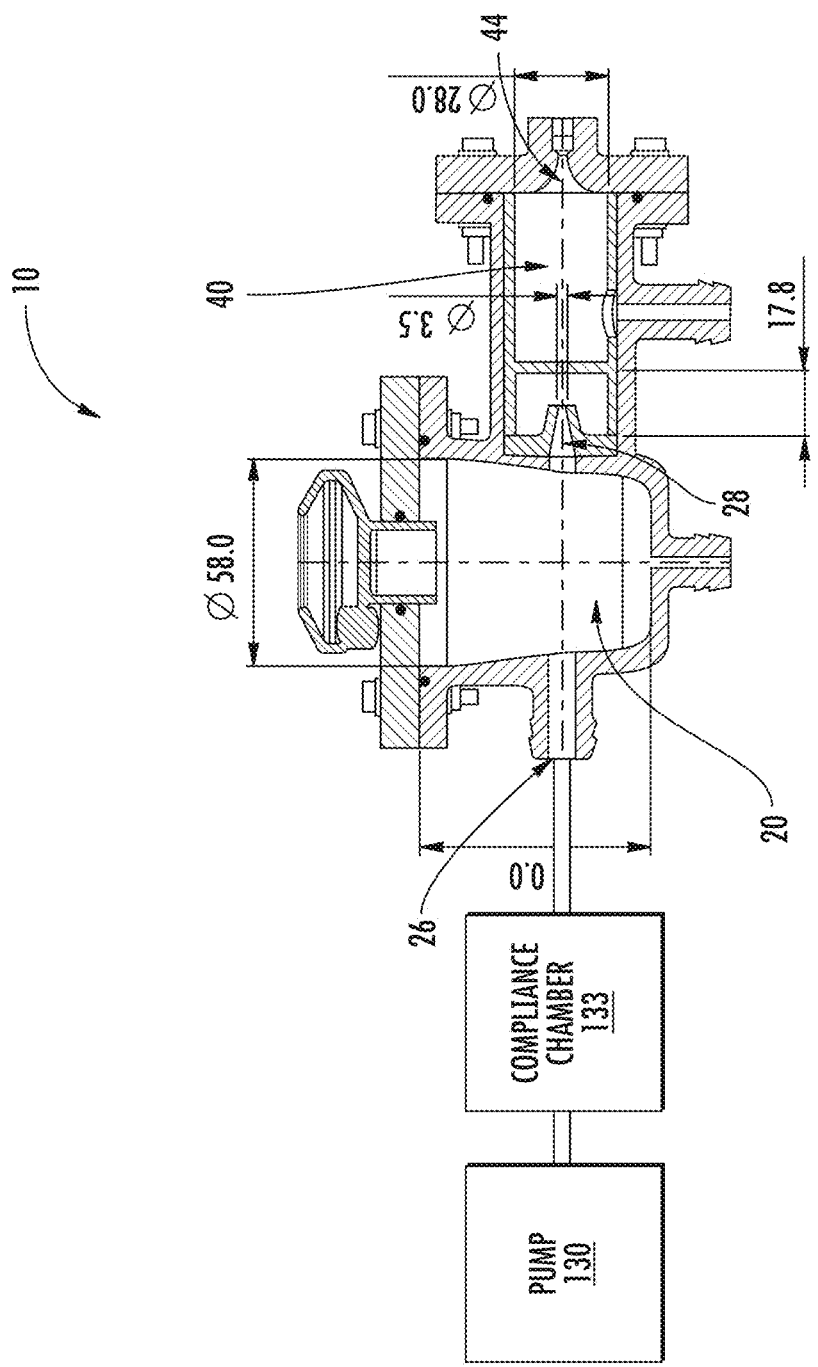
FIG. 2B illustrates the aerosol delivery system of FIGS. 1, 2A as coupled to a pump and compliance chamber.

As shown in FIG. 2B, the compliance chamber 133 may be used to produce an air source to the entrainment fluid inlet 26 that has a reduced amount of pressure or flow oscillations from the pump 130. The compliance chamber 133 may be a chamber of a size sufficient to reduce any flow oscillations from the pump 130. The optional compliance chamber 133 may be used to provide reproducible aerosols of a given particle size with adequate emitted volumes. In some embodiments, however, it may be desirable to use a pulsed air flow. Without wishing to be bound by any particular theory, it is currently believed that pulsatile entrainment fluids may provide even lower particle size selections, but corresponding lower emitted aerosol volumes, compared to non-pulsative entrainment fluids of the same average flow in 1 pms with all other factors such as nozzle diameter and baffle size and shape being equal. Accordingly, as shown in FIG. 2C, a pulsed flow generator 134 may be provided, such as a chamber or fluid pathway having a valve to provide reproducible, pulsed fluid flow to the entrainment fluid inlet 26.

In some embodiments, the volumetric mean diameter (VMD) of the aerosol may be reduced from about 6 µm out of the nebulizer less than about 2 µm as the aerosol exits the particle selection chamber outlet 44 and into, for example, a nasal cannula. In particular, the percentage of particles larger than 3 to 4 µm may be decreased. Since a large amount of aerosol volume and mass is located in these large particles, filtering out of large particles above certain size leads to decrease in the rate of aerosol emission (µl/min) and the rate of emission for the therapeutic agent contained in aerosol (mg/min). Table 5 displays a removal of large particle produced by Aerogen Aeroneb Pro nebulizer with 7% hypertonic saline drug product by a device 10 of this invention. While 75% of volume normalized particles had size above 4 µm for the standalone nebulizer, only 2% of volume normalized particles exiting port 44 of device 10 of this invention were larger than 4 µm. Filtering out of large particles led to a decrease in the aerosol output in terms of volume of aerosolized fluid contained in aerosol particles emitted from particle selection chamber outlet 44 per unit of time (µl/min). Additionally, the output of NaCl mass per unit of time (mg/min) from particle selection chamber outlet 44 decreased accordingly.

TABLE 5

Removal of Large Aerosol Particles by Device 10 in Support of Extended Aerosol Administration

|  | $DV_{50}$ (µm) | Output for Particles within 0.3-1 µm (%) | Output for Particles within 1-2 µm (%) | Output for Particles within 2-3 µm (%) | Output for Particles within 3-4 µm (%) | Output for Particles >4 µm (%) | Total Output % or µl/min |
|---|---|---|---|---|---|---|---|
| Standalone Nebulizer Aeroneb Pro | | | | | | | |
| Aerosol Volume output from nebulizer (µl/min) | 6.6 µm | 1%<br>6 µl/min | 5%<br>31 µl/min | 9%<br>55 µl/min | 10%<br>61 µl/min | 75%<br>458 µl/min | 100%<br>613.4 µl/min |
| NaCl mass output (mg/min)* | | 0.4 mg/min | 2.1 mg/min | 3.9 mg/min | 4.3 mg/min | 32.1 mg/min | 42.8 mg/min |
| Aeroneb Pro Nebulizer with Aerosol Delivery System 10 | | | | | | | |
| Aerosol volume output from port 44 (µl/min) | 1.6 µm | 17%<br>10 µl/min | 49%<br>28 µl/min | 23%<br>14 µl/min | 8%<br>4 µl/min | 2%<br>1 µl/min | 100%<br>58 µl/min |
| NaCl mass output from port 44 (mg/min)* | | 0.7 mg/min | 2.0 mg/min | 0.9 mg/min | 0.3 mg/min | 0.1 mg/min | 4 mg/min |

*7% hypertonic saline solution used

Figure 5:
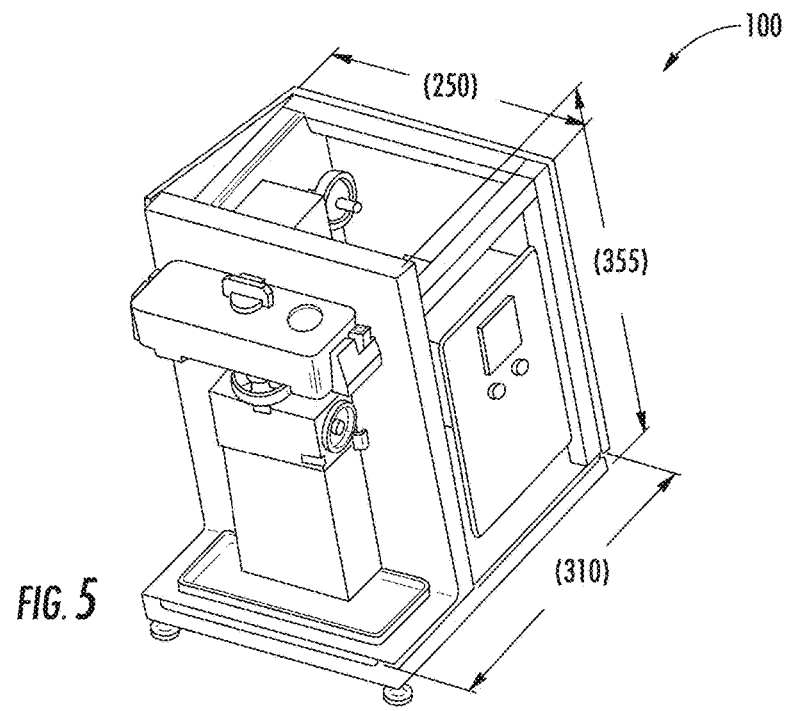
FIG. 5 is perspective view of an aerosol delivery unit for housing the aerosol delivery system of FIG. 1.
Figure 6:
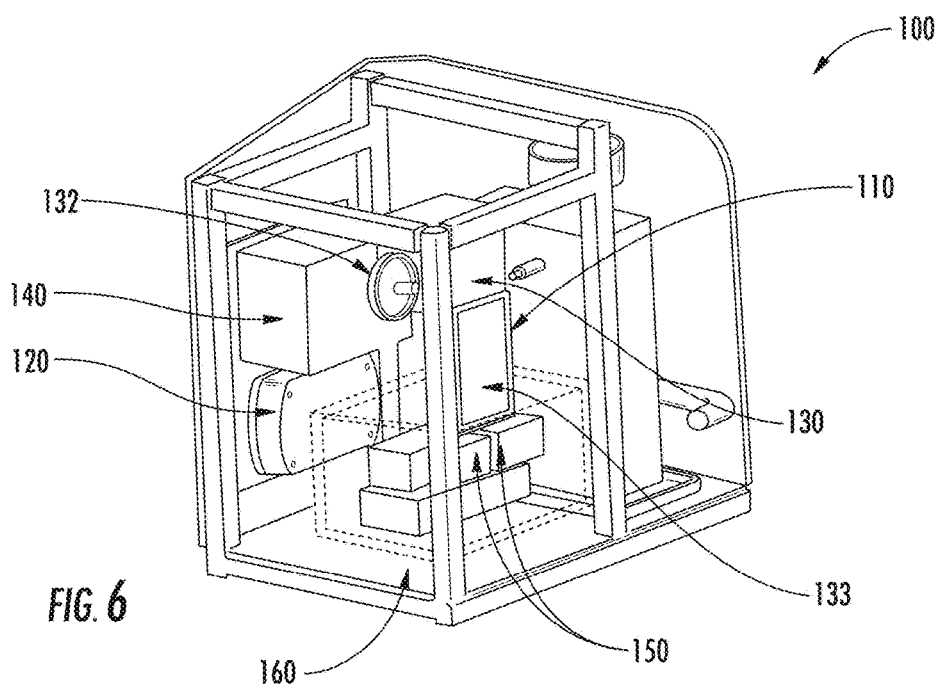
FIG. 6 is a cut-away perspective view of the aerosol delivery unit of FIG. 5.

As shown in FIGS. 5 and 6, the aerosol delivery system 10 may be positioned in a central region 110 of a container or aerosol delivery unit 100, which may include various auxiliary components for operating the aerosol delivery system 10. For example, the aerosol delivery unit 100 may include a nebulizer controller 120 for controlling the operation of the aerosol generator 22, an air pump 130, an optional compliance chamber 133 and a HEPA filter 132 for providing filtered air flow to the entrainment chamber inlet 24, an electronics unit 140 for enclosing electronics for controlling the operations of the pump 130 and other components of the unit 100, power supplies 150 for providing power to various components of the delivery unit 100 (such as the controller 120 and electronics unit 140), and a power switch 160 for turning the delivery unit 100 on or off.

In some embodiments, ambient air may be used as an entrainment fluid. The entrainment fluid may be dehumidified and/or dried compressed air, and/or oxygen (including low humidity oxygen).

In some embodiments, the impaction baffle is circular in shape while in others it is triangular, square, heptagonal, hexagonal or polygonal with n>6 vertexes, spherical, elliptical or otherwise optimized to provide a steep step function for particle selection.

In some embodiments, the tapered nozzle or jet connecting the aerosol entrainment chamber and the particle selection chamber is sized and configured to increase the velocity of the entrained aerosol and impact it into the baffle to reduce an amount of aerosol particles in the entrainment fluid that are greater than a predetermined diameter. The diameter of such a nozzle or jet facing the particle selection chamber is between 2 to 4 mm for airflow of entrainment fluid of 0.5 to 5 L/minutes.

In some embodiments, when the entrainment fluid exceeds 5 L/min, the diameter of the nozzle or a jet from the entrainment chamber to the particle selection chamber can be smaller than 2 mm. It should be understood that modifications to the nozzle diameter, flow rate and baffle dimensions may be interrelated and each contribute to the resulting aerosol and particle size distribution therein.

In some embodiments, the nasal cannula is heated. It should be understood that the cannula length, tubing diameter of the cannula, the bifurcation and the prongs may be sized and configured and/or matched to the aerosol output from the particle selection chamber in order to reduce rainout in the cannula while increasing the amount of aerosol emitted from the prongs expressed as a percentage of aerosol entering the cannula.

As illustrated in FIGS. 1-4, the fluid outlet 28 of the entrainment chamber 20 is configured to increase a velocity of the entrainment gas along the fluid pathway 60. However, it should be understood that, in some embodiments, the entrainment fluid pathway 60 and entrainment chamber 20 may be provided by alternative configurations. Embodiments according to the present invention will now be described with respect to the following non-limiting exemplary entrainment chambers are illustrated in FIGS. 7-13.

Figure 7:
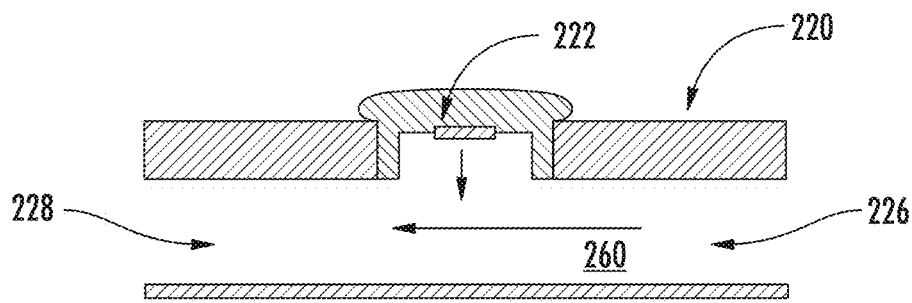
FIG. 7 is a cross-sectional side view of an entrainment chamber for aerosol delivery systems according to an embodiment of the invention.
Figure 8:
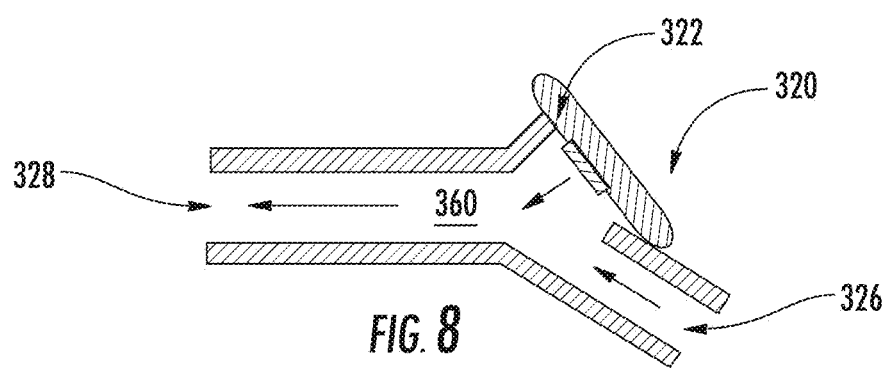
FIG. 8 is a cross-sectional side view of an entrainment chamber for aerosol delivery systems according to another embodiment of the invention.
Figure 9:
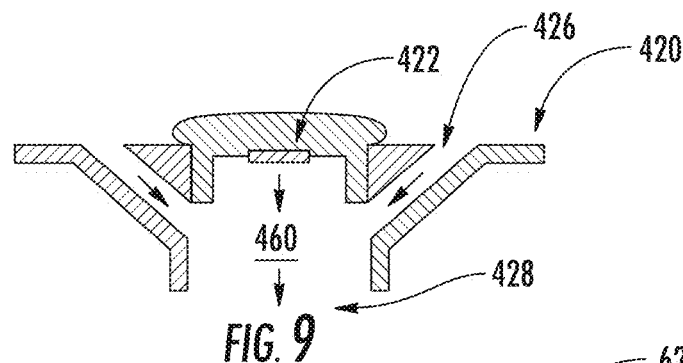
FIG. 9 is a cross-sectional side view of an entrainment chamber for aerosol delivery systems according to another embodiment of the invention.
Figure 10:
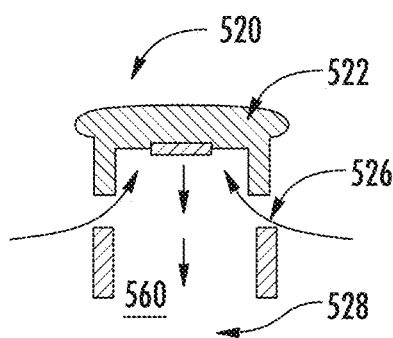
FIG. 10 is a cross-sectional side view of an entrainment chamber for aerosol delivery systems according to another embodiment of the invention.
Figure 11:
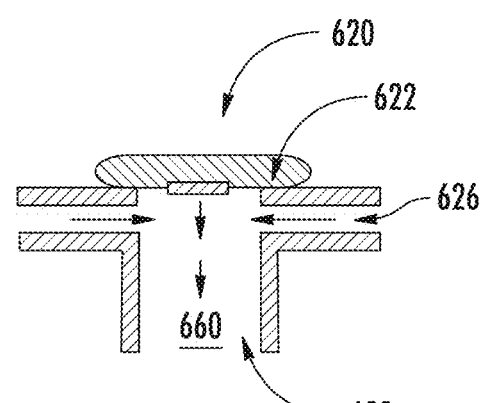
FIG. 11 is a cross-sectional side view of an entrainment chamber for aerosol delivery systems according to another embodiment of the invention.

As illustrated in FIG. 7, an entrainment chamber 220 having an aerosol generator 222, an inlet 226 and an outlet 228 that are configured to provide an entrainment fluid pathway 260. As illustrated in FIG. 7, the entrainment chamber 220 is configured as a generally straight passageway for providing a fluid flow or fluid pathway 260. As illustrated in FIG. 8, an entrainment chamber 320 includes an aerosol generator 322, an inlet 326 and an outlet 328 that provides an entrainment fluid pathway 360 and entrains the aerosol in an angle. As shown in FIG. 9, an entrainment chamber 420 includes an aerosol generator 422 and inlets 426 for providing a fluid flow entering in a downward direction from the sides of the chamber 420 to provide a downward fluid pathway 460 that exits at an outlet 428. As shown in FIG. 10, an entrainment chamber 520 includes an aerosol generator 522 and inlets 526 for providing a fluid flow entering in a upward direction from the sides of the chamber 520 to provide a downward fluid pathway 560 that exits at an outlet 528. As shown in FIG. 11, an entrainment chamber 620 includes an aerosol generator 622 and inlets 626 for providing a fluid flow entering at a generally perpendicular direction from the sides of the chamber 620 to provide a downward fluid pathway 660 that exits at an outlet 628.

Figure 12:
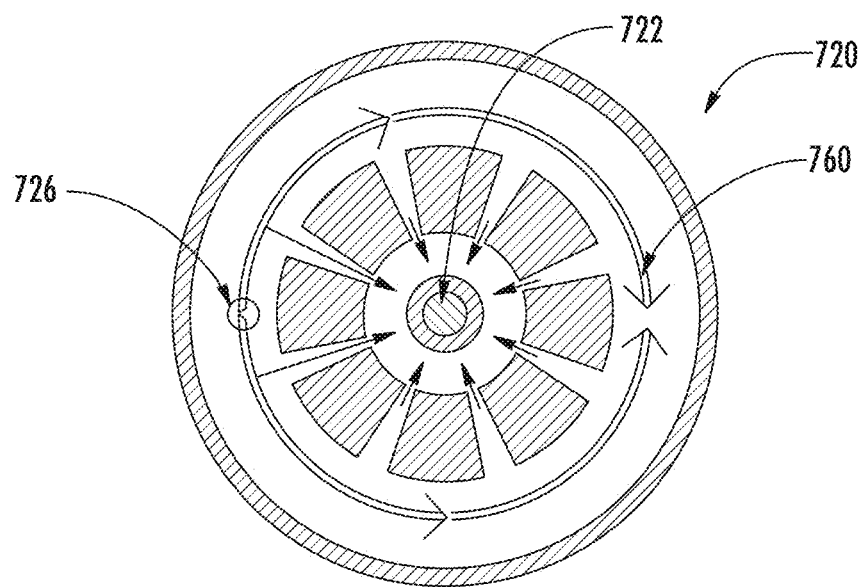
FIG. 12 is a top view of an entrainment chamber for aerosol delivery systems according to an embodiment of the invention.
Figure 13:
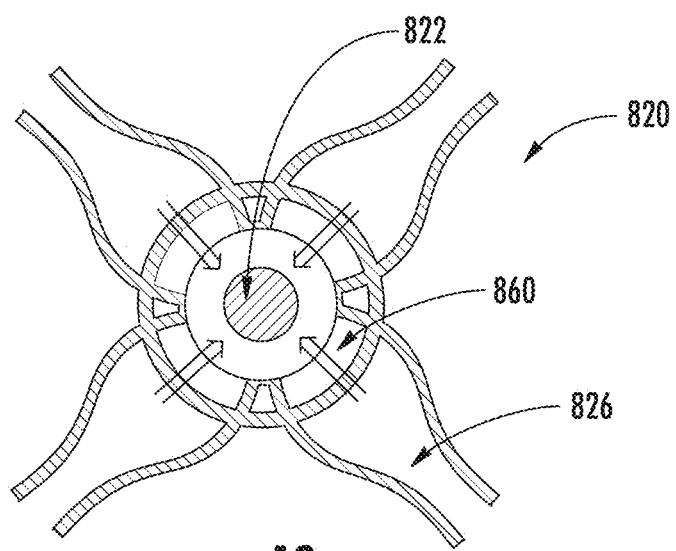
FIG. 13 is a top view of an entrainment chamber for aerosol delivery systems according to another embodiment of the invention.

Accordingly, as shown in FIGS. 9-11, the entrainment fluid may be provided by one or more inlets from the sides of the entrainment chamber adjacent the aerosol generator. In some embodiments as shown in FIG. 12, an entrainment chamber 720 with an aerosol generator 722 may include an inlet 726 that provides a generally circular fluid flow 760 that then enters a central region of the chamber 720 via channels 726A. The fluid flow 760 may then exit the chamber 720 in a direction away from the aerosol generator 722, for example, as illustrated in FIGS. 9-11. As shown in FIG. 13, an entrainment chamber 820 includes an aerosol generator 822 and a plurality of inlets 826 for providing a sideward fluid flow pathway 860 for entraining the aerosol therein. The fluid flow 860 may then exit the chamber 820 in a direction away from the aerosol generator 822, for example, as illustrated in FIGS. 9-11.

As illustrated in FIGS. 1-4, the combination of the appropriate airflow through the system from a source of pulsatile or non-pulsatile gas flow, baffle 42 and nozzle 28 combination of the particle selection chamber 40 is configured to selectively allow particles of a given size to travel around the baffle 42 and exit the chamber 40 via the outlet 44 into, for example, a nasal cannula. However, it should be understood that, in some embodiments, the entrainment fluid pathway 60 and entrainment chamber 20 may be provided by alternative configurations. Embodiments according to the present invention will now be described with respect to the following non-limiting exemplary particle selection chambers are illustrated in FIGS. 14-20.

Figure 14:
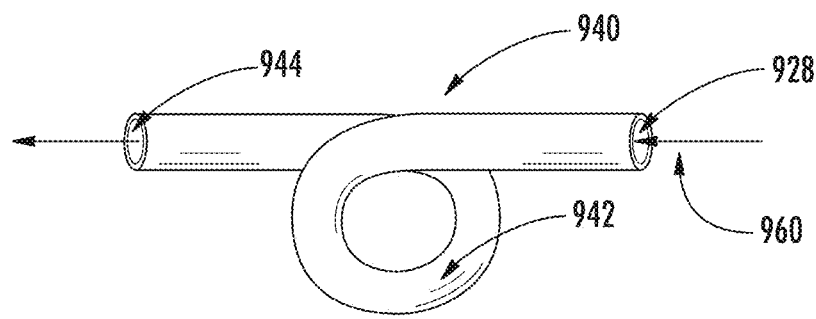
FIG. 14 is a perspective side view of a particle selection chamber for aerosol delivery systems according to some embodiments of the invention.
Figure 15:
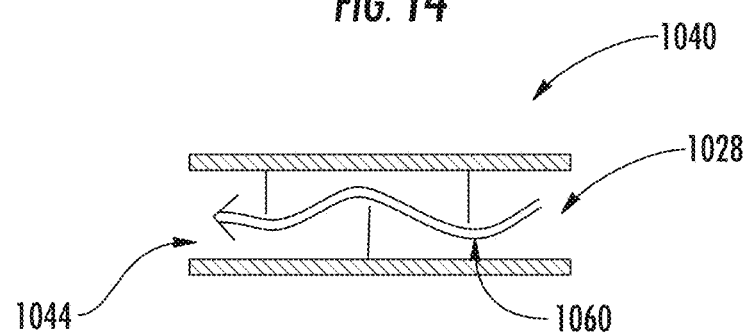
FIG. 15 is a cross-sectional side view of a particle selection chamber for aerosol delivery systems according to an embodiment of the invention.
Figure 16:
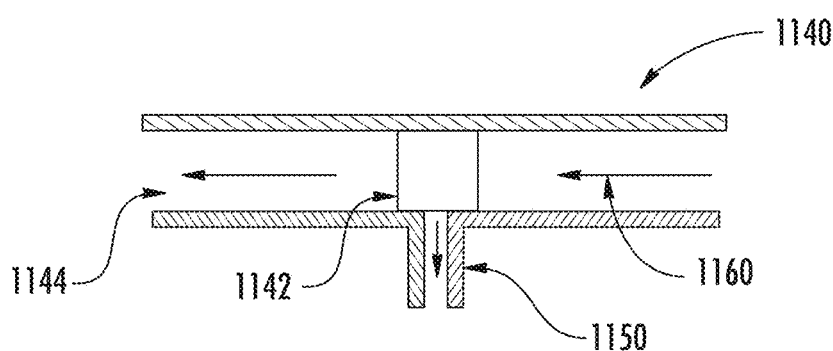
FIG. 16 is a cross-sectional side view of a particle selection chamber for aerosol delivery systems according to another embodiment of the invention.

In some embodiments, a particle selection chamber is configured to provide a non-linear entrainment fluid pathway that is configured such that aerosol particles having a larger particle size will rain out in the particle selection chamber. As illustrated in FIG. 14, a particle selection chamber 940 is provided as a generally tubular member that has an inlet 928 and an outlet 940 and a curved portion 942. Although the particle selection chamber 940 is illustrated with one curved portion 942, it should be understood that multiple loops may be provided. As illustrated in FIG. 15, a particle selection chamber 1040 includes an inlet 1028, an outlet 1044, and a plurality of baffles 1042 that provides a curvilinear fluid pathway 1060 by partially blocking a portion of the chamber 1040. Although the particle selection chamber 1040 is illustrated with three baffles 1042, it should be understood that any suitable number of baffles may be used. As illustrated in FIG. 16, a particle selection chamber 1140 includes an inlet 1128, an outlet 1144, and a particle or mesh filter 1142 that that traps particles of a given size in an entrainment fluid pathway 1160. The rain out or liquid aerosol particles from the filter 1142 then exit the chamber 1140 via a drain 1150.

Figures 17, 18:
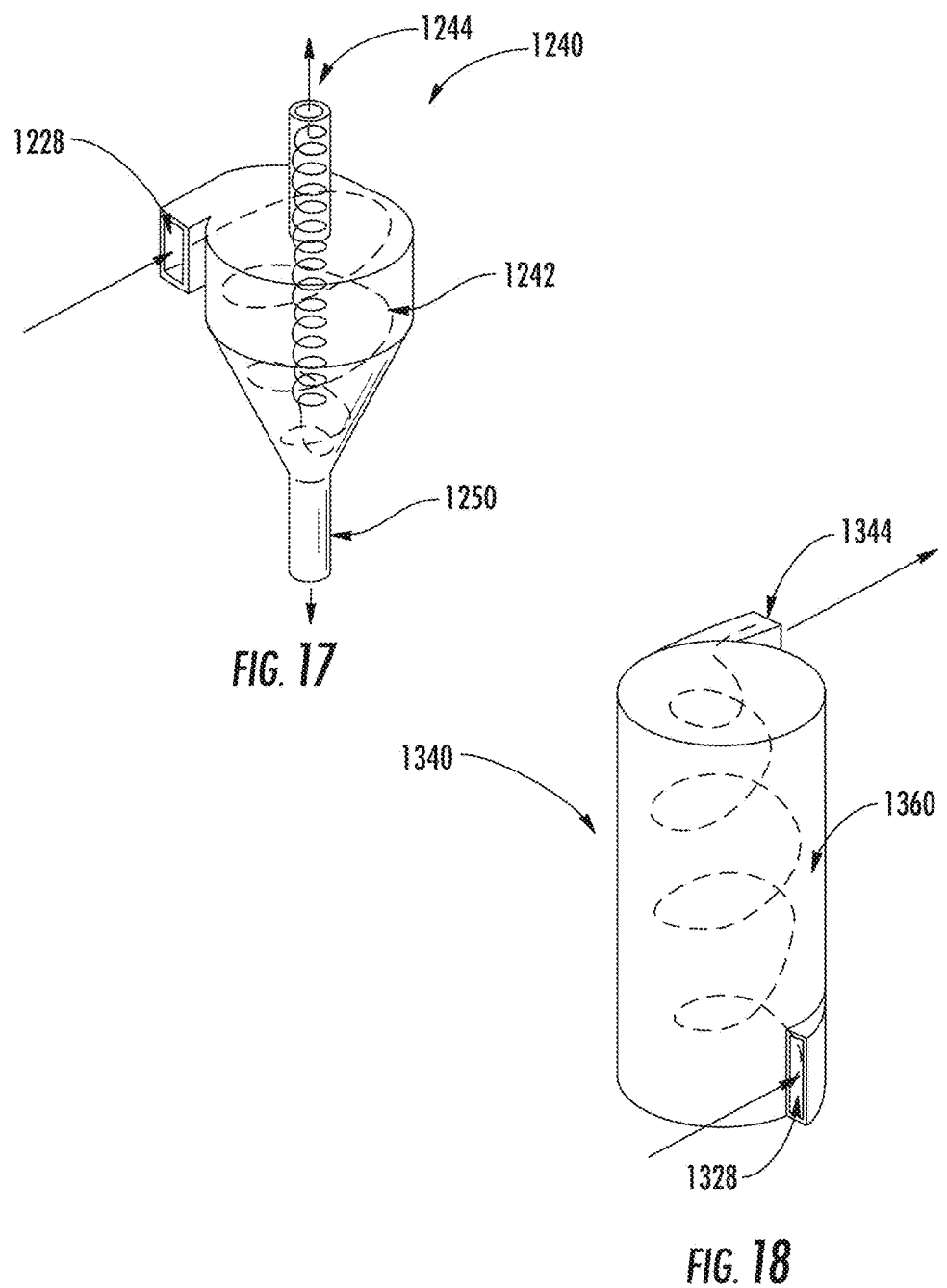
FIG. 17 is a perspective side view of a particle selection chamber for aerosol delivery systems according to an embodiment of the invention.
FIG. 18 is a perspective side view of a particle selection chamber for aerosol delivery systems according to another embodiment of the invention.

In some embodiments, non-linear fluid pathways may be provided by a particle selection chamber that is configured to create a generally circular or "cyclone" fluid flow. As illustrated in FIGS. 17 and 18, a "cyclone" passive filtration system is illustrated for removing larger aerosol droplets through centrifugal deposition. As illustrated in FIG. 17, a particle selection chamber 1240 includes an inlet 1228, an outlet 1244, a tapered body 1242 and a drain 1250. The curved body 1242 is configured to create the fluid pathway 1260, which spirals in a downward direction from the inlet 1228 to the drain 1250 and then spirals in an upward direction toward the outlet 1244. The radius of the downward direction of the pathway 1260 is generally greater than in the upward direction. As illustrated in FIG. 18, a particle selection chamber 1340 includes an inlet 1328 at one end and an outlet 1344 at the opposite end. The chamber 1340 is configured to provide a spiral-shaped fluid pathway 1360 through the cylindrical chamber 1340.

Figure 19:
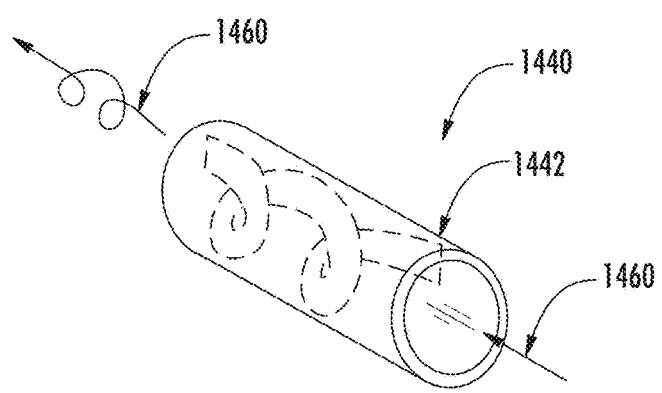
FIG. 19 is a perspective side view of a particle selection chamber for aerosol delivery systems according to an embodiment of the invention.
Figure 20:
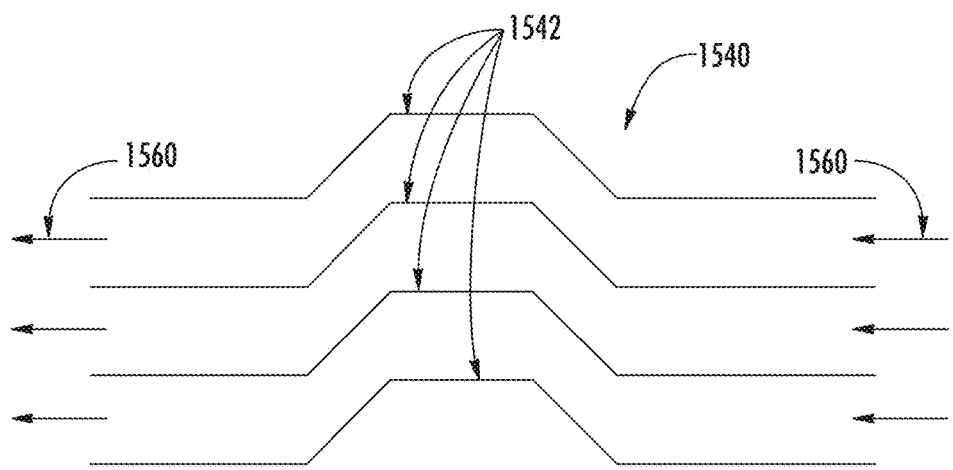
FIG. 20 is a cross-sectional side view of a particle selection chamber for aerosol delivery systems according to some embodiments of the invention.
Figure 21:
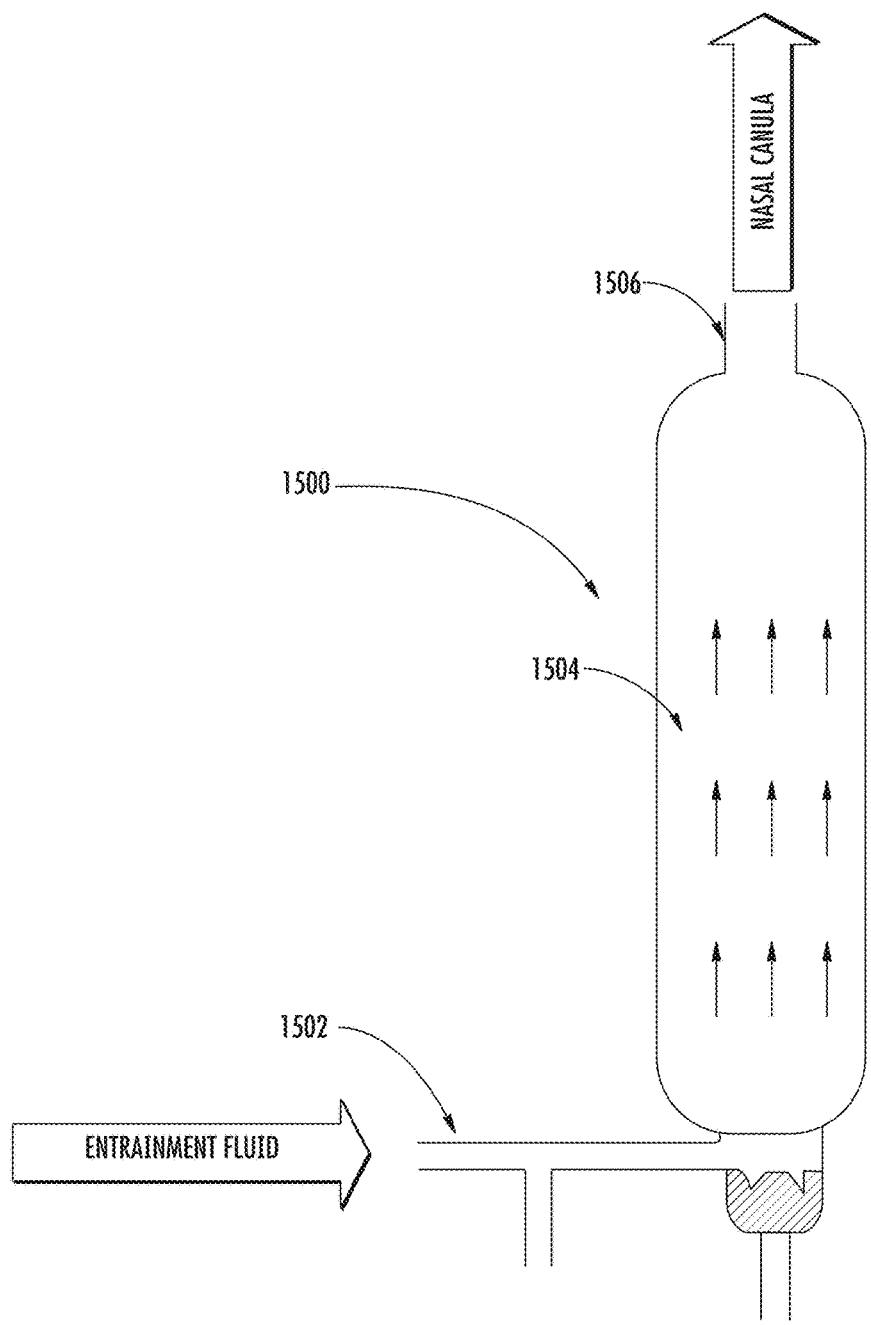
FIG. 21 is a cross-sectional side view of a particle selection chamber for aerosol delivery systems according to some embodiments of the invention.

In some embodiments, mechanical components may be used to provide a non-linear flow pathway in the particle selection chamber. As shown in FIG. 19, a cylindrical article selection chamber 1440 includes a spiral barrier 1442 that forms a spiral flow pathway 1460. As shown in FIG. 20, a particle selection chamber 1540 includes a plurality of nonlinear passageways 1542 for bending the flow pathway 1560. In some embodiments as shown in FIG. 21, particle selection occurs in the elutriator 1500. The elutriator 1500 includes an intake 1502 and a vertical body 1504 and an output 1506. The intake 1502 is connected to a nebulizer, and in the air elutriator body 1504, particles are ejected from a small fluidized bed into a flow of air and carried upwards. The air velocity may determine the particle size selection such that as the air velocity is increased, larger and larger particles are carried over.

a. Nasal Cannata

In some embodiments, nasal cannulas connected to the particle selection chamber are designed for their ability to conduct aerosols over extended periods of time at high aerosol output levels to reduce the rainout. The levels of aerosol output from the prongs of the cannula may preferably be sufficient to elicit a therapeutic benefit. Furthermore, the airflow via such cannulas may be in the range where it can be tolerated by patients over extended periods of time and generally lower than 5 L/min. Representative values for therapeutically relevant levels of output based on inhaled hypertonic saline example are discussed in the section b. Achieving Sufficient Output from the Prongs of Nasal Cannula During Aerosol Administration Over Extended Periods of Time An excessive rainout occurring in the cannula reduces the aerosol output from the prongs of the cannula to below therapeutic levels and causes patient irritating sputter when such fluid is ejected from the prongs of the nasal cannula into the patient's nose.

In some embodiments, the nasal cannulas are optimized to reduce gravitational sedimentation of the aerosol particles which in turn accumulates as rainout in the cannula, which may be achieved by increasing the diameter of the tubing used in the cannula and/or increasing the velocity at which the aerosol travels through the nasal cannula via an increase of airflow from 1 to 2 L/min to 3 to 4 L/min and higher.

In some embodiments, the nasal cannulas are optimized to reduce inertial impaction of the aerosol particles which in turn accumulate as rainout in the cannula, e.g., via reducing impaction at a bifurcation point of the supply tubing into face-piece tubing.

In some embodiments, the nasal cannulas are optimized to reduce inertial impaction of the aerosol particles which in turn accumulate as rainout in the cannula, e.g., via use of smooth bore tubing for supply tubing and face-piece tubing.

In some embodiments, the nasal cannulas are optimized to reduce inertial impaction of the aerosol particles which in turn accumulate as rainout in the cannula, e.g., via a single face-piece line entering into the face piece.

It should be understood that the balance between inertial impaction and gravitational sedimentation may be considered and/or optimized to achieve a minimal level of rainout.

In heated air CPAP systems without heated tubing, condensation contributes to additional rainout as the air is cooled in the tubing with subsequent condensation of the moisture on the wall of the tubing. In the embodiments of the current invention where heated air is not used, condensation is not a major contributor to rainout as ambient temperature gas is used and the temperature of the gas and the nasal cannula tubing is similar. In embodiments of this invention where heated air is used, condensation may contribute to rainout in the nasal cannulas and appropriate measures to control condensation may be employed.

Figure 31:
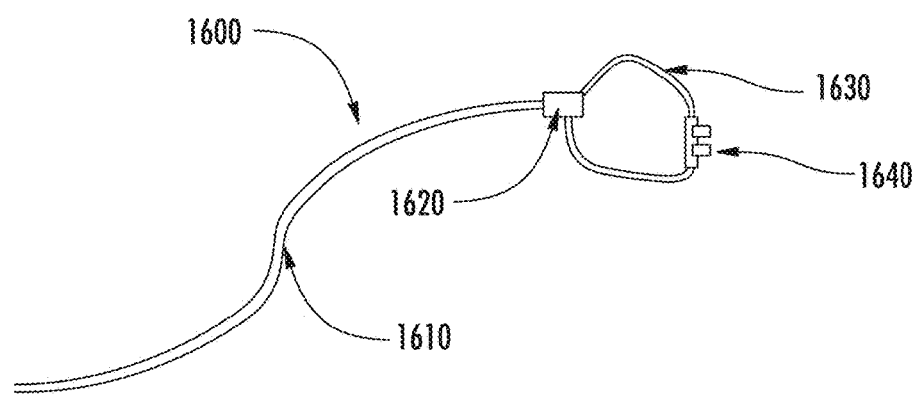
FIG. 31 is a conventional nasal cannula such as Salter HF1600.

A conventional nasal cannula 1600 is illustrated in FIG. 31. The nasal cannula 1600 includes supply tubing 1610, a bifurcation junction 1620, face-piece tubing 1630, and nasal prongs 1640. In the conventional cannula 1600, inertial impaction of an aerosol may occur, for example, at the bifurcation junction 1620 (where larger aerosol particles may impact and rainout during sharp curvature of the bifurcation junction 1620) and/or at the nasal prongs 1640 (where larger aerosol particles may impact and rainout at sharp curvature points in the nasal prongs 1640).

Figure 32:
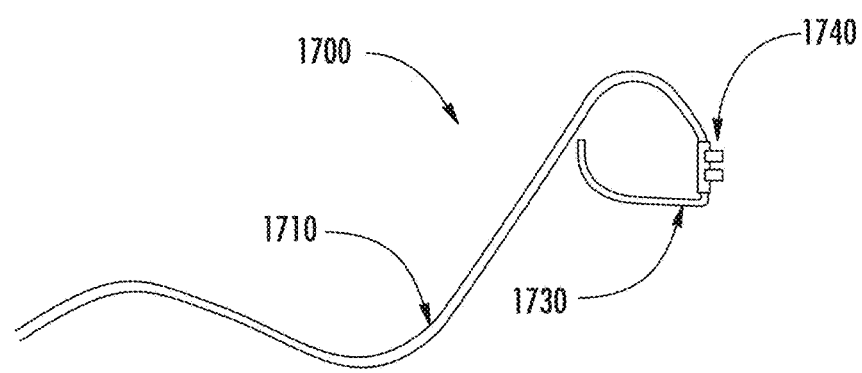
FIG. 32 is a nasal cannula configuration according to an embodiment of the present invention.

As illustrated in FIG. 32, reduced rainout may be achieved, for example, by eliminating the bifurcation junction and by using a single line of supply tubing. As shown in FIG. 32, a nasal cannula 1700 includes supply tubing 1710, a dummy face-piece arm 1730 and nasal prongs 1740. The nasal cannula 1700 does not include a bifurcation junction, and therefore, the rainout prior to the nose prongs 1740 may be reduced. In some embodiments, the dummy face-piece arm 1730 may be included to help secure the prongs 1740 on the patient; however, the face-piece arm 1730 may or may not be in fluid communication with the prongs 1740. A stopper or wall (not shown) may separate the prongs 1740 from the dummy face-piece arm 1730 such that aerosol does not enter the dummy face-piece arm 1730. It should be understood that the dummy face-piece arm 1730 may instead be a hollow tube fluidly connected to the prongs 1740 and/or they provide a drainage conduit for removing rainout and/or sputter without departing from the scope of the current invention.

Figure 33:
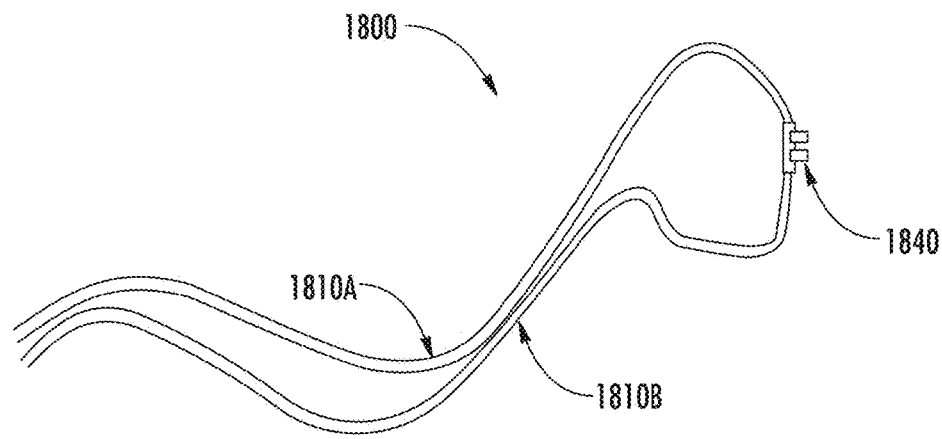
FIG. 33 is a nasal cannula configuration according to another embodiment of the present invention.

In some embodiments, rainout and/or sputtering the may be reduced by using two separate supply lines. As illustrated in FIG. 33, a nasal cannula 1800 includes two separate supply lines 1810A, 1810B that are connected to respective ends of the nasal prongs 1840. Accordingly, a bifurcation junction from a single supply tubing line is eliminated, and two separate inputs to the nasal prongs 1840 are provided. An exit from the particle selection chamber 44 in FIGS. 1-4 consequently may be modified to include two outputs to accommodate such dual supply lines. Furthermore, two independent particle selection chambers connected to single or two independent aerosol entrainment chambers can be used to provide aerosol supply into the dual cannula supply tubing lines. Lastly, two or more complete systems (nebulizer, entrainment chamber and particle selection chamber) can be used to feed into the supply lines. Such an approach may also be used to increase the output from the prongs of the nasal cannula.

Figure 34:
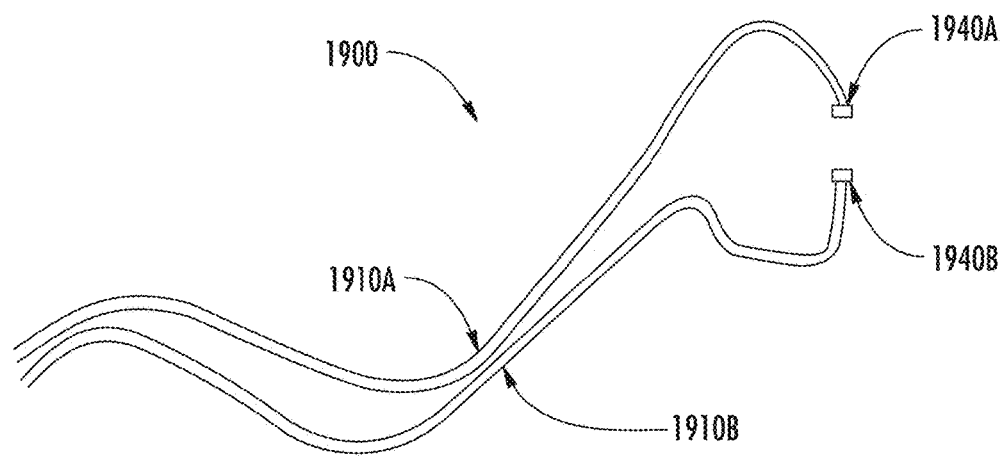
FIG. 34 is a nasal cannula configuration according to another embodiment of the present invention.

As shown in FIG. 34, another nasal cannula 1900 includes two separate supply lines 1910A, 19108, that are connected to individual nasal prongs 1940A, 19408, respectively. As illustrated in FIG. 34, the individual nasal prongs 1940A, 1940B may reduce rainout and/or sputtering as compared with conventional nasal prongs that may include abrupt changes in the flow path, which may lead to inertial impaction and rainout.

In some embodiments, in order to deliver aerosol via nasal cannula over extended periods of time without causing excessive rainout, the nasal cannula and its ability to conduct aerosol over extended periods of time at sufficient output levels may be matched to the aerosol output from the particle selection chamber. For example, nasal cannulas with larger diameter tubing and fewer impaction surfaces may be capable of conducting aerosols with larger volume of particles above 2, 3 and 4 μm respectively. Similarly, nasal cannulas with smaller diameter tubing and more impaction surfaces are only capable of conducting aerosols over extended periods of time at sufficient output levels with smaller volume of particles above 2, 3, and 4 μm respectively. An improved cannula designed for delivery of aerosol over extended periods of time at high levels of output has the largest diameter tubing still tolerated by the patients to minimize rainout in the cannula due to gravitational sedimentation while also reducing the number of impaction surfaces within the aerosol path inside the cannula to minimize rainout occurring via inertial impaction. Embodiments according to the current invention will now be described with respect to the following non-limiting examples.

c. Rates of Aerosol by Volume Deposition in the Lung During Aerosol Administration Over Extended Periods of Time To provide a representative value for aerosol rate of deposition on the surface of the lung during extended aerosol delivery, deposition based on inhaled hypertonic saline therapy for CF lung disease was analyzed. It has been demonstrated that ~110 mg to 250 mg of NaCl deposited in the lung of CF patients led to significant improvements in lung function (Elkins MR., Robinson M., Rose B. R., Harbour C., Moriarty C. P., Marks G. B., Belousova E. G., Xuan W., and Bye P. T. P. 2006. A controlled trial of long-term inhaled hypertonic saline in patients with cystic fibrosis. N Engl Med 354(3):229-240; Donaldson S. H., Bennett W. D., Zeman K. L., Knowles M. R., Tarran R., and Boucher R. C. 2006. Mucus clearance and lung function in cystic fibrosis with hypertonic saline. N Engl Jr Med 354 (3):241-250) when administered as a bolus aerosol dose for over up to ~18 minutes. An extended aerosol administration of the same mass of deposited NaCl over extended times of six to eight hours (and up to twenty four hours per day) may elicit better safety and efficacy. In order to deposit 110 mg of NaCl in the lung of CF patients with 8 hour extended aerosol administration, the rate of NaCl mass deposition on the surface of the lung may be about 0.23 mg/min. For 250 mg NaCl dose deposited in the lung, the rate of NaCl mass deposition on the surface of the lung may be about 0.52 mg/min. These rates of NaCl mass deposition define the rates of aerosol volume deposition on the surface of the airway as a function of concentrations of active pharmaceutical ingredient in the drug product. Table 6 provides such rates for the aerosol volume deposition on the surface of the airways as a function of concentration of HS in an aerosolized solution to provide these NaCl (mg) deposition rates.

TABLE 6

Rates for Aerosol Volume Deposition on the Surface of the Airways to Achieve Therapeutic Doses of NaCl Deposited over Eight Hour Aerosol Administration for Aerosolized Solutions with Different Concentration of NaCl

|  | 7% HS | 10% HS | 12% HS | 14% HS | 21% HS |
|---|---|---|---|---|---|
| Aerosol volume deposition rate on the surface of the airways to achieve 110 mg of NaCl deposited over 8 hour extended aerosol administration | | | | | |
| ul/min | 3.3 | 2.3 | 1.9 | 1.6 | 1.1 |
| mg/min of NaCl | 0.23 | 0.23 | 0.23 | 0.23 | 0.23 |
| Aerosol volume deposition rate on the surface of the airways to achieve 250 mg of NaCl deposited over 8 hour extended aerosol administration | | | | | |
| ul/min | 7.4 | 5.2 | 4.3 | 3.7 | 2.5 |
| mg/min of NaCl | 0.52 | 0.52 | 0.52 | 0.52 | 0.52 | d. Achieving Sufficient Output from the Prongs of Nasal Cannula During Aerosol Administration Over Extended Periods of Time The preceding section provided a summary of rates for NaCl mass and aerosolized NaCl solution volume deposited on the surface of the airways per unit of time. The current section discusses the aerosol volume output from the prongs of the device 10 of this invention that would be needed to achieve the rates of pulmonary deposition described in the preceding section, taking into account different deposition efficiencies. Representative deposition efficiencies may be in the ranges of ~1% to 25%. Different rates of aerosol emission from the prongs of the nasal cannula of the device of this invention are needed to result in the pulmonary deposition of the targeted 250 mg of NaCl achieved over eight hour extended aerosol administration as a function of concentration of aerosolized NaCl solution and deposition efficiencies. Table 7 below provides values for levels of aerosol output from the prongs of nasal cannula (µl/min) for 7% to 21% hypertonic saline in order to deposit 250 mg of NaCl into the lung of CF patients over 8 hours for deposition efficiencies ranging from 1% to 25% of the emitted dose (deposition efficiency=deposited dose/emitted dose from the prongs). It is apparent that at least 30 µl/min of aerosolized 7% HS emitted from the prongs of nasal cannula would be needed assuming very high 25% depositing of such intranasal aerosol in the lung. Higher outputs than 30 µl/min are desirable for intranasally administered aerosols with pulmonary deposition efficiency below 25%. Additionally, such output would have to be generated consistently without abatement over 8 hours without excessive rainout in order to deliver the desirable therapeutic dose and be well-tolerated by the patients. Should 21% hypertonic saline be used, if the deposition efficiency was 25%, an output of 10 µl/min would support administration of 250 mg of NaCl into the deep lung of CF patients. Similarly, an output of ~50 µl/min from the prongs of the nasal cannula would be needed to achieve 250 mg of NaCl deposited in the lung with 5% deposition efficiency and 7% hypertonic saline. With 1% deposition efficiency, output of ~745 µl/min from the prongs of the nasal cannula would be needed to achieve 250 mg of NaCl deposited in the lung. If only 50 mg dose of NaCl mass deposited in the lung of patients during eight hour extended aerosol administration would be therapeutically sufficient, with aerosol deposition efficiency of 25% an output of only 2 µl/min of 21% HS aerosol emitted from the prongs of nasal cannula would be needed. For other more potent therapeutic agents, an output of 10-fold or 100-fold lower magnitude (0.2 and 0.02 µl/min respectively) could be sufficient.

TABLE 7

Per Minute Output Required from the Prongs of Nasal Cannula to Deliver 250 mg of NaCl into the Lung with Different HS Concentrations and Under Different Deposition Efficiencies

|  | 7% HS | 10% HS | 12% HS | 14% HS | 21% HS |
|---|---|---|---|---|---|
| 1% deposition | 745 ul/min | 520 ul/min | 435 ul/min | 370 ul/min | 250 ul/min |
| 5% deposition | 149 ul/min | 104 ul/min | 87 ul/min | 74 ul/min | 50 ul/min |
| 10% deposition | 74 ul/min | 52 ul/min | 43 ul/min | 37 ul/min | 25 ul/min |
| 15% deposition | 50 ul/min | 35 ul/min | 29 ul/min | 25 ul/min | 17 ul/min |
| 20% deposition | 37 ul/min | 26 ul/min | 22 ul/min | 19 ul/min | 12 ul/min |
| 25% deposition | 30 ul/min | 21 ul/min | 17 ul/min | 15 ul/min | 10 ul/min |

From the rates displayed in Table 7 for aerosolized volumes of NaCl solutions emitted from the prongs of the nasal cannula (ul/min), corresponding rates of NaCl mass emission from the prongs of the cannula can be calculated (NaCl concentration (mg/ul)×aerosol emission rate ul/min). The rates for NaCl mass emission from the prongs of the nasal cannula, required to produce dosing rates in the presumed therapeutic range of 0.52 mg/min of NaCl deposited on the surface of the airways, are displayed in Table 8 as a function of deposition efficiency.

TABLE 8

Per Minute Output for the Mass of NaCl Emitted from the Prongs of Nasal Cannula and Deposited in the Lung to Deliver 250 mg of NaCl into the Lung

|  | Emitted NaCl Mass mg/min | Deposited NaCl Mass mg/min |
|---|---|---|
| 5% deposition | 10.4 mg/min | 0.52 mg/min |
| 10% deposition | 5.2 mg/min | 0.52 mg/min |
| 15% deposition | 3.5 mg/min | 0.52 mg/min |
| 20% deposition | 2.6 mg/min | 0.52 mg/min |
| 25% deposition | 2.1 mg/min | 0.52 mg/min | e. Reducing Rainout within Nasal Cannula During Extended Aerosol Delivery by Controlling Particle Size Distribution One of the challenges for extended aerosol delivery via nasal cannula is achieving a therapeutically relevant output from the prongs of the nasal cannula described above while limiting or reducing fluid accumulation in the nasal cannula.

Such accumulated fluid, or rainout, ultimately obstructs the nasal cannula and decreases the aerosol output. Rainout additionally causes sputters, or fluid droplets ejected from the prongs of the cannula, which in turn decreases the tolerability for patients. Only aerosols with small volume-normalized percentage of particles greater than 3 to ~4 µm and overall VMD of 1.2 to 1.9 µm are suitable for extended administration via nasal cannula and subsequent efficient deposition in the lung.

The current jet nebulizers and vibrating mesh nebulizer produce large amount of aerosol particles that are likely because of large size to rainout due to inertial impaction and gravitational sedimentation. These large particles lead to excessive fluid accumulation in the nasal cannula and in patients' nasal passages. Therefore, virtually all large particles need to be removed prior to entraining of such aerosol in the nasal cannula and administering such aerosol intranasally.

Additionally, the pulmonary deposition of aerosols via intranasal route points to reduced deposition efficiency in the vicinity of 1% to 25% of the emitted dose from the prongs of the nasal cannula. The removal of the large aerosol particles, which contain large amount of the aerosol mass, combined with low deposition efficiency, creates a challenge to achieve a sufficient output in terms of aerosol volume/min emitted from the prongs of the nasal cannula without creating excessive rainout in the nasal cannula.

Filtering out larger aerosol particles prior to aerosol entry into the nasal cannula limits the rainout in the cannula and enables stable output over extended aerosol delivery. Tuning of the devices in FIGS. 1-4 leads to gradually decreasing VMD of aerosols entering the nasal Cannula from above 4 µm for standalone nebulizers to ~1.3 to 1.9 µm for devices in FIGS. 1-4 with 2.5 mm nozzle operated with 2 L/min non-oscillating airflow (VMD for 2.5 mm and 3.5 mm nozzles in FIGS. 22, 23 and Table 5). In turn, such decrease in VMD leads to decreasing percentage of particles larger than 3 µm and 4 µm (Table 5). Such aerosol entering nasal cannula consequently enables stable output (FIGS. 24, 25, 30 and 35) with limited rainout in the nasal cannula (FIG. 26) over extended periods of aerosol delivery.

Figure 30:
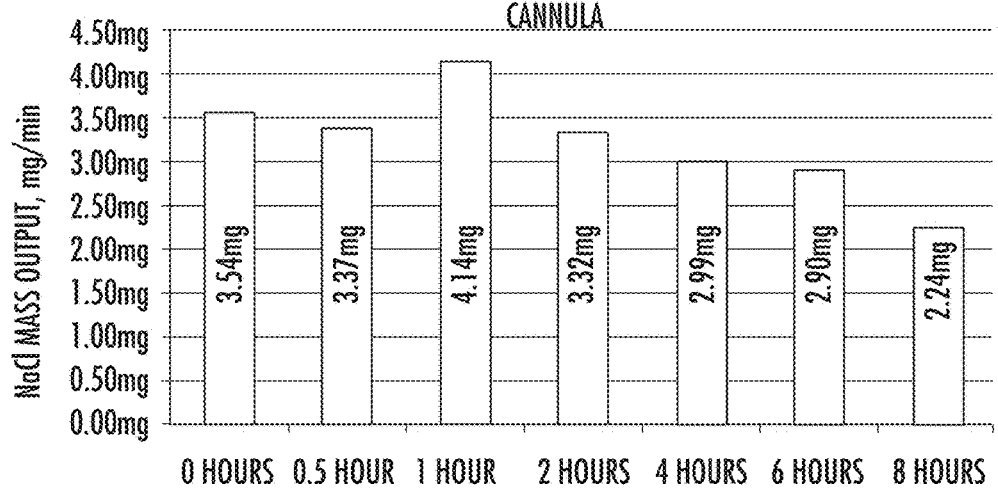
FIG. 30 is a bar graph of the NaCl mass output in mg/min for INC-based system according to some embodiments and including a conventional nasal cannula Salter HF1600 as shown in FIGS. 1-4 having a nozzle of 2.5 mm at over an eight hour time period.
Figure 35:
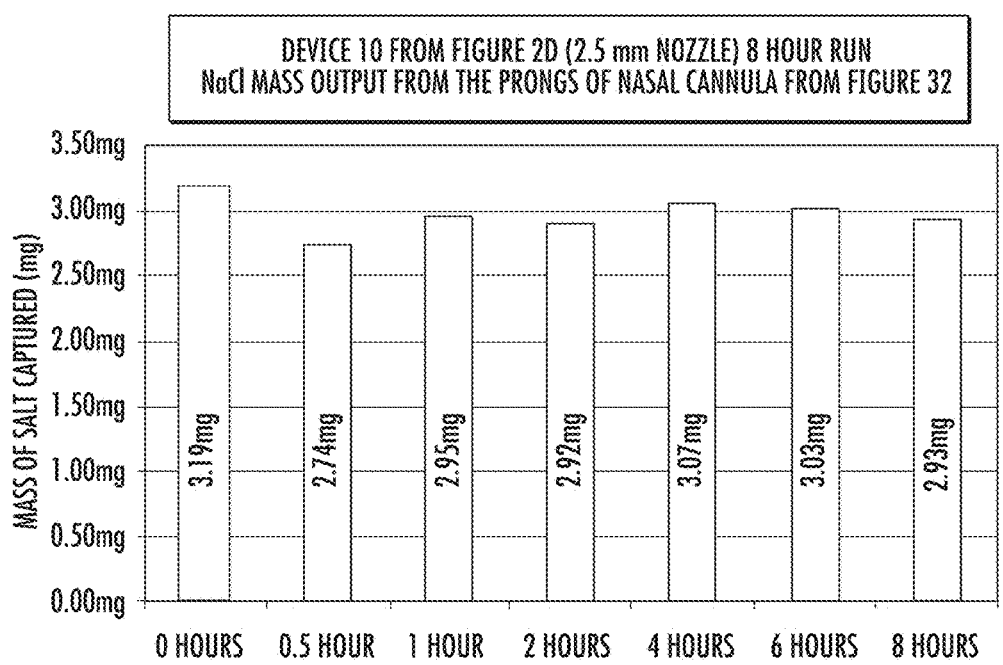
FIG. 35 is a bar graph of the captured dry NaCl delivered over 8 hours using the INC-based aerosol delivery system of FIGS. 1-4 with a custom nasal cannula as illustrated in FIG. 32 according to some embodiments.

In the examples provided below, several cannulas were tested with the device from FIGS. 1-4 over extended aerosol delivery periods ranging from 30 minutes to 8 hours. Such cannulas do not contain any rain out traps or special features designed to sequester the rain out from the aerosol path within the cannula. During 8 hour run with seven foot Salter HF1600 cannula and device from FIG. 1-4, a rainout of ~1.1 ml occurred and impaired the aerosol output towards the later portion of 8 hour run (FIG. 30). During a similar 8 hour run with a custom 7-foot nasal cannula (FIG. 32) and device from FIG. 1-4, a rainout of ~0.3 ml occurred without any impairment of the aerosol output towards the later portion of 8 hour run (FIG. 35). These results identify the approximate amount of rainout in nasal cannulas with supply tubing of 4 to 4 5 mm in internal diameter and seven to nine feet in length that, without any special rainout retention features, accumulates in the nasal cannula but does not impair stable aerosol output over 8 hours of aerosol delivery. Cannulas containing rain out traps or special features designed to sequester the rain out from the aerosol path within the cannula would be able to accommodate larger rainout volumes, for example, of up to 10 ml and higher without impairing the aerosol output over extended periods of time.

f: Limiting Sputter from the Prongs of Nasal Cannula During Extended Aerosol Delivery An excessive rainout within nasal cannula during extended aerosol delivery ultimately leads to a sputter or ejection of rained out fluid from the prongs of the nasal cannula into patients' nares. Such events, if occurring too frequently, are likely to cause patient discomfort and decrease the tolerability of such aerosol delivery over extended periods of time, especially if patients are asleep. Therefore limiting the sputter from the prongs of the nasal cannula is desirable. A range of 1-2 sputters/hour may be tolerable over extended periods of time while a sputter once every five to ten minutes, and worse yet every minute, is likely to decrease to tolerability of such aerosol delivery over extended periods of time. A properly tuned device as shown in FIG. 1-4 used in conjunction with a custom cannula (FIG. 32) produces 0.5 to 1 sputters per hour during 8 hour aerosol administration.

g. Exemplary Embodiments

A Particle Size Distribution from a Representative Vibrating Mesh Nebulizer

Figure 22:
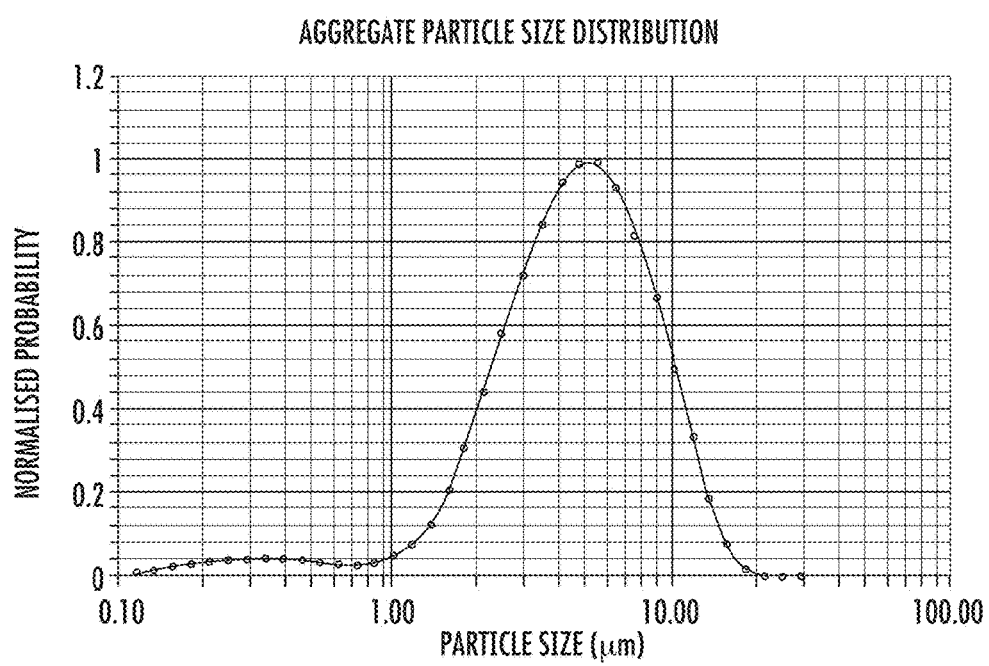
FIG. 22 is a graph of the aerosol particle size as a function of volume-normalized probability for standalone Aerogen Aeroneb Lab vibrating mesh nebulizer

Conventional jet nebulizers, ultrasonic nebulizers and vibrating mesh nebulizers typically produce particles with a relatively wide distribution of particle sizes. FIG. 22 displays a representative particle size distribution measured by laser diffraction instrument (Spraytech) for an Aerogen Aeroneb™ Lab nebulizer with 7% hypertonic saline solution. The volumetric mean diameter (VMD) as shown in FIG. 22 was 4.2 µm. Such aerosol has a large percentage of volume-normalized particles exceeding 3 to 4 µm. An aerosol of such particle size distribution may be difficult to entrain in a nasal cannula because the larger particles are likely to impact or gravitationally sediment during the course of the travel through the length of the nasal cannula. The resulting rainout may cause discomfort to the patient when such rainout liquid droplets reach the exit points of the nasal cannula and are potentially inhaled by the patient.

Figure 23:
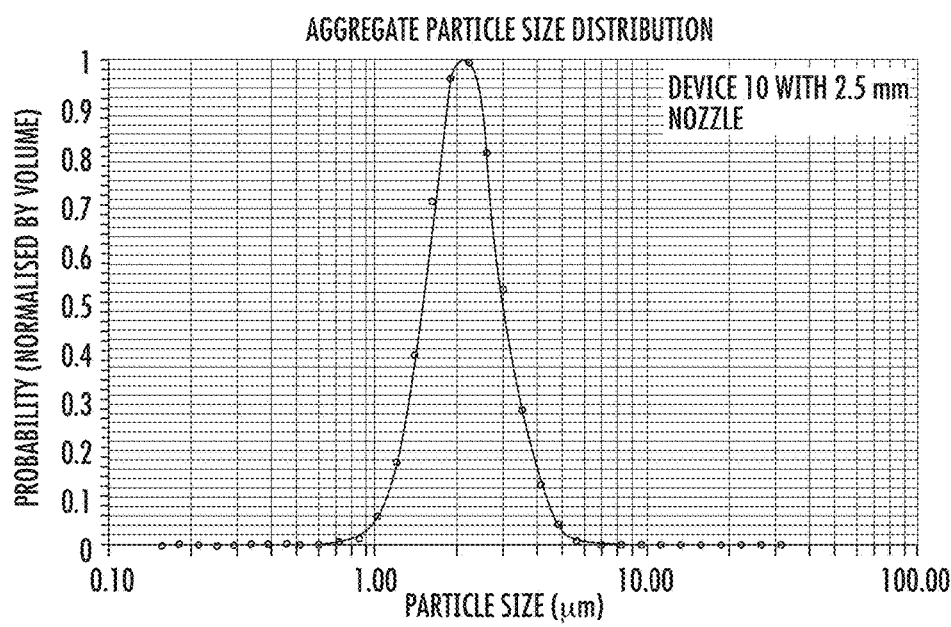
FIG. 23 is a graph of the aerosol particle size as a function of normalized probability for device 10 as shown in FIGS. 1-4 having a nozzle or jet of 2.5 mm.
Figure 24:
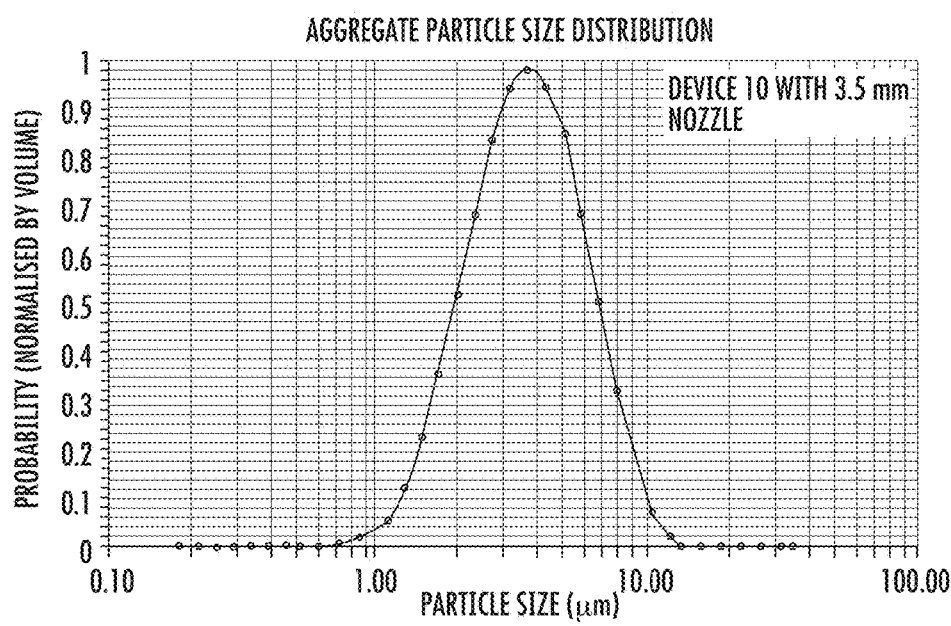
FIG. 24 is a graph of the aerosol particle size as a function of normalized probability for INC-based device as shown in FIGS. 1-4 having a nozzle or jet of 3.5 mm.

Particle Size Distribution from the Device 10 of this Invention Designed for Stable Aerosol Output Over Extended Aerosol Delivery The aerosol delivery system 10 as illustrated in FIGS. 1-4 was constructed with the specific dimensions of the device in FIG. 2B. The inertial impactor design of the particle selection chamber 40 allowed for control of the particle sizes exiting outlet 44 and consequently entering the nasal cannula. Some of the factors that may allow for tuning or controlling the particle size selection were the overall flow rate and the diameter of the inertial impactor nozzle 28. The operating parameters used in this experiment included 2 L/min flow rate with the use of compliance chamber providing non-oscillating output of 2 L/min, 7% (w/v) NaCl solution, ~20° C. and 50% relative humidity. The electronic drive distributed with the Aerogen Aeroneb™ Pro was utilized. At the flow rate of 2 L/min, 7% NaCl solution nebulized to an aerosol exiting the port 44 of device 10 of this invention equipped with 2.5 mm nozzle at the particle selection chamber with the VMD of 1.9 µm and minimal percentage of the particles larger than 4 µm (FIG. 23). Under the same conditions, the device 10 of this invention equipped with 3.5 mm nozzle generated aerosol with VMD of 3.1 µm and a larger percentage of particles above 4 um (FIG. 24).

Figure 25:
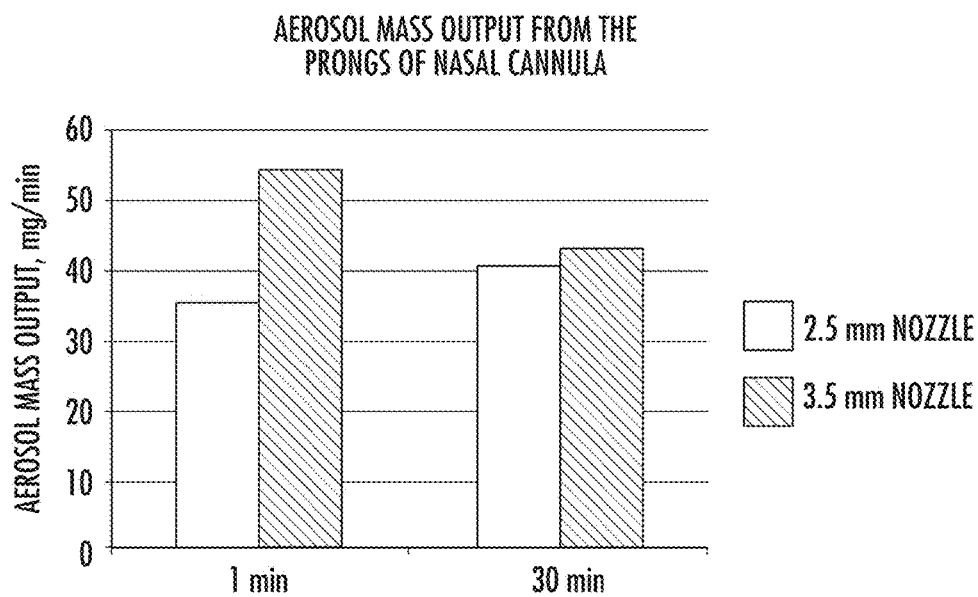
FIG. 25 is a bar graph displaying a stable output over 30 minutes with a 2.5 mm, but not a 3.5 mm nozzle, of the aerosol mass output in mg/min for INC-based system including a conventional nasal cannula Salter HF1600 for a particle selection chamber as shown in FIGS. 1-4 over a period of one minute and thirty minutes.
Figure 26:
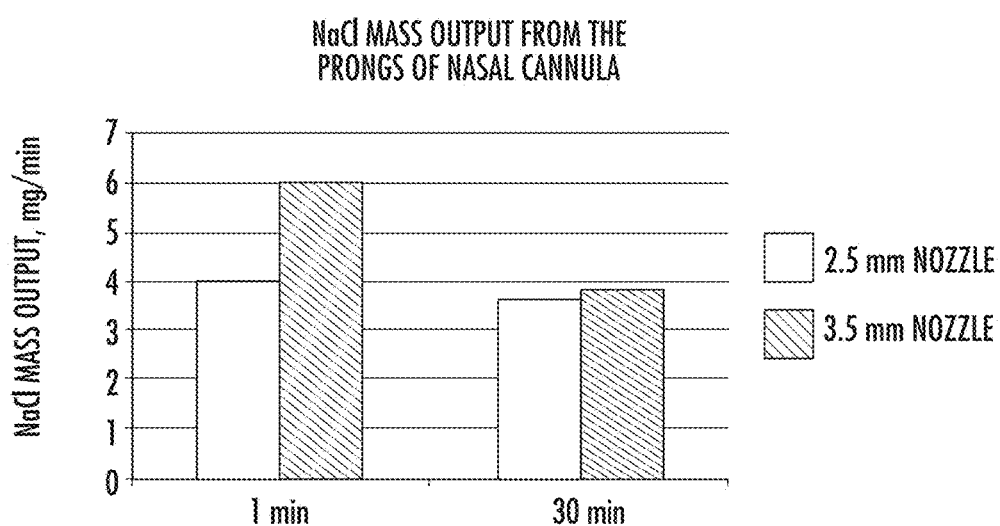
FIG. 26 is a bar graph of the NaCl mass output in mg/min displaying a stable output over 30 minutes with 2.5 mm but not a 3.5 mm nozzle for an INC-based system according to some embodiments including a conventional nasal cannula Salter HF1600 for a particle selection chamber as shown in FIGS. 1-4 over a period of one minute and thirty minutes.
Figure 27:
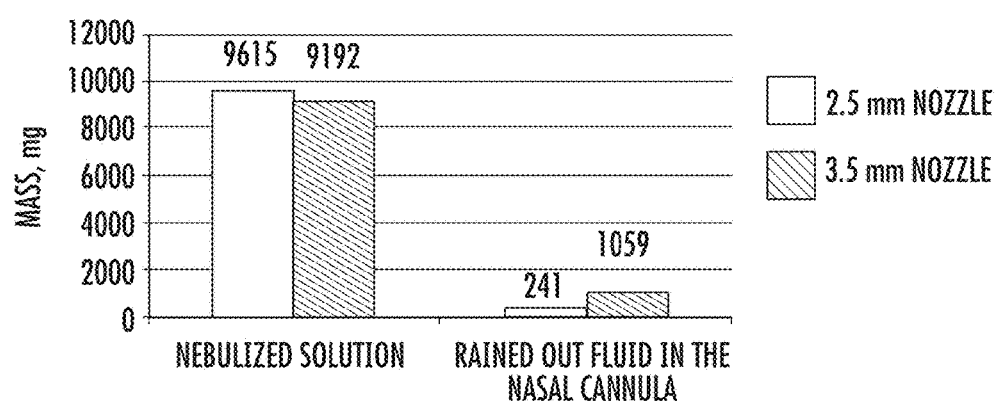
FIG. 27 is a bar graph of the mass of nebulized 7% NaCl solution and rained out fluid in the nasal cannula for an INC-based system according to some embodiments, including a conventional nasal cannula Salter HF1600, as shown in FIGS. 1-4 having an nozzle of 2.5 mm or 3.5 mm over a period of one minute at t=0 and at t=29 min post initiation of aerosol generation

Stable Aerosol Output from Device 10 of this Invention Designed for Stable Aerosol Output Over Extended Aerosol Delivery The ability to maintain stable output was tested in the course of a 30 minute run with the device 10 of this invention with the specific dimensions of the device in FIG. 2B equipped with 2.5 mm and 3.5 mm nozzles. A seven-foot long Salter™ HF1600 supplemental oxygen nasal cannula was used. The aerosol output from the prongs of the nasal cannula was collected on a filter for 60 seconds of the first minute and 60 seconds of the last minute of the run. The weight of the wet filters after the 60 second collection was used to determine the mass of the aerosol output in mg/min. Then the filters were dried, and the mass of the deposited NaCl was determined and used to calculate the output of the NaCl mass in mg/min. For the 2.5 mm nozzle, the first minute output from the prongs of the nasal cannula was 36 mg/min for the mass of the aerosol and 4.0 mg/min for the mass of NaCl (FIGS. 25 and 26). The 30th minute output was 41 mg/min for the mass of the aerosol and 3.7 mg/min for the mass of NaCl. For the 3.5 mm nozzle, the first minute output from the prongs of the nasal cannula was 55 mg/min for the mass of the aerosol and 6.1 mg/min for the mass of NaCl (FIGS. 25 and 26). The last minute output of the 30 minute run was 43 mg/min for the mass of the aerosol and 3.8 mg/min for the mass of NaCl. For the 2.5 mm nozzle, the output at the end of the 30 minute run remained unchanged compared to the $1^{st}$ minute of the 30 minute run (113% of the $1^{st}$ minute aerosol mass/min and 92% of the 1st minute NaCl mass/min). For the 3.5 mm nozzle, the output at the end of the 30 minute run decreased compared to the $1^{st}$ minute of the 30 minute run (77% of the $1^{st}$ minute aerosol mass/min and 63% of the $1^{st}$ minute NaCl mass/min). In both runs, comparable amounts of 7% NaCl solution were nebulized (9.6 ml for the 2.5 mm nozzle and 9.2 ml for the 3.5 mm nozzle).

Diminished Rainout in the Nasal Cannula with the Device 10 of this Invention with 2.5 mm Nozzle In the 30-minute experiment described above, the mass of the rained out fluid in the nasal cannula after the completion of the 30 minute run was determined by weighing the nasal cannula before and after the 30 minute run. The mass of the liquid rained out in the nasal cannula was approximately 4.4-fold higher in a device in which the entrainment chamber outlet 28 had a diameter at a distal exit end 28B of 3.5 mm nozzle compared with a 2.5 mm diameter distal exit end 28B (241 mg of rained out liquid in the setup with the 2.5 mm diameter end 28B compared to 1,059 mg of rained out liquid in the setup with the 3.5 mm diameter end 28B as shown in FIGS. 1-4 and FIG. 27).

Tuning the Aerosol Output Exiting Port 44 of the Device 10 by Changing the Diameter of the Nozzle 28B As described in the 30-minute experiment above, changing the diameter of the nozzle 28B enables the tuning of the device 10 performance with regards to the particle size distribution, the steady aerosol output and rainout accumulated within the nasal cannula. The end 28B may be provided as a separate piece from the entrainment chamber 20 and particle selection chamber 40. in some embodiments, the end 28B may be removable such that different sizes of nozzles may be inserted into the chambers 20, 40 for tuning the chamber for increased adjustability and tuning. However, it should be understood that the end 28B may also be integrated into the device 10 without departing from the scope of the invention.

The Dimensions of the Aerosol Entrainment and Particle Selection Chambers of the Device 10

Figure 28:
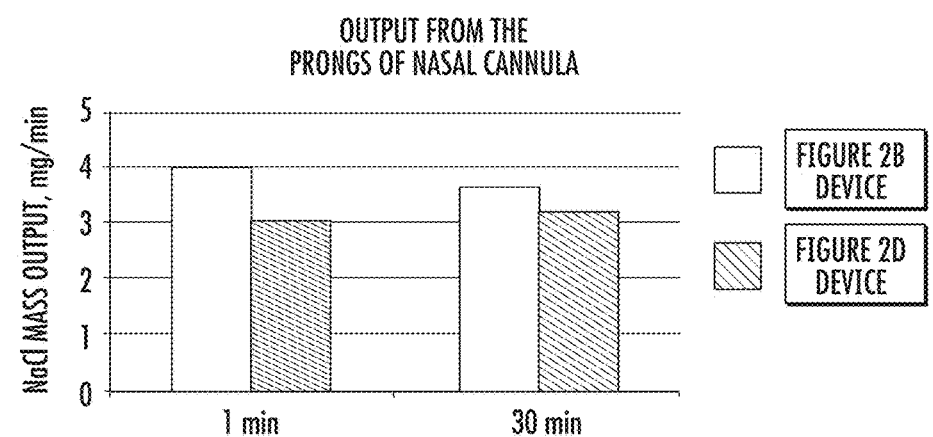
FIG. 28 is a bar graph of the NaCl mass output in mg/min for INC-based systems of different dimensions according to some embodiments and including a conventional nasal cannula Salter HF1600 as shown in FIGS. 1-4 and having the dimensions shown in FIG. 2B over a period of one minute at t=0 and at t=29 min post initiation of aerosol generation
Figure 29:
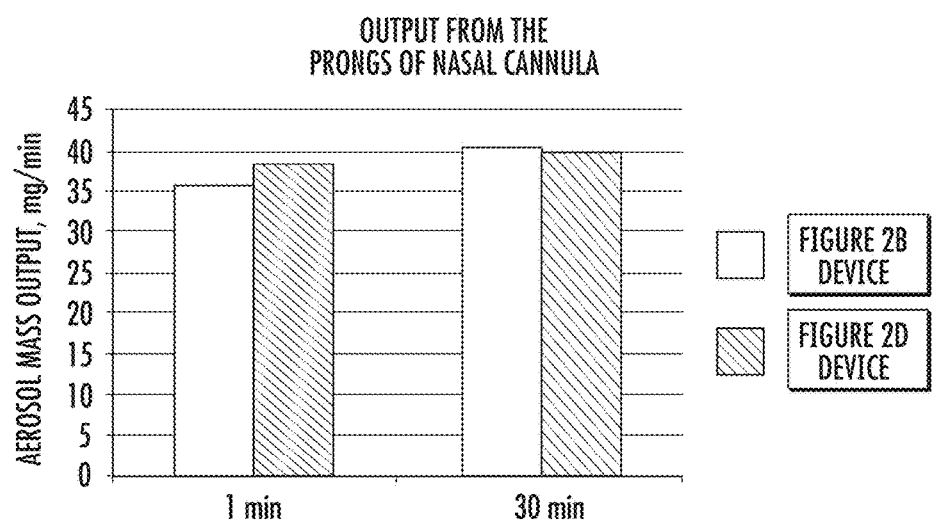
FIG. 29 is a bar graph of the aerosol mass output in mg/min for INC-based systems of different dimensions according to some embodiments and including a conventional nasal cannula Salter HF1600 as shown in FIGS. 1-4 and having the dimensions shown in FIG. 2D over a period of one minute at t=0 and at t=29 min post initiation of aerosol generation

Two sizes of the aerosol delivery system 10 were assembled (FIGS. 2B and 2D), and the aerosol output from these devices was compared. The diameter of the nozzle 28B was 2.5 mm in both devices. The aerosol delivery system 10 of smaller dimensions (FIG. 2D) was able to maintain similarly stable output over a 30 minute time period compared to an analogous system of larger dimensions (FIG. 2B) under the same operating conditions (FIGS. 28 and 29). Both systems provided generally the same or similar output. Without wishing to be bound by any particular theory, it is currently believed that the dimensions of the chambers 20, 40 may not have a significant effect on the aerosol output or performance of the system. For the smaller system, the first minute output from the prongs of the nasal cannula was 38 mg/min for the mass of the aerosol and 3 mg/min for the mass of NaCl. The last minute output of the 30 minute run was 40 mg/min for the mass of the aerosol and 3.2 mg/min for the mass of NaCl. The mass of rained-out fluid accumulated in the nasal cannula over the 30 minute run was 205 mg for the 2.5 mm outlet end 28B compared to 241 mg of fluid accumulated in the nasal cannula in the larger system.

The performance of the smaller device 10 from FIG. 2D was tested further with different nasal cannulas in the course of an 8-hour experiments as described below.

Impact of Stable Vs. Pulsatile Airflow on the Performance of Incorporated Nebulization Chamber in FIGS. 1-4

Commonly available peristaltic, diaphragm or rotary vane pumps are often characterized by an average airflow per unit of time such as L/min. However, such average is often a result of pulsatile or oscillating airflow instead of a steady output. Often a compliance chamber, a container of certain volume exceeding multiple times a volume ejected per single operating cycle of such pump, is used to smooth out the amplitudes and produce a stable, uniform output.

Figure 37:
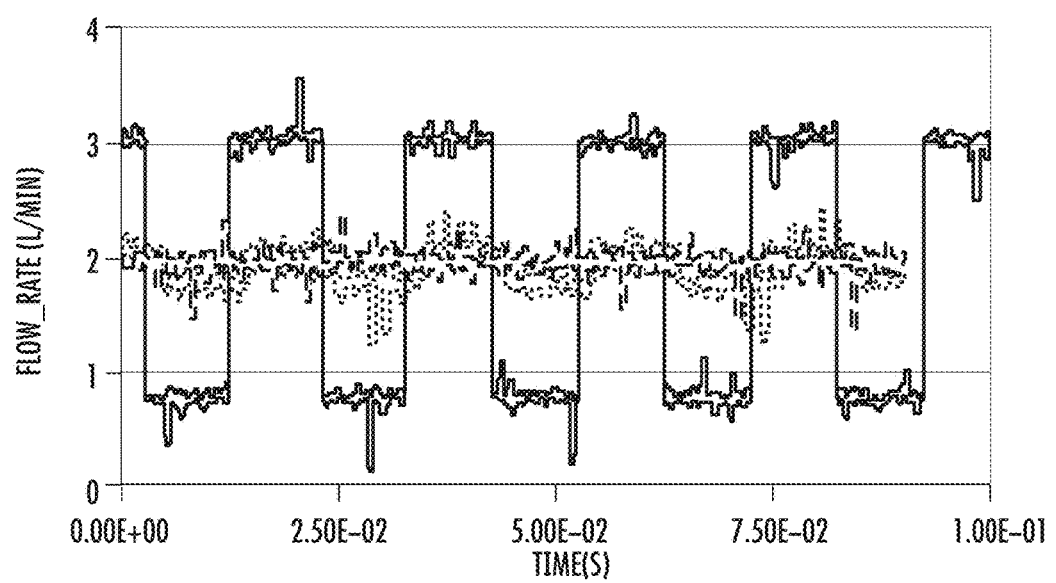
FIG. 37 is a graph of the flow rate output versus time from a direct connection to a peristaltic pump and from a compliance chamber.
Figure 38:
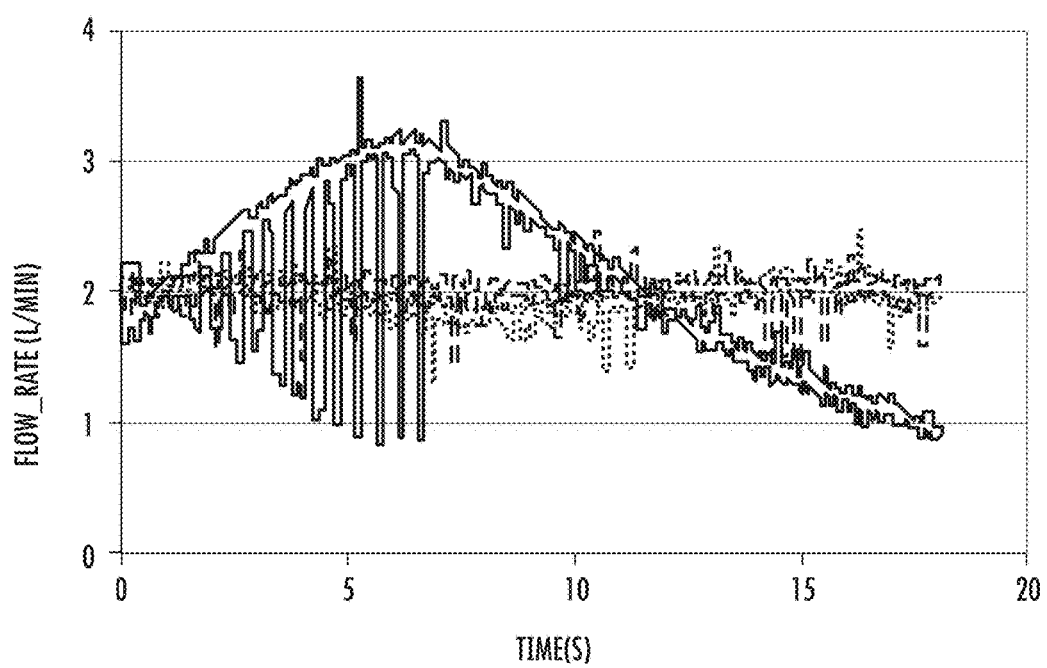
FIG. 38 is a graph of the flow rate versus time from a direct connection to a peristaltic pump and from a compliance chamber.

To assess flow pulsatility of a peristaltic Pump 130 used in testing of devices in FIG. 1-4, the analogue output of the flow meter TSI 4000 was wired to an Agilent Technologies mixed signal oscilloscope (E1457) and the data was logged to usb. Raw voltage was recorded and the flow rate post-processed (calibrated using the fact that the voltage output range 0-10 V represents a flow rate range from 0-200 L/min) at two frequencies (to investigate both small and large scale variations). A compliance chamber with a volume of 2 L was connected in line to the output of the pump and its impact was explored. FIGS. 37 and 38 display the oscillatory nature of the Pump A output and the impact of 2 L compliance chamber on the amplitude of airflow. Compressed air was used to provide a steady airflow for comparison. The use of 2 L compliance chamber reduced or eliminated the oscillatory nature of the output from Pump A.

Figure 39:
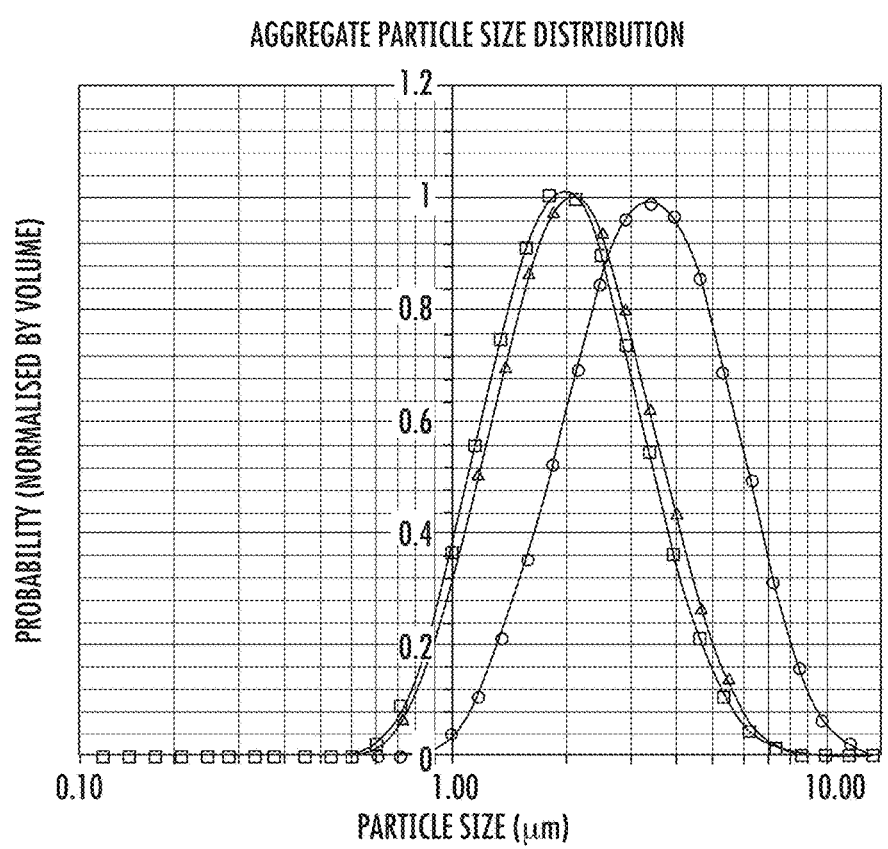
FIG. 39 is a graph of the particle size of an aerosol output from the delivery system of FIGS. 1-4 using a 3.5 mm nozzle with no cannula and a compliance chamber (two lines with circle symbols) and a FIG. 46 shows a graph of the impact of 7% and 14% HS administered at equal rates of NaCl mass deposition on ASL height in cultured human bronchial epithelial cells.

The ability of the integrated nebulization chamber from FIG. 2B to remove large particles was explored with and without a compliance chamber and Pump A. Under identical operating conditions with 3.5 mm nozzle and 2 L/min average airflow, the oscillatory airflow produced by Pump A without a compliance chamber led to more effective removal of large particles compared to steady airflow from Pump A with a compliance chamber (VMD of 1.9 μm vs. 3.1 μm respectively, FIG. 39). The decreased VMD is accompanied by decreased rate of aerosol volume emission since large amount of aerosol volume is contained within the large aerosol particle. Given these outcomes, device 10 of this invention is able to produce aerosols from port 44 with (1) small percentage of particles above 3-4 μm and (2) sufficient rate of aerosol emission by either using a non-pulsatile airflow and a slightly smaller nozzle 28B diameter or by using a pulsatile airflow and slightly larger nozzle 28B diameter, all other factors and operating conditions being equal.

In order to produce a steady airflow from the devices of this invention from FIG. 2B, a compliance chamber 133 was used downstream of pump 130. However, an oscillating airflow can be used with to increase the ability of the incorporated nebulization chamber to filter out large aerosol particles. Accordingly, in some embodiments, a pulsed flow generator 134 as shown in FIG. 2C may be used to control the pump input into the aerosol delivery system 10. However, it should be understood that the pulsed flow of a pump may be sufficient to increase the ability of the incorporated nebulization chamber to filter out larger aerosol particles according to some embodiments.

Figure 2D:
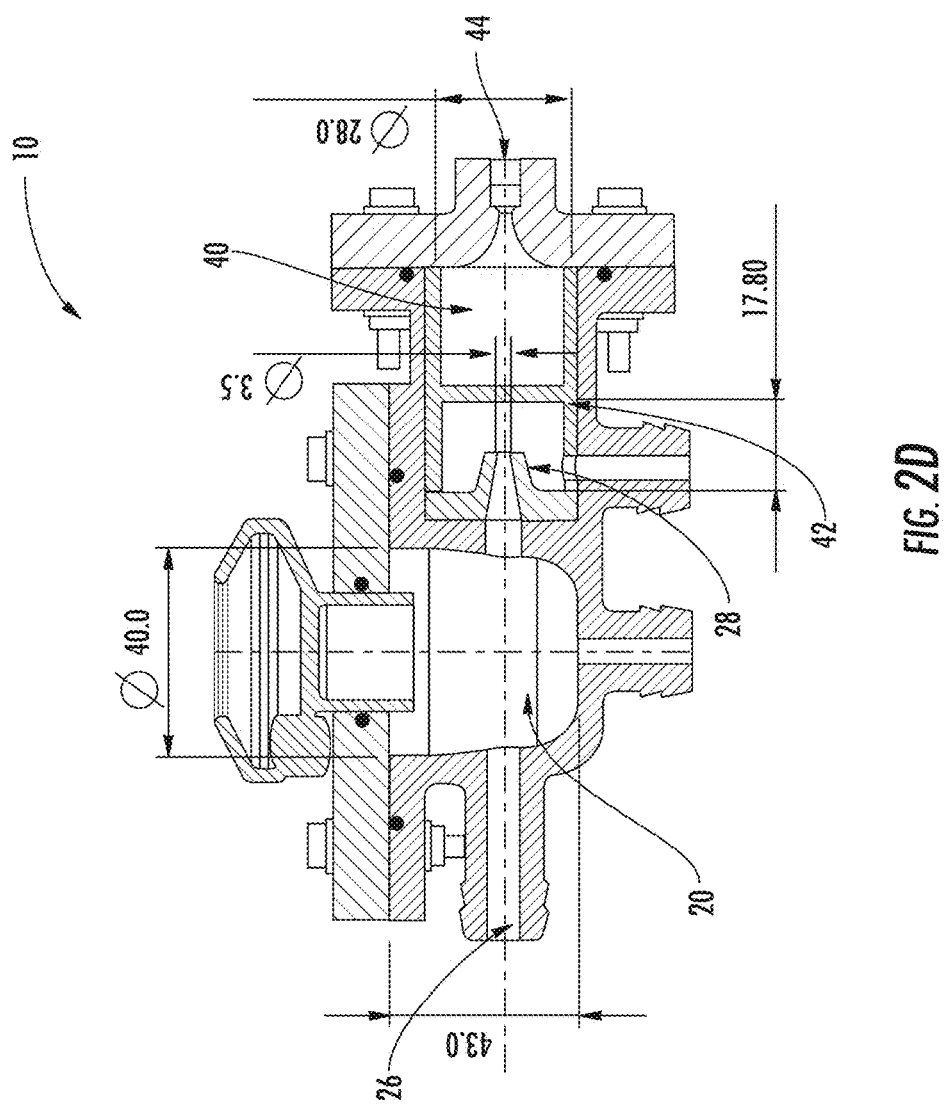
FIG. 2C illustrates the aerosol delivery system of FIGS. 1, 2A as coupled to a pump and pulsed flow generator. Exemplary dimensions of the aerosol delivery system of FIG. 2A are illustrated in FIGS. 2B-2D.

Cannulas for Extended Aerosol Delivery Tested with Device 10 with Dimensions from FIG. 2D Previously, nasal cannulas have been designed to minimize condensation of fully humidified gases passing through them or to enable high gas flow through them as is the case with high flow supplemental oxygen. However, the physics of accumulation of rainout from aerosols, dominated by gravitational sedimentation and inertial impaction, is fundamentally different than the condensation of water vapor that dominates liquid accumulation with humidified gases passing through a nasal cannula. Thus, new nasal cannula designs were implemented to minimize rainout from aerosols passing through the nasal cannula.

In order to deliver aerosol via nasal cannula over extended periods of time without causing excessive rainout, the nasal cannula and its ability to conduct aerosol over extended periods of time at sufficient output levels may be carefully matched to the aerosol output from the particle selection chamber. Nasal cannulas with larger diameter tubing and fewer impaction surfaces are capable of conducting aerosols with larger volume of particles above 2, 3 and 4 µm respectively without rainout. Similarly, nasal cannulas with smaller diameter tubing and more impaction surfaces are only capable of conducting aerosols over extended periods of time at sufficient output levels with smaller volume of particles above 2, 3, and 4 µm respectively without rainout. A cannula designed for delivery of aerosol over extended periods of time at high levels of output should have (1) the largest diameter tubing tolerated by the patients to minimize rainout in the cannula due to gravitational sedimentation and (2) a reduced number of impaction surfaces within the aerosol path inside the cannula to minimize rainout occurring via inertial impaction.

Figure 36A:
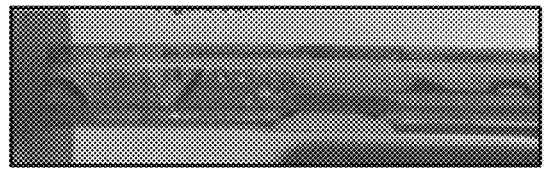
FIGS. 36A-36E are digital images of rainout in cannula comparing conventional cannula Salter HF1600 (FIGS. 36A-C) to a custom nasal cannula as shown in FIG. 32 having reduced rainout according to some embodiments (FIG. 36D, E).
Figure 36B:
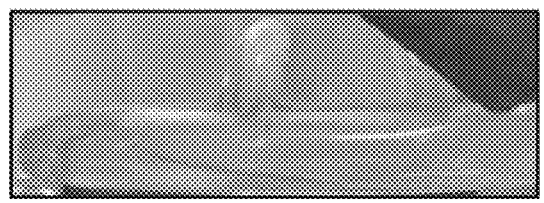
Figure 36C:
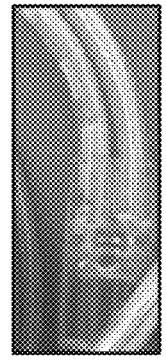

Standard supplemental oxygen nasal cannula such as Salter HF1600 contains 3-9 feet of supply tubing 1610, a bifurcation junction 1620, face-piece tubing 1630, a face piece and prongs 1640 as shown in FIG. 31. Such cannula may generate a substantial amount of rainout (30 minute run data in Table 9 with device 10 with dimensions from FIG. 2D and 2.5 mm and 3.5 mm nozzle 28B). Such rainout leads to an accumulation of fluid within the cannula, leading to a sputter from the prongs, and decrease aerosol output over extended aerosol administration periods. In an 8-hour run with a Salter HF1600 cannula under standard operating conditions (device 10 with dimensions from FIG. 2D, 2.5 mm nozzle, 2 L/min airflow, 7% hypertonic saline), a substantial amount of fluid accumulated within the cannula with sputters occurring every 5 to 10 minutes beyond 2 hours of aerosolization and clear migration of large droplets of fluid in the tubing of the cannula. At the end of the 8-hour run, approximately 1.1 ml accumulated within the cannula as determined by the change in weight of the cannula before and after the 8 hour run and further supported by the visual observations of fluid pooling in the cannula (FIG. 36A-36C at the end of 8 hour run). Consequently, the aerosol output decreased towards the end of the 8-hour run (FIG. 30).

Due to such suboptimal performance of existing supplemental oxygen nasal cannulas during extended aerosol delivery, custom cannulas were designed with improved aerosol conducting properties over extended periods of time (FIGS. 32-34). The improvements were in reduction of rainout were achieved by extending a single line of the supply tubing directly to the face-piece (FIG. 32), by extending two lines of supply tubing to the face piece (FIG. 33) or by entraining two lines of supply tubing directly to the nasal prongs (FIG. 34). Internally smooth supply tubing with internal diameter of 4.5 mm and 7-foot length was used. The face piece 1741 diameter was 5 mm with the length of the face piece of 25 mm from the end of the supply tubing to the beginning of the dummy face-piece arm 1730. Such cannulas produced up to three-fold lesser rainout compared to non-optimized supplemental oxygen nasal cannula Salter HF1600 over 30 minute run (30 minute run data in Table 9 with device 10 with dimensions from FIG. 2D and 2.5 mm and 3.5 mm nozzle 28B).

Figure 36D:
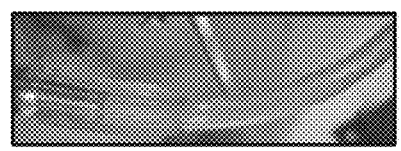
Figure 36E:

Additionally, such cannulas demonstrated improved performance over 8-hour aerosol delivery with stable output without abatement over 8 hours (FIG. 35). In contrast, un-optimized seven-foot Salter™ HF1600 cannula used under similar conditions produced gradually decreasing NaCl mass output over 8 hours (FIG. 30). Furthermore, the overall rainout accumulated in the custom cannula was reduced compared to Salter HF1600; during an 8-hour run, the custom cannula from FIG. 34 accumulated 0.3 ml within the cannula (FIGS. 36D and 36E) compared to ~1.1 ml of rainout accumulated in Salter HF1600 (FIGS. 36A-C). Lastly, the sputter from the prongs on the nasal cannula occurred at a rate of ~0.5 to 1 times per 1 hour (average of 224µ ⅛ hours; ~50 µl/sputter lead to ~0.5 sputters/hour) compared to 6 to 12 times per hour for Salter HF1600.

TABLE 9

Performance of Standard and Optimized Cannulas in Extended Aerosol Delivery

| Cannula | INC nozzle (mm) | n repeats | $1^{st}$ min output, NaCl (mg/min) | $30^{th}$ min output, NaCl (mg/min) | Rainout (ul) | Rainout (%) | Sputter (ul, %) |
| --- | --- | --- | --- | --- | --- | --- | --- |
| Full HF1600 | 3.0 mm | n = 4 | 4.4 | 4.0 | 803 | 5.3 | N/A |
| Full HF1600 | 2.5 mm | n = 2 | 3.1 | 3.4 | 203 | 1.1 | N/A |
| Custom #1 FIG. 32 | 3.0 mm | n = 2 | 5.6 | 4.7 | 610 | 3.9 | N/A |
| Custom #1 FIG. 32 | 2.5 min | n = 2 | 3.0 | 2.6 | 200 | 1.1 | N/A |
| Custom #2 FIG. 33 | 3.0 mm | n = 2 | 4.7 | 3.9 | 360 | 2.0 | 0 ul, 0% |

TABLE 9-continued

Performance of Standard and Optimized Cannulas in Extended Aerosol Delivery

| Cannula | INC nozzle (mm) | n repeats | 1st min output, NaCl (mg/min) | 30th min output, NaCl (mg/min) | Rainout (ul) | Rainout (%) | Sputter (ul, %) |
|---|---|---|---|---|---|---|---|
| Custom #2 FIG. 33 | 2.5 mm | n = 3 | 3.1 | 2.8 | 151 | 0.8 | 0 ul, 0% |
| Custom #3 FIG. 34 | 3.0 mm | n = 2 | 4.1 | 3.8 | 262 | 1.5 | 54 ul, 0.3% |
| Custom #3 FIG. 34 | 2.5 mm | n = 2 | 3.0 | 3.0 | 110 | 0.6 | 0 ul, 0% |

Passive Particle Size Selection Provides Aerosols Suitable for Administration Via Nasal Cannulas Irrespective of Starting Particle Size Distribution from the Aerosol Generator In some embodiments, passive particle size selection may be provided to produce aerosols having a suitable VMD for administration via nasal cannulas over a period of time that is greater than 30 minutes or as long as two, four, six or eight or ten or twenty-four hours or more irrespective of particle size distribution entering the device of this invention from an aerosol generator. As such, embodiments according to the present invention may be capable of incorporating input from a variety of aerosol generators including vibrating mesh nebulizers, jet nebulizers and ultrasonic nebulizers to produce aerosols having a reduced VMD. Any suitable aerosol generator may be used, including, but not limited to, nebulizers based on vibrating mesh technologies from Aerogen Aeroneb™ Lab, Pro and Solo, Pari Eflow™ vibrating mesh technologies, vibrating horn technologies by Omron™, vibrating mesh or ultrasonic technologies from Phillips and other manufacturers. As such, the device in FIGS. 1-4 could be used as a "spacer" to normalize aerosols prior to their entry into a nasal cannula. In some embodiments, nebulizers generating 50%, 75% or 100% of particles below 3 µm VMD may be desirable for use with the entrainment chambers and particle selection chambers described herein.

B. Dry Powder Administration

To avoid undesired dehydration of airway epithelial cells, and/or achieve one or more other objects as described herein, in addition to the preferred liquid-based nebulizers for administering aerosols for use in carrying out the present invention, dry powder inhaler technology may also be utilized to deliver the desired therapeutic agents described in this invention according to the methods of this invention.

According to this embodiment, instead of administering a bolus of dry powder formulation of the therapeutic agents as is customary with dry powder inhaler technology, an infusion of dry powder is administered to patients in needs of such treatment according to preferred rates of pulmonary deposition for the mass of dry powder-formulated therapeutic agents described herein. For example, for dry powder NaCl therapy, the rates for mass of NaCl per unit of time deposited in the tracheobronchial tree of patients in need of such treatment would be in the range of the preferred rates described in the methods of this invention. According to this embodiment, dry powder inhaler technology of the prior art is configured for administration over long time domains.

Alternatively, intermittent pulses of dry powder formulation of the therapeutic agents administered according to the preferred rates for mass per unit of time of pulmonary deposition as described in the methods of this invention are be also used.

Metered dose inhaler systems and apparatus configured for administration over long time domains can also be used instead of the dry powder inhaler technology to carry out the methods of this invention.

In some embodiments, the aerosol (liquid or dry powder) administering step comprises limiting the rate at which said active agent is administered, so that at least one undesired side-effect of said active agent (e.g., dehydration of lung airway epithelial cells, undesirably high system levels of said active agent, receptor desensitization by said active agent, undesirably short residence time in or on a target tissue at sufficiently high concentration, etc.) is reduced.

In some embodiments, the administering step comprises extending the duration for which said active agent is administered so that at least one desired effect of said active agent (e.g., hydration of airway mucus secretions; enhanced mucus clearance; extended residence time in or on a target tissue at sufficiently high concentration) is enhanced (e.g., as compared to the extent of the desired effect achieved when the same amount of said active agent is administered over a shorter period of time, for example: a time of one half, one third, or one quarter the time of the extended duration administration.

Particular parameters of the administering step will depend upon the particular active agent being administered. For example, where the active agent is an osmolyte that comprises a solution of sodium chloride in water, the sodium chloride may be included in an amount of from 0.5, 1, 2 or 4 percent to 8, 10, 12, 20, 30 or 40 percent by weight and the administering may be carried out by depositing from 0.1 to 3 mg of the sodium chloride to the lung surfaces of said subject per minute.

In some embodiments, the administering step is carried out for a time of 1, 2 or 4 minutes up to 30, 40 or 60 minutes.

In some embodiments, the administering step is carried out for a time of from 30, 40 or 60 minutes up to 2, 4, 6 or 8 hours.

In some embodiments, the administering step is carried out for a time of 2, 4, 6 or 8 hours up to 12 or 24 hours.

In some embodiments, the administering step is carried out overnight and/or while said subject is sleeping.

The present invention is explained in greater detail in the following non-limiting Examples.

EXPERIMENTAL

Counterintuitive to the prior "faster is better" approach, we found that the administration of an HS aerosol at substantially slower rates (than jet and vibrating mesh nebulizers used in practice) over an extended time domain, improves the therapeutic benefit of HS defined as the integrated (total) increase in airway surface liquid (ASL)

volume (or height) for a fixed mass of NaCl deposited on the airways surface. Furthermore, we find that decreasing the delivery rate of HS minimizes an unintended consequences of inhibiting ciliary beating (or mucus clearance) and producing pro-inflammatory mediators e.g. IL-8. These data are described below.

The Effects of HS Delivery Rate on ASL Height (Volume)

The data that generated our discoveries emanate from studies of the effects of HS deposition on ASL hydration utilizing well-differentiated, primary human bronchial epithelial (HBE) cell cultures derived from donor lungs. The HBEs recapitulate a number of properties of the airway epithelia in vivo including 1) differentiation into ciliated cells and goblet cells; 2) ion transport mediated ASL volume regulation; 3) the ability to produce mucins and mucus (Davidson et al., Am J Physiol Lung Cell Mol Physiol. 2000 October; 279(4):L766-78 and Bernacki et al., Am J Respir Cell Mol Biol. 1999 April; 20(4):595-604), and 4) facilitate coordinate transport of the mucus layer (Matsui et al., *Cell* 95:1005-1015).

To test the effects of 7% HS delivery rate in vitro, we designed a modified ultrasonic nebulizer capable of delivering small, nanoliter volumes of 7% HS to cultures that simulate pulmonary deposition rates in vivo from different nebulizer systems.

We compared the change in ASL height (i.e. hydration) following the deposition of 7% HS using deposition rates and delivery times which model what is achieved when HS is administered in vivo from different nebulizer devices. As shown in FIG. 40, the predicted rate of aerosol deposition in the lung from a given nebulizer is variable and differs with the anatomical region of the lung. To select deposition rates to test in vitro which are representative of the deposition from different commercial nebulizers, we averaged the predicted aerosol deposition rate for the relevant large airway generations of the lung as these regions will encounter the greatest aerosol volume/surface area (this prediction is supported by multiple radiotracer deposition studies in vivo). Therefore, we evaluated deposition rates of 100 and 200 nl/min/cm$^2$ for the Pari LC Plus (jet nebulizer) and Pari eFlow (vibrating mesh nebulizer), respectively. In addition, we tested the effects of decreasing HS deposition 4-fold relative to what is predicted for the LC Plus (25 nl/min/cm$^2$ for 60 minutes) (FIG. 41A). Importantly, while the rate of HS deposition and the time of delivery are different for the three conditions tested, the mass of NaCl, or the dose of NaCl, is identical for all three conditions (105 μg delivered to the 1 cm$^2$ culture of HBEs). We find that the slowest HS delivery rate tested (25 nl/min/cm$^2$) produced the greatest cumulative effect of ASL height (hydration), which was >2-fold (compared to the LC Plus nebulizer) or >4-fold (compared to the state-of-the art eFlow nebulizer) with respect to the AUC$_{1h}$ (FIG. 41C). Below, we describe the mechanistic basis that produces this counter-intuitive effect.

Mechanistic Basis for Increased Integrated Efficacy with Slow HS Delivery

Figure 41B:
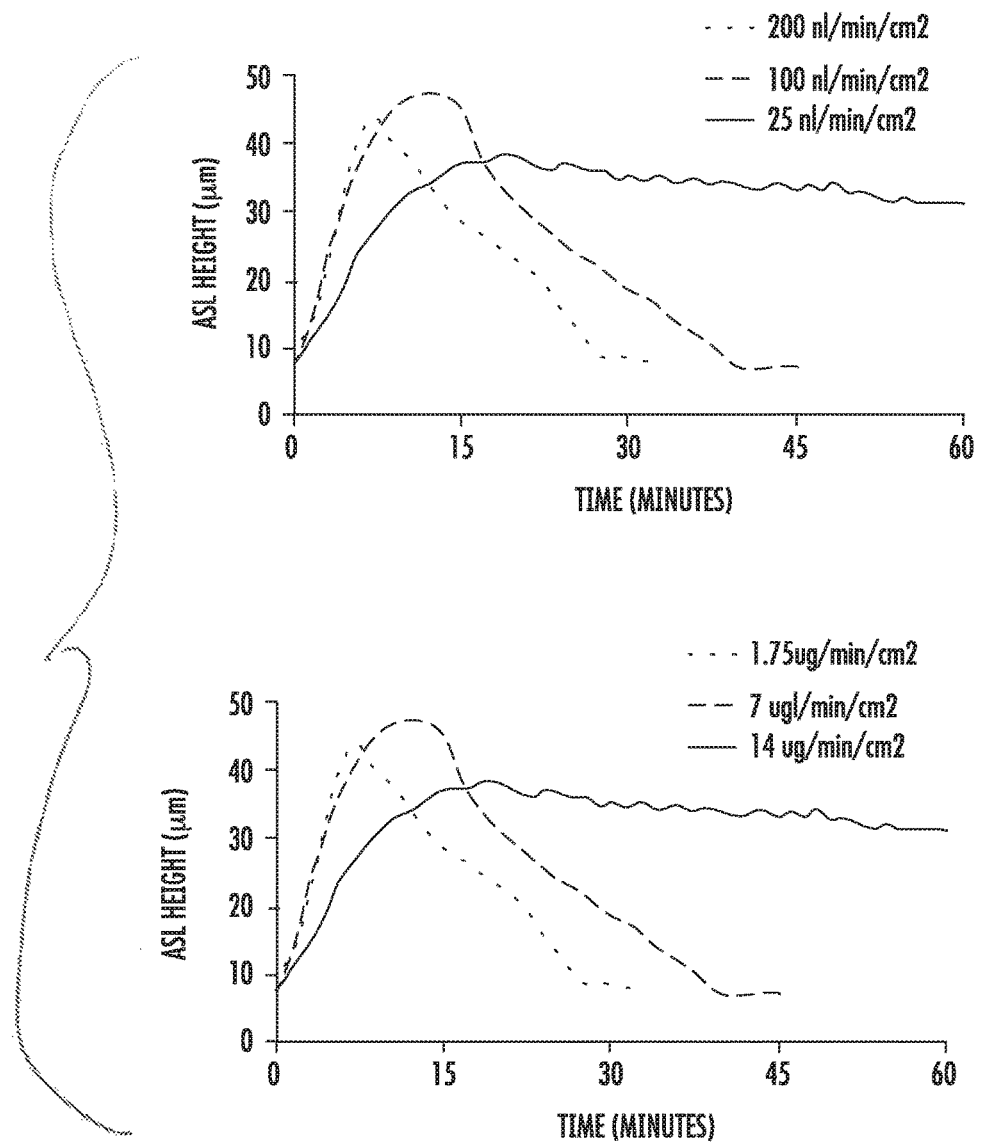
Figure 41C:
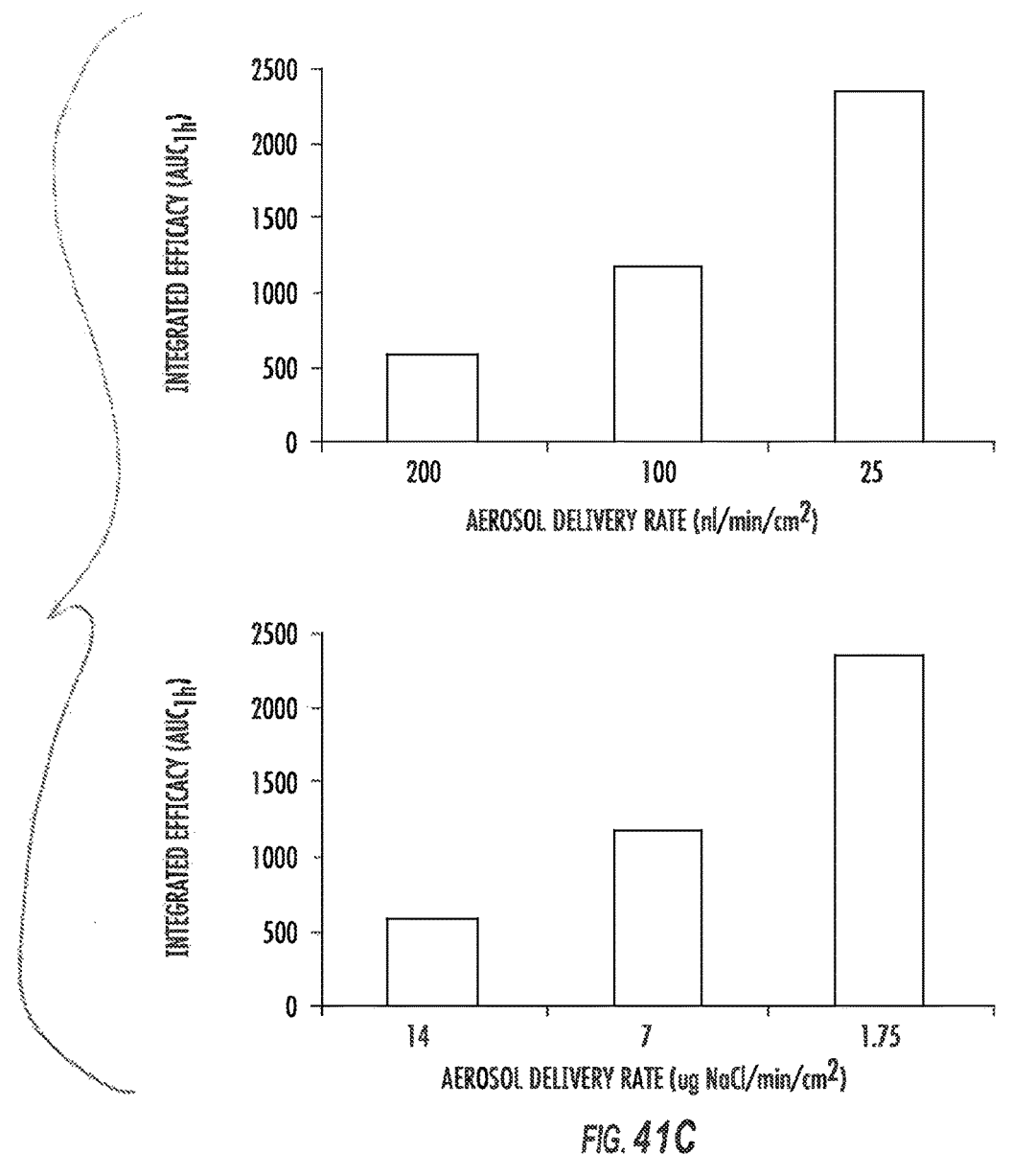
Figure 42A:
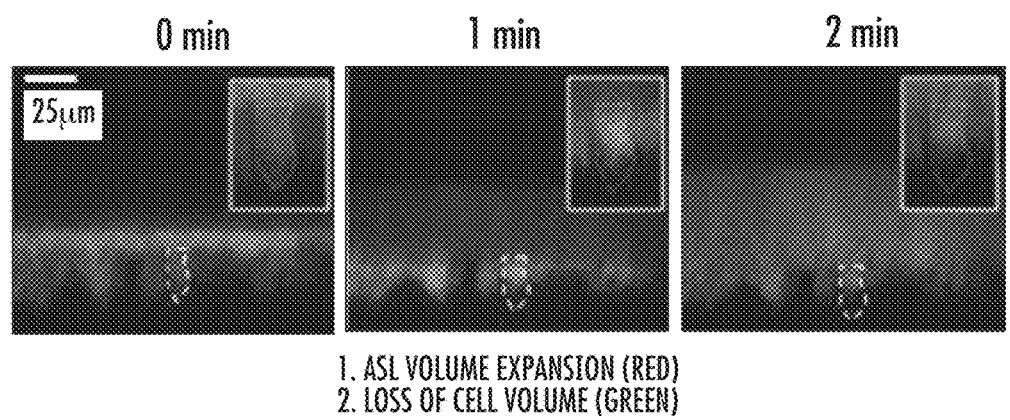
Figure 42B:
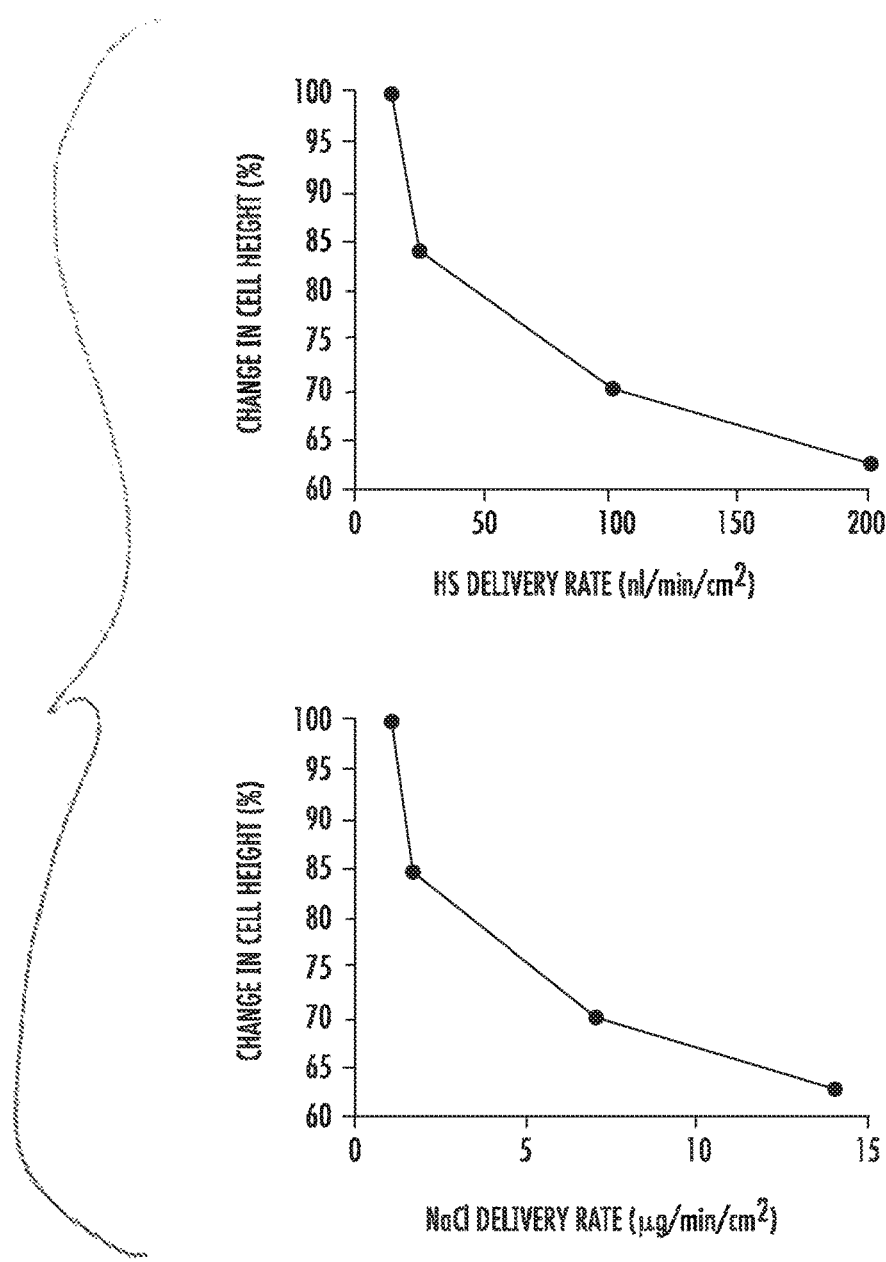

The mechanisms mediating this unexpected result are complex. The ASL volume (hydration) response to rates of deposition mimicking the LC Plus, is initially linear with time subsequently plateaus during continued aerosolization, and rapidly returns to baseline after cessation of the aerosol due to the activity of sodium absorption (inhibited by amiloride) (FIG. 41B). The plateau is associated with cell shrinkage (due to increased luminal osmolarity), which induced decreases in cell water permeability which limits the movement of water to the airway surface, in response to the HS (NaCl), gradient (FIGS. 42A and 42B). The reduction in cell volume and hence cell water permeability is proportional to the rate of HS administration and limits the absolute increases in ASL height/hydration as revealed by the data "mimicking" rapid aerosol deposition with the eFlow (FIG. 41B). Because (1) the maximal ASL height is similar for both deposition rates; (2) the duration of aerosolizing time is shorter for the high flow devices; and (3) as the rates of absorption are similar for the low and high deposition rate devices, the integrated ASL hydration response is smaller with the high flow system. By contrast, delivery of HS at lower flow rates (e.g. 25 nl/min/cm$^2$) produces little cell volume shrinkage (FIGS. 42A and 42B) and no reduction in cellular water permeability, so the full effect of the added NaCl on ASL height is manifested (FIG. 41B). Importantly, while slow delivery of HS for prolonged intervals produces a peak hydration efficacy (maximum ASL height) similar to high flow devices, both the integrated efficacy and duration of efficacy of the slow delivery system are greatly increased compared to short term/high flow delivery systems which are currently used for HS administration (FIG. 41C). We speculate that both the increase in duration and integrated efficacy with HS delivered more slowly than is currently practiced will translate into increased clinical benefit.

Molecular Basis for Cell Shrinkage with Rapid HS Delivery

Figure 43:
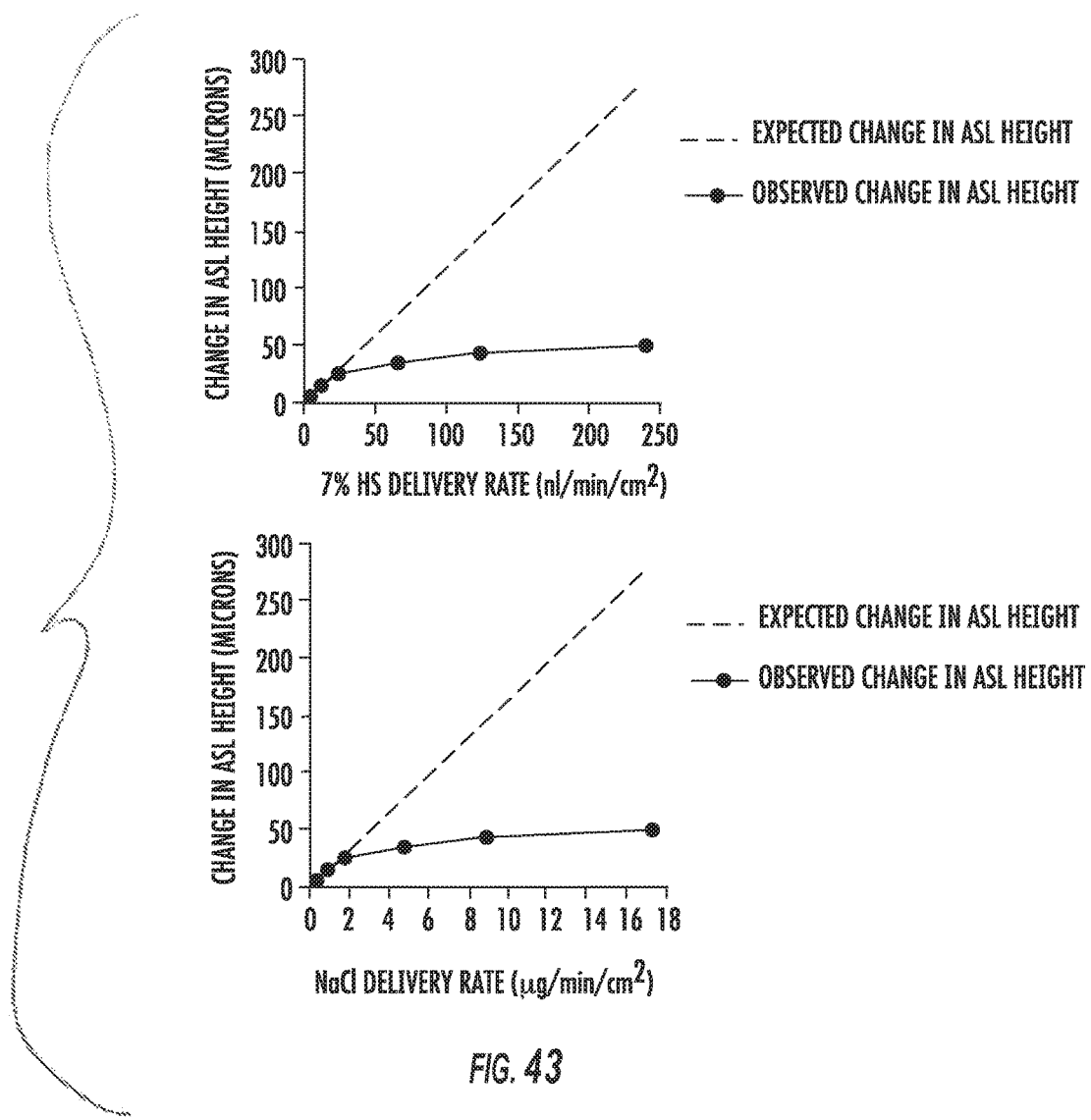

When hypertonic saline is presented to the apical surface of airway epithelia, it raises the osmolarity (tonicity) of the ambient airway surface liquid. Water then flows through water channels contained in the airway epithelia from the submucosal (blood facing side) space to the airway lumen restore the isotonicity of the ASL. Note, the apical membrane is more water permeable than the basolateral membrane, i.e. the cell functions as an "osmometer" that traces ALS osmolarity. If the hypertonic saline is presented at rates faster than water can move from the submucosal space into the cell across the less permeable basolateral membrane, hyperosmolar (hypertonic) liquid on the airway surfaces draws water selectively from the lining airway epithelial cells across the more permeable apical membrane, causing cell shrinkage (collapse). The airway epithelial cells defend themselves from volume depletion and shrinkage by reducing water permeability from the cell membrane contiguous with the airway surface liquid (i.e. the 'apical' membrane), limiting the capacity of the cell to conduct water flow. As expected by this hypothesis, we observed that at low deposition rates, the ASL height (volume) reflects what is predicted from the mass of salt delivered and the amount of water drawn from the submucosa to render the ASL isotonic (FIG. 43). However, at 7% HS delivery rates above 25 nl/min/cm$^2$, the observed change in ASL height is lower than what is expected based on the mass of salt delivered because of cell shrinkage and reduced epithelial water permeability Therefore, these in vitro data indicate that when hypertonic saline is delivered at a high rate, the hydrating activity of inhaled hypertonic saline is reduced by: 1) the reduced capacity of the epithelium to conduct water from the isotonic sub-epithelial space (that contains blood vessels) to the hypertonic ASL; and 2) the active transepithelial absorption of NaCl by the airway epithelium as it is delivered and reaches high concentration. In contrast, slow, "gentle" delivery of HS produces more modest increases in airway surface liquid osmolarity (tonicity), so that (1) there is no cell shrinkage induced reduction of the transepithelial osmotic water flow and (2) the concentration of Na$^+$ and Cl$^-$ in ASL do not rise to sufficiently high levels to accelerate transepithelial Na$^+$ (and Cl$^-$ H$_2$O) adsorption of the aerosol-deposited NaCl.

Slow Delivery of HS Minimizes the Effects of HS on Ciliastasis

Figure 44A:
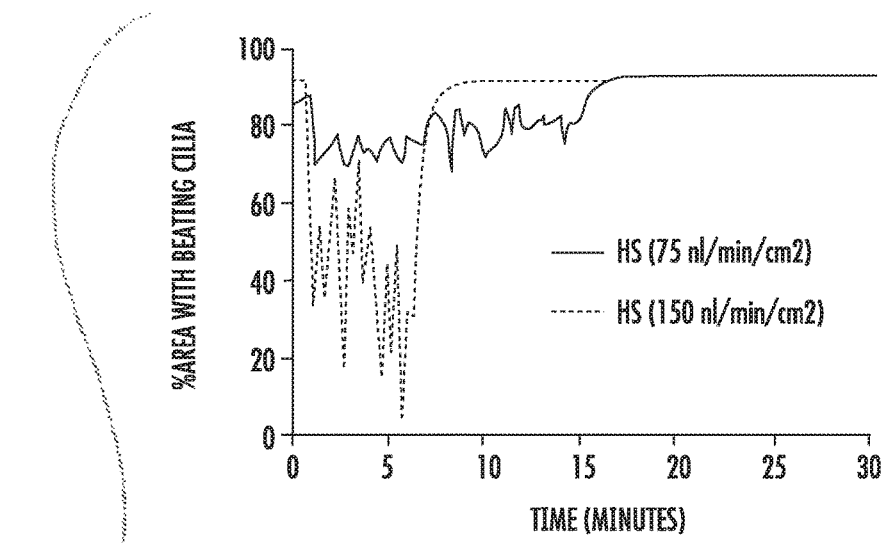
Figure 44B:
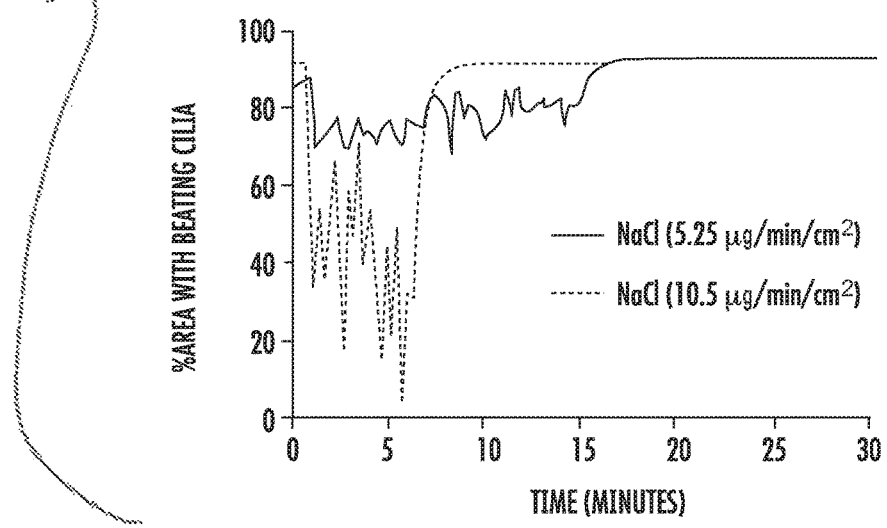

Data from several otolaryngology studies indicate that topical application of hypertonic saline (HS) to the nasopharynx results in significant inhibition of ciliary beat frequency (CBF). These studies were done with bolus administrations of HS similar to the method of rapid HS delivery used in current clinical practice. While HS is well documented to increase airways hydration, the inhibition or slowing of ciliary beating would detract from the overall therapeutic goal of increasing mucus clearance. Little is known about how hypertonic solutions affects cilia beating in human lower airway epithelial cells when given in deposition rates consistent with current clinical inhalation nebulizers (i.e. in the range of nanoliters/min/cm$^2$). As shown in FIGS. 44A-44B, when HS is deposited at a rate which mimics clinical HS administration to primary cultures of human airway epithelia derived from CF airways, the airway epithelial cells shrink (FIGS. 42A and 42B) and the number of beating cilia beating (FIG. 44A) and CBF (FIG. 44B) are immediately reduced. However, as shown in FIG. 43, the slower delivery rate of HS (75 nl/min/cm$^2$) has a much smaller effect of the inhibition of cilia beating (despite that the same amount of NaCl was added to cultures under both HS deposition rates). Taken together, these data support the notion that bolus delivery of HS, as is performed clinically, is not optimal for increasing mucus clearance as the inhibition of CBF is predicted to act counter to the acceleration of mucus clearance achieved when the ASL volume (hydration) is increased. Furthermore, the delivery of the same mass of NaCl over a longer time period produces a maximal increase in hydration, as well as, has a minimal effect on ciliary beating.

Figure 45:
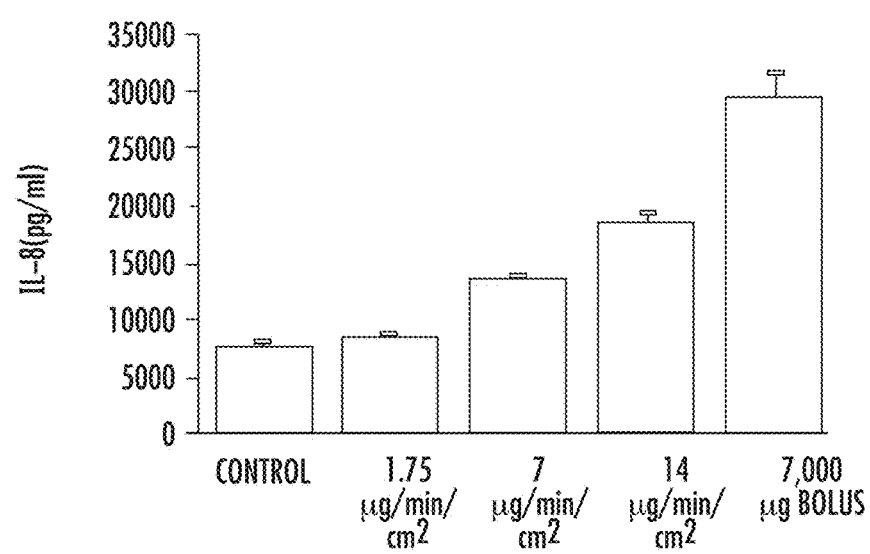

Rapid HS Delivery at Deposition Rates Based on HS Administration Via Pali LC Star and eFlow Leads to Pro-Inflammatory Cytokine Release The rates of NaCl mass deposition representative of HS administration via Pari LC Star (~3.4 mg/min/lung in human subjects and 7 µg/min/cm$^2$ in cell culture) and eFlow (~6.6 mg/min/lung in human subjects and 14 µg/min/cm$^2$ in cell culture) technologies lead to IL-8 cytokine secretion in airway cell culture models (FIG. 45). The relative high rate of NaCl deposition produces cell shrinkage which then leads to cellular stress responses, e.g., IL-8 release, likely linked to the acute drops in FEV$_1$, cough and chest tightness reported in the clinical studies following inhaled HS administration. At the same time, the rates of NaCl deposition representative of HS administration via the CSD-1 device (1.1 µg/min/cm$^2$) do not cause IL-8 secretion. Thus, such low rates are likely key for safe administration of inhaled HS to human subjects.

Figure 46:
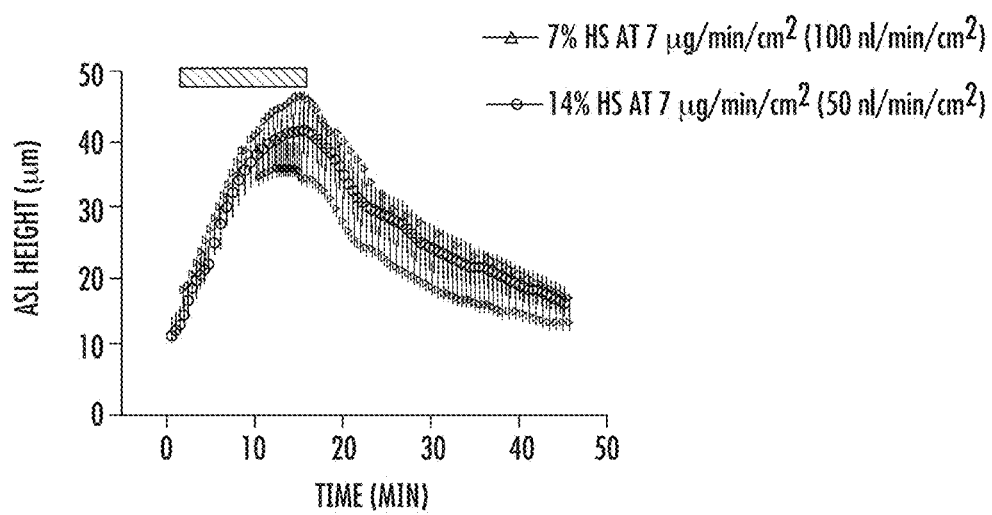

The Use of Higher than 7% HS Formulations with Proportionally Reduced Aerosol Deposition Rates Leads to Increases in ASL Height As outlined above, low rates of NaCl mass deposition appear to be key for safe administration of inhaled HS. 110 mg and 250 mg of NaCl administered into the lungs of CF patients via rapid "bolus" administration, previously shown to be therapeutically effective, into the lung of CF patients over 8 hour extended aerosol administration, i.e. at "slow" rates, are unlikely to release IL-8 and induce ciliastasis. One way to achieve such rates is to use higher than 7% HS formulations. To explore the impact of NaCl delivery at an identical rate to cultures utilizing varying HS % at inverse of aerosol deposition rates, the effect of 7% HS (deposited at 100 nl/min/cm$^2$) and 14% HS (deposited at 50 nl/min/cm$^2$) formulations on the airway surface liquid height, ciliastasis and IL-8 release was explored. 7% and 14% HS formulations, administered as aerosols at the rates of 100 nl/min/cm2 versus 50 nl/min/cm$^2$ onto the surface of the airway cell culture model to both achieving NaCl deposition rates of 7 µg/min/cm$^2$, elicited a similar increase in ASL height (FIG. 46).

Figure 47:
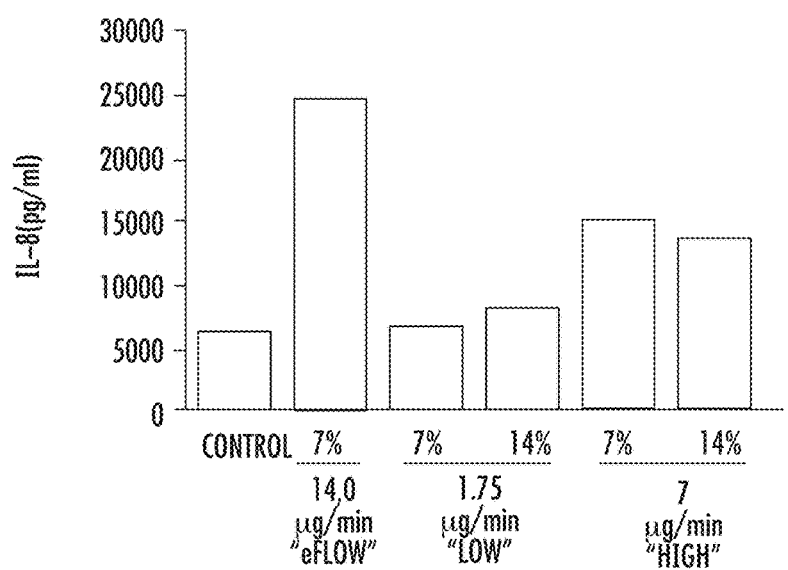
FIG. 47 shows the 1 L-8 secretion in response to 7% and 14% HS administered at equal rates of deposition in cultured human bronchial epithelial cells.

The Use of Higher than 7% HS Formulations with Proportionally Reduced Aerosol Deposition Rates does not Induce IL-8 Secretion The effects of aerosol delivery rate and % HS formulation on IL-8 secretion were explored (FIG. 47). A 7% HS solution delivered at eFlow rates of delivery (14 µg/min/cm$^2$) to airway surfaces produced an increase in IL-8 secretion. Conversely, delivery of 7% HS at Parion CSD-1 deposition rates (1.75 µg/min/cm$^2$) produced no increase in IL-8 secretion. Importantly, delivery of 14% HS, at half the aerosol deposition rates, also produced no increase in IL-8 secretion. Note, delivery of 7% HS at Pari LC Star deposition rates (7 µg/min/cm$^2$) produced in increase in IL-8 secretion. Again, delivery of 14% HS at one half the aerosol rate, did not produce a relative increase in IL-8 secretion.

Figure 48:
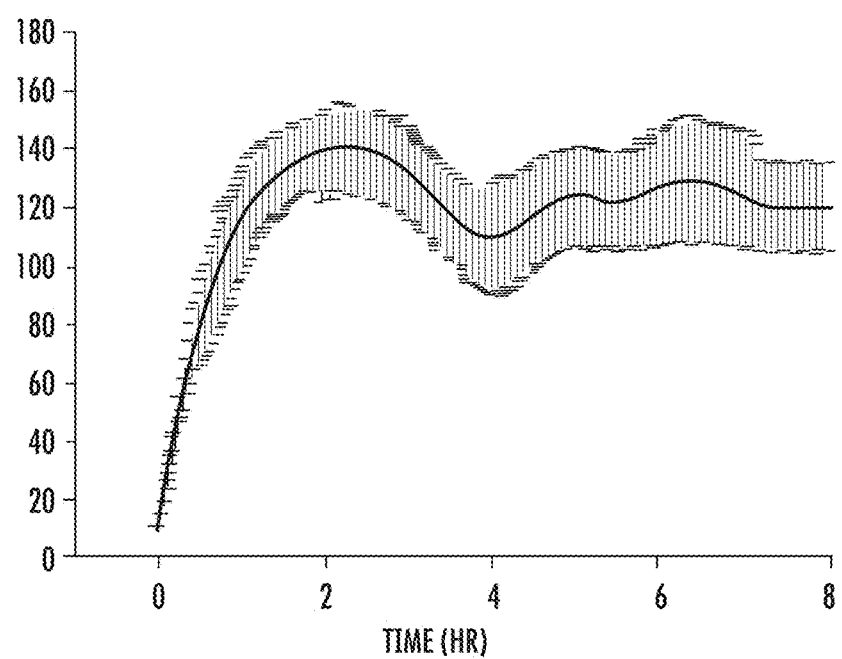
FIG. 48 shows a graph of the sustained effect of 7% HS administered over 8 hours on ASL height in cultured human bronchial epithelial cells.

Slow Extended Administration of HS Aerosol Over 8 Hours Leads to Sustained Restoration of the ASL without Desensitization The effect of extended administration of HS on the airway surface was explored for sustained increase in ASL height. 7% HS aerosol was delivered onto the airway surface for 8 hours at a "slow" rate of 1.75 µg/min/com$^2$. A sustained increase in ASL height was produced that was maintained without abatement over the 8 hours of extended aerosol administration (FIG. 48).

Embodiments of the Invention

A method of treating at least one lung/the lungs of a subject in need thereof, comprising:

administering an active agent to the at least one lung/the lungs of a subject.

A method according to any preceding embodiment, wherein the administering is carried out by aerosol inhalation over extended periods of time via nasal cannula or face mask.

A method according to any preceding embodiment, wherein the administering is carried out by inhalation administration.

A method according to any preceding embodiment, wherein said administering step is carried out by a nasal cannula, face mask, or positive airway pressure mask (e.g., a continuous positive airway pressure (CPAP) mask or a bilevel positive airway pressure (biPAP) mask).

A method according to any preceding embodiment, wherein the administering is carried out by administration of the active agent to airway surfaces.

A method according to any preceding embodiment, wherein the administering is effective to enhance mucus clearance from at least one lung of the subject.

A method according to any preceding embodiment, wherein the administering step is a sustained administering or infusion administering step.

A method according to any preceding embodiment, wherein the administering step comprises limiting the amount of said active agent administered, and/or limiting the rate at which said active agent is administered, so that at least one undesired side-effect of said active agent (e.g., dehydration of lung airway epithelial cells, undesirably high systemic levels of said active agent, receptor desensitization by said active agent, undesirably short residence time in or on a target tissue at sufficiently high concentration, etc.) is reduced.

A method according to any preceding embodiment, wherein the administering step comprises extending the duration for which said active agent is administered so that at least one desired effect of said active agent (e.g., hydration of airway mucus secretions; enhanced mucus clearance; extended residence time in or on a target tissue at sufficiently high concentration) is enhanced (e.g., as compared to the extent of the desired effect achieved when the same amount of said active agent is administered over a shorter period of time, for example: a time of one half, one third, or one quarter the time of the extended duration administration).

A method according to any preceding embodiment, wherein the active agent is a hydrating agent (e.g., an osmolyte, sodium channel blocker, or secretogogue (e.g., a $P2Y_2$ receptor agonist)), a mucus modifying agent (e.g., a reducing agent, a surfactant, an expectorant, DNase), an anti-infective agent, an anti-inflammatory agent, a bronchodilator, NO or an NO donor, another therapeutic agent, or a combination thereof.

A method according to any preceding embodiment, wherein the active agent is a type II antibiotic (e.g., carbapenems, cephalosporins, erythromycin, linezolid, penicillins, etc.) or a type III antibiotic (e.g., azithromycin, clinndamycin, oxazolidinones, tetracyclines, vancomycin, etc.), another therapeutic agent, or a combination thereof.

A method according to any preceding embodiment, wherein the active agent is antivirals such as ribavirin, bronchodilators, siRNAs, gene therapy vectors, aptamers, endothelia-receptor antagonists, alpha-1-antitrypsin orprostacyclins.

A method according to any preceding embodiment, wherein the active agent is a combination of two or more active agents including any combinations of hydrating agents (e.g., an osmolyte, sodium channel blocker, or secretogogue (e.g., a $P2Y_2$ receptor agonist)), mucus modifying agents (e.g., a reducing agent, a surfactant, an expectorant, DNase), anti-infective agents, anti-inflammatory agents, bronchodilators, NO or an NO donors, type II antibiotics (e.g., carbapenems, cephalosporins, erythromycin, linezolid, penicillins, etc.), type III antibiotics (e.g., azithromycin, clinndamycin, oxazolidinones, tetracyclines, vancomycin, etc.), antivirals such as ribavirin, bronchodilators, siRNAs, gene therapy vectors, aptamers, endothelin-receptor antagonists, alpha-1-antitrypsin, prostacyclins or other therapeutic agents.

A method according to any preceding embodiment, wherein said subject is afflicted with cystic fibrosis, chronic bronchitis, emphysema, sinus-related disorders such as rhinitis and sinusitis, chronic obstructive pulmonary disease, aspiration pneumonitis, asthma, and/or a bacterial, viral or fungal infection of the lungs.

A method according to any preceding embodiment, wherein said administering step is carried out for a time of 1, 2 or 4 minutes up to 30, 40 or 60 minutes.

A method according to any preceding embodiment, wherein said administering step is carried out for a time of from 30, 40 or 60 minutes up to 2, 4, 6 or 8 hours.

A method according to any preceding embodiment, wherein said administering step is carried out for a time of 2, 4, 6 or 8 hours up to 12 or 24 hours.

A method according to any preceding embodiment, wherein said administering step is carried out overnight and/or while said subject is sleeping.

A composition comprising an active agent as described herein in a pharmaceutically acceptable carrier for use in carrying out a method of any preceding embodiment.

An aerosol generator or nebulizer (e.g., as described herein) for use in carrying out a method of any preceding embodiment.

The foregoing is illustrative of the present invention, and is not to be construed as limiting thereof.

That which is claimed is:

1. An apparatus comprising:
   an entrainment chamber including a gas inlet and a first aerosol outlet, the gas inlet configured to fluidically couple a gas source to the entrainment chamber to produce an entrained aerosol flow at the first aerosol outlet;
   a nozzle in fluidic communication with the first aerosol outlet of the entrainment chamber, the nozzle configured to alter the velocity of the entrained aerosol flow; and
   a particle selection chamber defining a fluid pathway, the particle selection chamber including a second aerosol outlet and configured to produce an outlet aerosol flow at the second aerosol outlet, the particle selection chamber further configured to receive the entrained aerosol flow from the nozzle and into the fluid pathway, at least a portion of the fluid pathway including a tortuous path configured to remove aerosol particles in the entrained aerosol flow below a predetermined diameter such that a volumetric median diameter (VMD) of the outlet aerosol flow is less than a VMD of the entrained aerosol flow.

2. The apparatus of claim 1, wherein the nozzle is configured to increase the velocity of the entrained aerosol flow.

3. The apparatus of claim 1, wherein the nozzle includes a first end defining an inlet opening having a first cross sectional area, the inlet opening configured to receive the entrained aerosol flow from the aerosol outlet, the nozzle further including a second end defining an outlet opening having a second cross sectional area that is less than the first cross sectional area, the second end in fluid communication with the particle selection chamber.

4. The apparatus of claim 1, wherein the particle selection chamber includes a barrier configured to reduce an amount of the aerosol particles in the entrained aerosol flow that are greater than a predetermined diameter.

5. The apparatus of claim 4, wherein the barrier is selected from one or more of the following: a baffle, a particle filter, a curved barrier, a spiral barrier, and an elutriator.

6. The apparatus of claim 1, wherein the fluid pathway is a nonlinear pathway.

7. The apparatus of claim 1, wherein the aerosol inlet is configured to be coupled to a nebulizer.

8. The apparatus of claim 1, wherein the second aerosol outlet is configured to be connected to a nasal cannula.

9. The apparatus of claim 1, wherein the entrainment chamber defines a rainout outlet port.

10. The apparatus of claim 1, further comprising:
    a container fluidically coupled to the entrainment chamber, the container containing an active agent, the active agent selected from the group consisting of osmolytes, secretogogues, mucus modifying agents (mucolytics), type II antibiotics, and combinations thereof.

* * * * *